United States Patent
Thibeault et al.

(10) Patent No.: US 9,505,775 B2
(45) Date of Patent: Nov. 29, 2016

(54) INHIBITORS OF CYTOMEGALOVIRUS

(71) Applicants: Carl Thibeault, Mascouche (CA); Jean Rancourt, Laval (CA); Pierre L. Beaulieu, Rosemère (CA); Anne Décor, Langenfeld (CA); Chantal Grand-Maitre, Boisbriand (CA); Cyrille Kuhn, Danbury, CT (US); Elisia Villemure, San Francisco, CA (US); Oliver Hucke, Warthausen (DE); Simon Surprenant, Milford, CT (US); Melissa Leblanc, Laval (CA); Jean-Eric Lacoste, Laval (CA); Benoit Moreau, Newton, MA (US); Eric Jolicoeur, Blainville (CA)

(72) Inventors: Carl Thibeault, Mascouche (CA); Jean Rancourt, Laval (CA); Pierre L. Beaulieu, Rosemère (CA); Anne Décor, Langenfeld (CA); Chantal Grand-Maitre, Boisbriand (CA); Cyrille Kuhn, Danbury, CT (US); Elisia Villemure, San Francisco, CA (US); Oliver Hucke, Warthausen (DE); Simon Surprenant, Milford, CT (US); Melissa Leblanc, Laval (CA); Jean-Eric Lacoste, Laval (CA); Benoit Moreau, Newton, MA (US); Eric Jolicoeur, Blainville (CA)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 14/440,085

(22) PCT Filed: Oct. 31, 2013

(86) PCT No.: PCT/US2013/067670
§ 371 (c)(1),
(2) Date: May 1, 2015

(87) PCT Pub. No.: WO2014/070976
PCT Pub. Date: May 8, 2014

(65) Prior Publication Data
US 2015/0274744 A1    Oct. 1, 2015

Related U.S. Application Data

(60) Provisional application No. 61/722,154, filed on Nov. 3, 2012.

(51) Int. Cl.
C07D 403/14    (2006.01)
C07D 403/06    (2006.01)
C07D 413/14    (2006.01)
(Continued)

(52) U.S. Cl.
CPC ......... *C07D 491/107* (2013.01); *C07D 401/14* (2013.01); *C07D 403/06* (2013.01); *C07D 403/08* (2013.01); *C07D 403/14* (2013.01); *C07D 413/14* (2013.01); *C07D 471/04* (2013.01); *C07D 471/10* (2013.01); *C07D 487/10* (2013.01)

(58) Field of Classification Search
CPC .............. C07D 403/14; C07D 403/06; C07D 491/107
USPC .................................. 514/415; 548/469, 494
See application file for complete search history.

(56) References Cited

U.S. PATENT DOCUMENTS 4,423,050 A    12/1983    Verheyden et al.

FOREIGN PATENT DOCUMENTS

WO    9947507 A2    9/1999
WO    0042043 A1    7/2000
(Continued)

OTHER PUBLICATIONS

STN Registry Database entry for CAS RN 1321132-73-3, Published in database on Aug. 21, 2011.*
(Continued)

*Primary Examiner* — Alicia L Otton
*Assistant Examiner* — Sagar Patel
(74) *Attorney, Agent, or Firm* — Michael P. Morris; Edward S. Lazer

(57) ABSTRACT

Compounds of Formula (I) wherein $R^1$, $R^2$, $R^{3A}$, $R^{3B}$, Y, $Z^1$ and $Z^2$ are defined herein, are useful for the treatment of cytomegalovirus disease and/or infection.

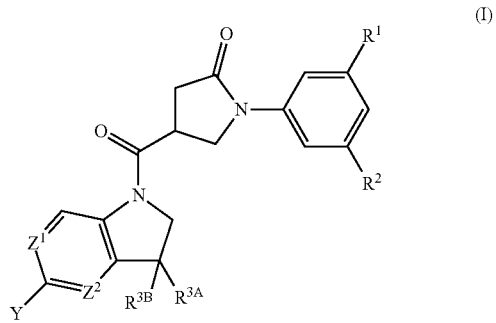

(I)

7 Claims, No Drawings

(51) Int. Cl.
*C07D 401/14* (2006.01)
*C07D 209/04* (2006.01)
*A61K 31/404* (2006.01)
*A61K 31/4178* (2006.01)
*A61K 31/4155* (2006.01)
*A61K 31/4192* (2006.01)
*A61K 31/4196* (2006.01)
*A61K 31/422* (2006.01)
*A61K 31/44* (2006.01)
*A61K 31/497* (2006.01)
*C07D 491/107* (2006.01)
*C07D 403/08* (2006.01)
*C07D 471/04* (2006.01)
*C07D 487/10* (2006.01)
*C07D 471/10* (2006.01)

(56) References Cited

FOREIGN PATENT DOCUMENTS

| | | |
|---|---|---|
| WO | 0170706 A2 | 9/2001 |
| WO | 02064096 A2 | 8/2002 |
| WO | 02070487 | 9/2002 |
| WO | 03059911 A2 | 7/2003 |
| WO | 2004106345 A2 | 12/2004 |
| WO | 2010028862 | 3/2010 |

OTHER PUBLICATIONS

International Search report and Written opinion, PCT/ISSA 220, Mailed Dec. 18, 2014, for PCT/US2013067670.

* cited by examiner

INHIBITORS OF CYTOMEGALOVIRUS

SEQUENCE LISTING

The instant application contains a Sequence Listing which has been submitted in ASCII format via EFS-Web and is hereby incorporated by reference in its entirety. Said ASCII copy, created on Oct. 15, 2013, is named 13-0180_SL.txt and is 728 bytes in size.

FIELD OF THE INVENTION

The present invention relates to γ-lactam analogs and their use as inhibitors of cytomegalovirus (CMV) DNA polymerase, pharmaceutical compositions containing such analogs, and methods of using these analogs in the treatment and prevention of CMV disease and/or infection.

BACKGROUND OF THE INVENTION

CMV, a β-herpes virus, is a frequent and ubiquitous virus that affects all populations, worldwide, including adults and children with normal or compromised immune systems. The current therapies approved for the treatment of CMV include Valganciclovir, Ganciclovir, Cidofovir and Foscarnet. Each of these therapies inhibit CMV DNA polymerase, a protein encoded by the UL54 gene, which is an enzyme essential for viral replication (*PNAS* 2003, 100(24), 14223-14228 and WO 2005/012545).

SUMMARY OF THE INVENTION

The present invention provides a novel series of compounds having inhibitory activity against CMV DNA polymerase.

Further objects of this invention arise for the one skilled in the art from the following description and the examples.

An embodiment of the invention provides a compound of Formula (I) or a racemate, enantiomer, diastereomer or tautomer thereof:

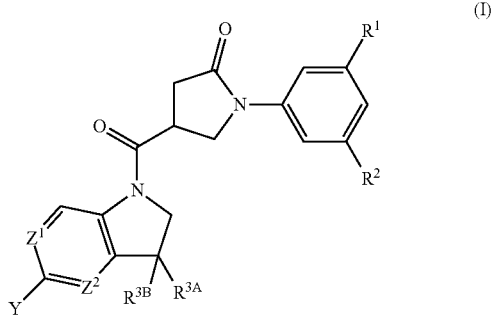

(I)

wherein $R^1$ and $R^2$ are each independently selected from the group consisting of H, halo and —CN;

$R^{3A}$ and $R^{3B}$ are each independently selected from the group consisting of H, $(C_{1-6})$alkyl and $(C_{3-7})$cycloalkyl, wherein each said alkyl and cycloalkyl are optionally mono-, di-, or tri-substituted with $R^{32}$;

or $R^{3A}$ and $R^{3B}$, together with the C to which they are attached, are linked to form a $(C_{3-7})$heterocyclyl or $(C_{3-7})$cycloalkyl; wherein each said heterocyclyl and cycloalkyl are optionally mono-, di-, or tri-substituted with $R^{32}$;

$R^{32}$ is each independently selected from the group consisting of halo, —CN, OH, —O—$(C_{1-6})$alkyl, —C(=O)—$(C_{1-6})$alkyl, $(C_{3-7})$cycloalkyl, $(C_{1-6})$haloalkyl and $(C_{1-6})$alkyl optionally mono- or di-substituted with OH, CN, —O—$(C_{1-6})$alkyl, —$NH_2$, —NH$(C_{1-6})$alkyl or —N$((C_{1-6})$alkyl$)_2$;

$Z^1$ is $C(R^4)$ or N;

$R^4$ is H, halo, —CN, $(C_{1-6})$alkyl, OH, —O—$(C_{1-6})$alkyl or $(C_{1-6})$haloalkyl;

Y is —$(C_{1-6})$alkyl-$R^5$, —$(C_{1-6})$alkyl-O—$R^5$, —$(C_{1-6})$alkyl-N$(R^{51})$—$(C_{1-6})$alkyl-$R^5$ or —$(C_{1-6})$alkyl-N$(R^{51})$—$R^5$;

$R^{51}$ is H or $(C_{1-6})$alkyl;

$R^5$ is aryl, heterocyclyl or heteroaryl; wherein each said aryl, heterocyclyl and heteroaryl are optionally mono-, di-, or tri-substituted with $R^{52}$;

$R^{52}$ is each independently selected from the group consisting of $(C_{1-6})$alkyl, $(C_{2-6})$alkenyl, —CN, —OH, —O$(C_{1-6})$alkyl, halo, —C(=O)OH, —O—$(C_{1-6})$alkyl, $(C_{3-7})$cycloalkyl, —O—$(C_{3-7})$cycloalkyl, $(C_{1-6})$haloalkyl, —$NH_2$, —NH$(C_{1-6})$alkyl, —N$((C_{1-6})$alkyl$)_2$, —$(C_{1-6})$alkyl-C(=O)OH, —$(C_{2-6})$alkenyl-C(=O)OH, —C(=O)—O—$(C_{1-6})$alkyl and —C(=O)—$NH_2$;

$Z^2$ is $C(R^6)$ or N;

$R^6$ is H, halo, —CN, $(C_{1-6})$alkyl, OH, —O—$(C_{1-6})$alkyl or $(C_{1-6})$haloalkyl;

or a salt thereof.

Another embodiment of this invention provides a compound of Formula (I), or a pharmaceutically acceptable salt thereof, as a medicament.

Also within the scope of this invention is the use of a compound of Formula (I), or a pharmaceutically acceptable salt thereof, for the manufacture of a medicament for the treatment or prevention of CMV disease and/or infection in a human being.

Included within the scope of this invention is a pharmaceutical composition comprising a compound of Formula (I), or a pharmaceutically acceptable salt thereof, and a pharmaceutically acceptable carrier.

According to a further aspect of this embodiment the pharmaceutical composition according to this invention further comprises a therapeutically effective amount of at least one other antiviral agent.

The invention also provides the use of a pharmaceutical composition as described hereinabove for the treatment of a CMV infection in a human being having or at risk of having the infection.

The invention also provides the use of a pharmaceutical composition as described hereinabove for the treatment of CMV disease in a human being having or at risk of having the disease.

Another aspect of the invention involves a method of treating or preventing CMV disease and/or infection in a human being by administering to the human being an anti-CMV virally effective amount of a compound of the invention, a pharmaceutically acceptable salt thereof, or a composition as described above, alone or in combination with at least one other antiviral agent, administered together or separately.

An additional aspect of this invention refers to an article of manufacture comprising a composition effective to treat CMV disease and/or infection; and packaging material comprising a label which indicates that the composition can be used to treat disease and/or infection by CMV; wherein the composition comprises a compound of formula (I) according to this invention or a pharmaceutically acceptable salt thereof.

Still another aspect of this invention relates to a method of inhibiting the replication of CMV comprising exposing the virus to an effective amount of the compound of Formula (I), or a salt thereof, under conditions where replication of CMV is inhibited.

Further included in the scope of the invention is the use of a compound of Formula (I), or a salt thereof, to inhibit the replication of CMV.

DETAILED DESCRIPTION OF PREFERRED EMBODIMENTS

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the first named subgroup is the radical attachment point, for example, the substituent "—$C_{1-3}$-alkyl-aryl" means an aryl group which is bound to a $C_{1-3}$-alkyl-group, with the $C_{1-3}$-alkyl group bound to the core. Unless specifically stated otherwise, for groups comprising two or more subgroups, the substituent may be attached to either subgroup.

In case a compound of the present invention is depicted in the form of a chemical name and as a formula in case of any discrepancy the formula shall prevail. An asterisk or the designation, - - - -, may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers, atropisomers) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

One skilled in the art would know how to separate, enrich, or selectively prepare the enantiomers of the compounds of the present invention. Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include but not limited to chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, including but not limited to GC, HPLC, CE, or NMR, and assignment of absolute configuration and conformation, including but not limited to CD, ORD, X-ray crystallography, or NMR.

The term "halo" generally denotes fluorine, chlorine, bromine and iodine.

The term "$C_{1-n}$-alkyl", wherein n is an integer from 2 to n, either alone or in combination with another radical, denotes an acyclic, saturated, branched or linear hydrocarbon radical with 1 to n C atoms. For example the term $C_{1-3}$-alkyl embraces the radicals $H_3C-$, $H_3C-CH_2-$, $H_3C-CH_2-CH_2-$ and $H_3C-CH(CH_3)-$.

The term "$C_{2-n}$-alkenyl", is used for a group as defined in the definition for "$C_{1-n}$-alkyl" with at least two carbon atoms, if at least two of those carbon atoms of said group are bonded to each other by a double bond.

The term "carbocyclyl" or "carbocycle" as used herein, either alone or in combination with another radical, means a mono-, bi- or tricyclic ring structure consisting of 3 to 14 carbon atoms. The term "carbocyclyl" or "carbocycle" refers to fully saturated and aromatic ring systems and partially saturated ring systems. The term "carbocyclyl" or "carbocycle" encompasses fused, bridged and spirocyclic systems.

The term "$C_{3-n}$-cycloalkyl", wherein n is an integer 4 to n, either alone or in combination with another radical, denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "aryl" as used herein, either alone or in combination with another radical, denotes a carbocyclic aromatic monocyclic group containing 6 carbon atoms which may be further fused to at least one other 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring system including aromatic ring systems containing one or more heteroatoms selected from N, O or S(O)$_r$, wherein r=0, 1 or 2, consisting of 3 to 14 ring atoms wherein none of the heteroatoms is part of the aromatic ring. The term "heterocyclyl" or "heterocycle" is intended to include all the possible isomeric forms and all spiro, bridged and fused systems. Thus, the term "heterocyclyl" or "heterocyclyl" includes the following exemplary structures which are not depicted as radicals as each form may be attached through a covalent bond to any atom so long as appropriate valences are maintained:

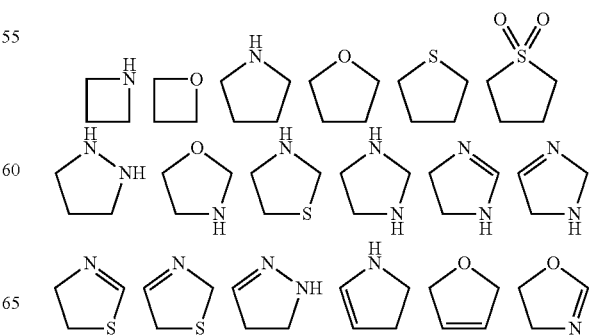

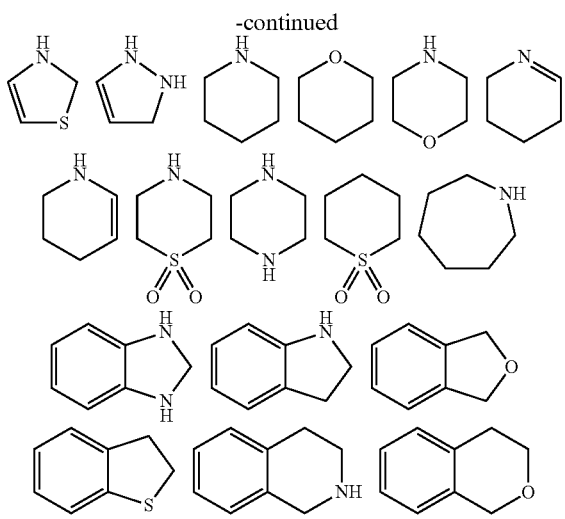
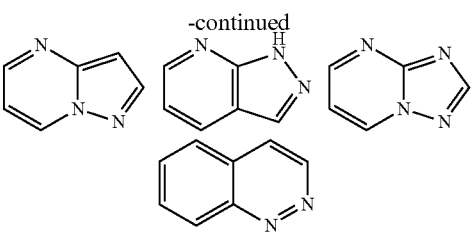

The term "heteroaryl" means a mono- or polycyclic-ring system containing one or more heteroatoms selected from N, O or $S(O)_r$, wherein r=0, 1 or 2, consisting of 5 to 14 ring atoms wherein at least one of the heteroatoms is part of an aromatic ring. The term "heteroaryl" is intended to include all the possible isomeric forms and all spiro, bridged and fused systems.

Thus, the term "heteroaryl" includes the following exemplary structures which are not depicted as radicals as each form may be attached through a covalent bond to any atom so long as appropriate valences are maintained:

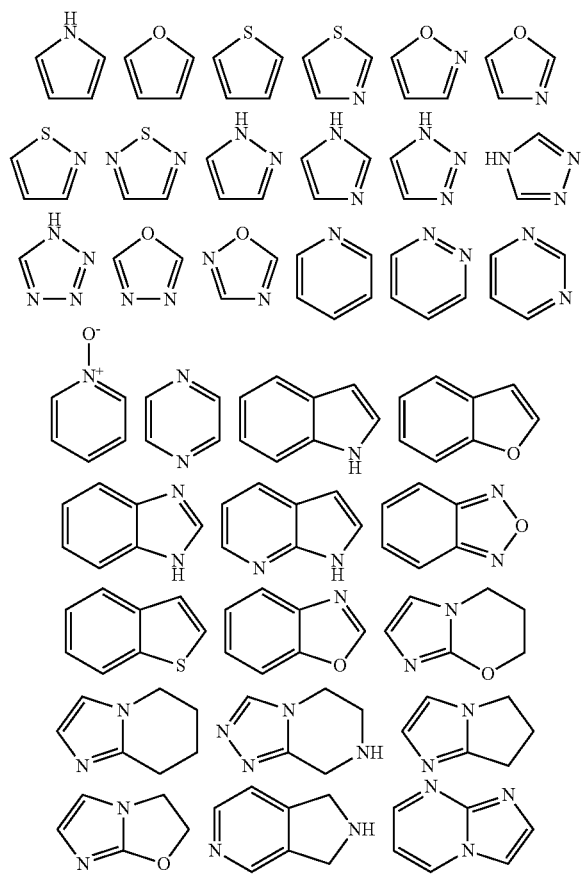

Many of the terms given above may be used repeatedly in the definition of a formula or group and in each case have one of the meanings given above, independently of one another.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

As used herein, the term "treatment" means the administration of a compound or composition according to the present invention to alleviate or eliminate symptoms of CMV disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood, to prevent the appearance of symptoms of the disease.

The term "therapeutically effective amount" means an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

Further Embodiments

In the following preferred embodiments, groups and substituents of the compounds of Formula (I) according to this invention are described in detail.

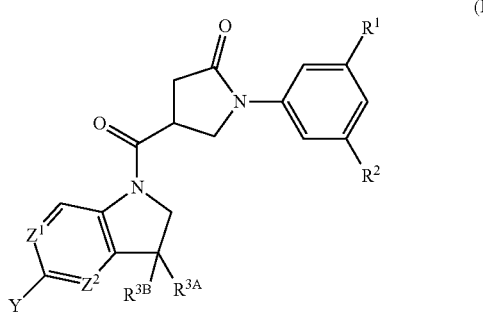

(I)

Any and each of the definitions below may be combined with each other.

$R^1/R^2$:

$R^1/R^2$-A: $R^1$ and $R^2$ are each independently selected from the group consisting of H, halo and —CN.

$R^1/R^2$—B: One of $R^1$ and $R^2$ is halo or —CN and the other of $R^1$ and $R^2$ is H.

$R^1/R^2$—C: One of $R^1$ and $R^2$ is Cl or —CN and the other of $R^1$ and $R^2$ is H.

$R^{3A}$ and $R^{3B}$:

$R^{3A}$ and $R^{3B}$-A: $R^{3A}$ and $R^{3B}$ are each independently selected from the group consisting of H, $(C_{1-6})$alkyl and $(C_{3-7})$cycloalkyl, wherein each said alkyl and cycloalkyl are optionally mono-, di-, or tri-substituted with $R^{32}$;

or $R^{3A}$ and $R^{3B}$, together with the C to which they are attached, are linked to form a $(C_{3-7})$heterocyclyl or $(C_{3-7})$cycloalkyl; wherein each said heterocyclyl and cycloalkyl are optionally mono-, di-, or tri-substituted with $R^{32}$;

$R^{32}$ is each independently selected from the group consisting of halo, —CN, OH, —O—$(C_{1-6})$alkyl, —C(=O)—$(C_{1-6})$alkyl, $(C_{3-7})$cycloalkyl, $(C_{1-6})$haloalkyl and $(C_{1-6})$alkyl optionally mono- or di-substituted with OH, CN, —O—$(C_{1-6})$alkyl, —NH$_2$, —NH$(C_{1-6})$alkyl or —N$((C_{1-6})$alkyl$)_2$.

$R^{3A}$ and $R^{3B}$—B: $R^{3A}$ and $R^{3B}$ are each independently selected from the group consisting of H or $(C_{1-6})$alkyl, optionally mono- or di-substituted with OH or —O—$(C_{1-6})$alkyl;

or $R^{3A}$ and $R^{3B}$, together with the C to which they are attached, are linked to form a $(C_{3-7})$cycloalkyl; optionally mono- or di-substituted with halo, —CN, OH, —O—$(C_{1-6})$alkyl, —C(=O)—$(C_{1-6})$alkyl, $(C_{1-6})$haloalkyl and $(C_{1-6})$alkyl.

$R^{3A}$ and $R^{3B}$—C: $R^{3A}$ and $R^{3B}$ are each independently selected from the group consisting of H and $(C_{1-6})$alkyl.

$Z^1$:

$Z^1$-A: $Z^1$ is $C(R^4)$ or N;

$R^4$ is H, halo, —CN, $(C_{1-6})$alkyl, OH, —O—$(C_{1-6})$alkyl or $(C_{1-6})$haloalkyl.

$Z^1$—B: $Z^1$ is $C(R^4)$;

$R^4$ is H, halo, —CN, $(C_{1-6})$alkyl, OH, —O—$(C_{1-6})$alkyl or $(C_{1-6})$haloalkyl.

$Z^1$—C: $Z^1$ is CH.

Y:

Y-A: Y is —$(C_{1-6})$alkyl-$R^5$, —$(C_{1-6})$alkyl-O—$R^5$, —$(C_{1-6})$alkyl-N$(R^{51})$—$(C_{1-6})$alkyl-$R^5$ or —$(C_{1-6})$alkyl-N$(R^{51})$—$R^5$ and $R^{51}$ is H or $(C_{1-6})$alkyl.

Y—B: Y is —$(C_{1-6})$alkyl-$R^5$ or —$(C_{1-6})$alkyl-N$(R^{51})$—$R^5$ and $R^{51}$ is H or $(C_{1-6})$alkyl.

Y—C: Y is $(C_{1-6})$alkyl-$R^5$.

$R^5$:

$R^5$-A: $R^5$ is aryl, heterocyclyl or heteroaryl; wherein each said aryl, heterocyclyl and heteroaryl are optionally mono-, di-, or tri-substituted with $R^{52}$;

$R^{52}$ is each independently selected from the group consisting of $(C_{1-6})$alkyl, $(C_{2-6})$alkenyl, —CN, —OH, —O$(C_{1-6})$alkyl, halo, —C(=O)OH, —O—$(C_{1-6})$alkyl, $(C_{3-7})$cycloalkyl, —O—$(C_{3-7})$cycloalkyl, $(C_{1-6})$haloalkyl, —NH$_2$, —NH$(C_{1-6})$alkyl, —N$((C_{1-6})$alkyl$)_2$, —$(C_{1-6})$alkyl-C(=O)OH, —$(C_{2-6})$alkenyl-C(=O)OH, —C(=O)—O—$(C_{1-6})$alkyl and —C(=O)—NH$_2$.

$R^5$—B: $R^5$ is a heterocyclyl or heteroaryl, wherein each said heterocyclyl and heteroaryl are optionally mono-, di-, or tri-substituted with $R^{52}$;

$R^{52}$ is each independently selected from the group consisting of $(C_{1-6})$alkyl, —CN, —OH, —O$(C_{1-6})$alkyl, halo, —C(=O)OH, —O—$(C_{1-6})$alkyl, $(C_{1-6})$haloalkyl, —NH$_2$, —NH$(C_{1-6})$alkyl, —N$((C_{1-6})$alkyl$)_2$, —$(C_{1-6})$alkyl-C(=O)OH, $(C_{2-6})$alkenyl and —$(C_{2-6})$alkenyl-C(=O)OH.

$R^5$—C: $R^5$ is a 5- or 6-membered heteroaryl, optionally mono-, di-, or tri-substituted with $R^{52}$;

$R^{52}$ is each independently selected from the group consisting of $(C_{1-6})$alkyl, —CN, —OH, —O$(C_{1-6})$alkyl, halo, —C(=O)OH, —O—$(C_{1-6})$alkyl, $(C_{1-6})$haloalkyl, —NH$_2$, —NH$(C_{1-6})$alkyl and —N$((C_{1-6})$alkyl$)_2$.

$Z^2$:

$Z^2$-A: $Z^2$ is $C(R^6)$ or N;

$R^6$ is H, halo, —CN, $(C_{1-6})$alkyl, OH, —O—$(C_{1-6})$alkyl or $(C_{1-6})$haloalkyl.

$Z^2$—B: $Z^2$ is $C(R^6)$;

$R^6$ is H, halo, —CN, $(C_{1-6})$alkyl, OH, —O—$(C_{1-6})$alkyl or $(C_{1-6})$haloalkyl.

$Z^2$—C: $Z^2$ is CH.

Further subgeneric embodiments of the present invention are set forth in the following table, wherein each substituent group of each embodiment is defined according to the definitions set forth above:

| Embodiment | $R^1/R^2$ | $R^{3A}/R^{3B}$ | $Z^1$ | Y | $R^5$ | $Z^2$ |
|---|---|---|---|---|---|---|
| E-1 | $R^1/R^2$—C | $R^{3A}/R^{3B}$—C | $Z^1$—C | Y—C | $R^5$—C | $Z^2$—C |
| E-2 | $R^1/R^2$—B | $R^{3A}/R^{3B}$—C | $Z^1$—C | Y—B | $R^5$—B | $Z^2$—C |
| E-3 | $R^1/R^2$—A | $R^{3A}/R^{3B}$—B | $Z^1$—C | Y—C | $R^5$—C | $Z^2$—C |
| E-4 | $R^1/R^2$—A | $R^{3A}/R^{3B}$—C | $Z^1$—C | Y—B | $R^5$—B | $Z^2$—C |
| E-5 | $R^1/R^2$—A | $R^{3A}/R^{3B}$—B | $Z^1$—B | Y—B | $R^5$—B | $Z^2$—B |

Examples of most preferred compounds according to this invention are each single compound of the invention namely, compounds 11a1, 11aa1, 11aaa1, 11bb1, 11bbb1, 11bbb2, 11c1, 11cc1, 11ccc1, 11dd1, 11ddd1, 11e1, 11ee1, 11eee1, 11f1, 11ff1, 11fff1, 11g1, 11gg1, 11ggg1, 11h1, 11hh1, 11hhh1, 11i1, 11iii1, 11jjj1, 11m1, 11n1, 11oo1, 11pp1, 11q1, 11qq1, 11r1, 11rr1, 11s1, 11ss1, 11t1, 11tt1, 11u1, 11uu1, 11v1, 11vv1, 11w1, 11ww1, 11x1, 11xx1, 11y1, 11yy1, 11z1, 11zz1, 13a1, 13b1, 13c1, 13d1, 13e1, 13f1, 13g1, 13k1, 13l1, 13n1, 13o1, 13p1, 13q1, 13r1, 13s1, 13t1, 13u1, 13v1, 13w1, 13w2, 13x1, 13y1, 16a3, 16b3, 16c3, 16d3, 17b1, 17f1, 17g1, 17l1, 17m1, 17n1, 17o1, 19a2, 19b2, 19c2, 22a1, 22a2, 22aa1, 22b1, 22bb1, 22c1, 22d1, 22dd1, 22e1, 22f1, 22g1, 22h1, 22i1, 22j1, 22k1, 22ll.1, 22ll.2, 22m1, 22n1, 22o1, 22p1, 22q1, 22r1, 22s1, 22t1, 22u1, 22v1, 22w1, 22x1, 22y1, 22z1, 24a1, 24d1, 24e1, 24f1, 31a1 and 8l1.

Pharmaceutical Composition

Suitable preparations for administering the compounds of the invention will be apparent to those with ordinary skill in the art and include for example tablets, pills, capsules, suppositories, lozenges, troches, solutions, syrups, elixirs, sachets, injectables, inhalatives and powders. The content of the pharmaceutically active compound(s) should be in the range from 0.05 to 90 wt.-%, preferably 0.1 to 50 wt.-% of the composition as a whole.

Suitable tablets may be obtained, for example, by mixing one or more compounds according to the invention with known excipients, for example inert diluents, carriers, disintegrants, adjuvants, surfactants, binders and/or lubricants. The tablets may also consist of several layers.

Suitable injectables may be obtained, for example, by mixing one or more compounds according to the invention with known excipients, for example inert diluents, carriers, co-solvent, adjuvants, surfactants and/or cyclodextrin complex. The injectable formulation may be an emulsion or suspension.

Combination Therapy

Combination therapy is contemplated wherein a compound of the invention, or a pharmaceutically acceptable salt thereof, is co-administered with at least one additional agent selected from: a CMV entry inhibitor, a CMV early transcription event inhibitor, a CMV helicase-primase inhibitor, an other CMV DNA polymerase inhibitor, an inhibitor of UL97 kinase, a CMV protease inhibitor, a CMV terminase inhibitor, a CMV maturation inhibitor, an inhibitor of another target in the CMV life cycle, a CMV vaccine and a CMV biological agent.

These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of the invention, or a pharmaceutically acceptable salt thereof.

The dose range of the compounds of the invention applicable per day is usually from 0.01 to 100 mg/kg of body weight, preferably from 0.1 to 50 mg/kg of body weight. Each dosage unit may conveniently contain from 5% to 95% active compound (w/w). Preferably such preparations contain from 20% to 80% active compound.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

When the composition of this invention comprises a combination of a compound of the invention and one or more additional therapeutic or prophylactic agent, both the compound and the additional agent should be present at dosage levels of between about 10 to 100%, and more preferably between about 10 and 80% of the dosage normally administered in a monotherapy regimen.

Antiviral agents contemplated for use in such combination therapy include agents (compounds or biologicals) that are effective to inhibit the production and/or replication of a virus in a human being, including but not limited to agents that interfere with either host or viral mechanisms necessary for the production and/or replication of a virus in a human being. Such agents can be selected from: a CMV entry inhibitor; a CMV early transcription event inhibitor; a CMV helicase-primase inhibitor; a CMV DNA polymerase inhibitor such as Ganciclovir (Cytovene), Valganciclovir (Valcyte; Cymeval), Cidofovir (Vistide), Foscarnet (Foscavir), CMX001, cyclopropavir (MBX-400) and Valaciclovir (Valtrex; Zelitrex); an inhibitor of UL97 kinase such as Maribavir; a CMV protease inhibitor; a CMV terminase inhibitor such as AIC246 (Letermovir); a CMV maturation inhibitor; other inhibitors such as Artesunate; a CMV vaccine such as TransVax and a CMV biological agent such as Cytogam (Cytotect), TCN-202 and CMV IgG.

EXAMPLES

Other features and advantages of the present invention will become apparent from the following more detailed Examples which illustrate, by way of example, the principles of the invention. As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. Flash chromatography is performed on Teledyne Isco CombiFlash® Rf system or Teledyne Torrent using RediSep® Normal-phase Silica Flash Columns or RediSep Rf Gold® Normal-Phase Silica Columns or SiliaSep™ Universal Closed-Top Flash Cartridges or InnoFlash™ Silica Flash Column.

All of the compounds of the invention are synthesized analogously to the specific Examples described below. Retention times ($t_R$) for each compound are measured using the standard analytical HPLC or UPLC conditions described below. As is well known to one skilled in the art, retention time values are sensitive to the specific measurement conditions. Therefore, even if identical conditions of solvent, flow rate, linear gradient, and the like are used, the retention time values may vary when measured, for example, on different HPLC or UPLC instruments. Even when measured on the same instrument, the values may vary when measured, for example, using different individual HPLC or UPLC columns, or, when measured on the same instrument and the same individual column, the values may vary, for example, between individual measurements taken on different occasions. A person skilled in the art will recognize that obvious modifications to the synthetic methods, including the amount of time indicated to perform the various steps, may be required to generate each of the specific compounds listed in the Examples section.

Preparative RP-HPLC is performed under standard conditions using one of the following specific measuring conditions:

Compounds are purified by preparative RP-HPLC under standard conditions using a Waters SunFire Prep OBD™ C18 column (5 μm, 19×50 mm) eluting with a linear MeOH:water gradient containing 10 mM Ammonium Formate (pH 3.8) over 10 minutes at 30 mL/min. Fractions containing the desired product are pooled and lyophilized.

Compounds are purified by preparative RP-HPLC under standard conditions using a Waters XBridge Prep OBD™ C18 (5 μm, 19×50 mm) eluting with a linear MeOH:water gradient containing 10 mM Ammonium Bicarbonate (pH 10) over 10 minutes at 30 mL/min. Fractions containing the desired product are pooled and lyophilized.

Compounds are purified by preparative RP-HPLC under standard conditions using a Waters SunFire Prep OBD™ C18 column (5 μm, 19×50 mm) eluting with a linear acetonitrile:water gradient containing 0.06% TFA (v/v) 10 minutes at 30 mL/min. Fractions containing the desired product are pooled and lyophilized.

Analytical UPLC is performed under standard conditions using one of the following specific measuring conditions:

Analytical UPLC is carried out under standard conditions using a Waters ACQUITY UPLC® HSS T3 column (1.8 μm, 2.1×50 mm) eluting with a segmented linear MeCN gradient containing 0.06% TFA (v/v) over 2.6 min at 0.9 mL/min.

Analytical UPLC is also carried out under standard conditions using a Waters ACQUITY UPLC® BEH C18 column (1.8 μm, 2.1×30 mm) eluting with a linear MeOH gradient containing 10 mM Ammonium Bicarbonate (pH 10) over 2.2 min at 0.75 mL/min or a Waters ACQUITY UPLC® HSS C18 column (1.8 μm, 2.1×30 mm) eluting with a linear MeOH gradient containing 10 mM Ammonium Formate (pH 3.8) over 2.3 min at 0.8 mL/min.

Mass spectral analyses are recorded using electrospray mass spectrometry.

Enantiomers can be separated by preparative SFC-MS under standard conditions using one condition combination of the following matrix of conditions:

1. SFC (multiple stacked injections): SFC-MS: Waters Prep 100, Column: type see table 1: 21.2×250 mm at 40° C., Eluent A: $CO_2$, Eluent B: see table 1, Gradient: Isocratic X:Y $CO_2$:eluant B at 50 mL/min, Back Pressure Regulator: 150 Bars, Run Time: 10 min.

2. SFC (multiple stacked injections): SFC-MS: Waters Prep 15, Column: type see table 1:10×250 mm at 40° C., Eluent A: $CO_2$, Eluent B: see table 1, Gradient:Isocratic X:Y $CO_2$:eluant B at 10 mL/min, Back Pressure Regulator: 150 Bars, Run Time: 10 min.

Analytical SFC-MS is performed under standard conditions using one condition combination of the following matrix of conditions:

1. SFC (multiple stacked injections): SFC-MS: Waters Prep 15, Column: type see table 1: 10×250 mm at 40° C., Eluent A: $CO_2$, Eluent B: see table 1, Gradient:Isocratic X:Y $CO_2$:eluant B at 10 mL/min, Back Pressure Regulator: 150 Bars, Run Time: 10 min.

Abbreviations or symbols used herein include:

Ac: acetyl; AcOH: acetic acid; ACCN: 1,1'-azobis(cyclohexanecarbonitrile); AmBic: Ammonium bicarbonate; AmFor: Ammonium formate; BEH: ethylene bridged hybrid; Bn: benzyl (phenylmethyl); BOC or Boc: tert-butyloxycarbonyl; Bu: butyl; BBN: 9-borabicyclo[3.3.1] nonane; DCM: dichloromethane; DIPEA: N,N-diisopropylethylamine; DMAP: 4-dimethylaminopyridine; DME: dimethoxyethane; DMF: N,N-dimethylformamide; $EC_{50}$: 50% effective concentration; EDCI: 1-ethyl-3-(3-dimethylaminopropyl)carbodiimide; Et: ethyl; $Et_3N$: triethylamine; $Et_2O$: diethyl ether; EtOAc: ethyl acetate; EtOH: ethanol; Hex: hexanes; HATU: N,N,N',N'-tetramethyl-O-(7-azabenzotriazol-1-Auronium hexafluorophosphate; HPLC: high performance liquid chromatography; HSS: high strength silica; $^iPr$ or i-Pr: 1-methylethyl (iso-propyl); LC-MS: liquid chromatography-mass spectrometry; m/z: mass-to-charge ratio; [M+H]$^+$: protonated molecular ion; Me: methyl; MeCN: acetonitrile; MeOH: methanol; MS: mass spectrometry; NMP: N-methyl-2-pyrrolidone; OBD: optimum bed density; Ph: phenyl; Pr: propyl; Prep LCMS: preparative liquid chromatography-mass spectrometry; SFC: Supercritical fluid chromatography; SFC-MS: Supercritical fluid chromatography-mass spectrometry; RP-HPLC: reversed-phase high pressure liquid chromatography; RT: room temperature (approximately 18° C. to 25° C.); tert-butyl or t-butyl: 1,1-dimethylethyl; TFA: trifluoroacetic acid; THF: tetrahydrofuran; $t_R$: retention time; UPLC: ultra performance liquid chromatography.

Example 1

Preparation of Intermediate 1a2

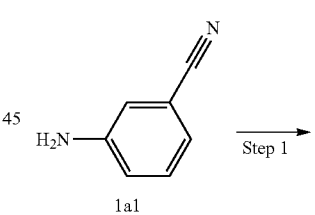

1a1

TABLE 1

Matrix of SFC conditions (Column type and Eluent B)

| Eluant B | Column | | | | | | | |
|---|---|---|---|---|---|---|---|---|
| | ChiralPak IA | ChiralPak IB | ChiralPak IC | ChiralPak IS | Lux Cellulose-2 | Lux Cellulose-3 | Lux Cellulose-4 | Lux Amylose-2 |
| MeOH | • | • | • | • | • | • | • | • |
| EtOH | • | • | • | • | • | • | • | • |
| iPrOH | • | • | • | • | • | • | • | • |
| MeOH + 2 mM AmBic | • | • | • | • | • | • | • | • |
| MeOH + 10 mM AmFor | • | • | • | • | • | • | • | • |
| EtOH + 2 mM AmBic | • | • | • | • | • | • | • | • |

-continued

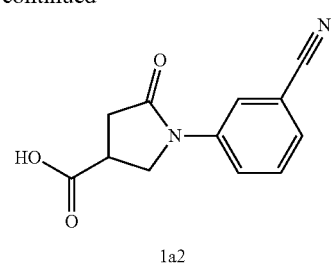

1a2

Step 1:

A mixture of the 3-aminobenzonitrile 1a1 (Aldrich) (43.7 g, 0.37 mol) and itaconic acid (Aldrich) (47.6 g, 0.37 mol) is heated at 160° C. for 1 h. The residue is cooled to RT then water is added. The resulting precipitate is dissolved in NaOH 1N. The residue is filtered then the filtrate is acidified with concentrated HCl. The residue is filtered and washed with water. The solids are dried under vacuum, pre-adsorbed on silica gel and purified on Rf Combi-Flash (eluting 0-35% MeCN/CH$_2$Cl$_2$) to afford 1a2 ($t_R$=0.9 min, (M+H)$^+$ 231.1).

The following intermediates are prepared analogously to the procedure described in Example 1 starting from the appropriate aniline.

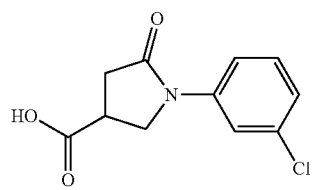

1b2

Example 2

Preparation of Intermediate 2a2

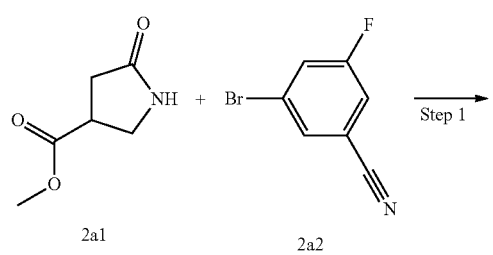

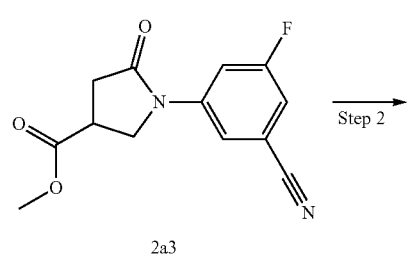

2a3

-continued

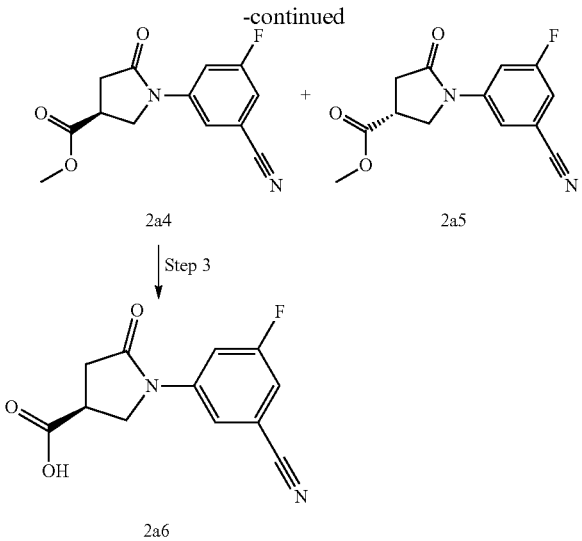

2a4 + 2a5

Step 3 ↓

2a6

Step 1:

2a1 (Synchem-inc, 1.72 g, 12 mmol), 2a2 (Matrix, 2 g, 10 mmol), cesium carbonate (4.9 g, 15 mmol), tris(dibenzylideneacetone)dipalladium(O) (229 mg, 0.25 mmol) and 4,5-bis-diphenylphosphanyl-9,9-dimethyl-9H-xanthene (289 mg, 0.5 mmol) are placed in 1,4-dioxane (20 mL). The mixture is degassed with argon for 20 min and heated at 100° C. for 16 h. The reaction mixture is cooled to RT, EtOAc is added and the organic layer is washed with water and brine. The organic layer is dried over Na$_2$SO$_4$, filtered and concentrated in vacuo. The product is purified by flash chromatography (10%-80% EtOAc:hexanes) to afford 2a3 ($t_R$=1.3 min, (M+H)$^+$ 263.1).

Step 2:

2a3 (1.8 g, 6.7 mmol) is dissolved in a (1:1) mixture of MeOH and DCM (16 mL). The enantiomers are separated by SFC (multiple stacked injections): SFC-MS: Waters Prep 100, Column: IA 21×250 mm at 40° C., Eluent A: CO$_2$, Eluent B: MeOH, Gradient: Isocratic 90:10 CO$_2$:MeOH at 50 mL/min, Back Pressure Regulator: 120 Bars, Run Time: 12 min. Desired fractions are collected and concentrated in vacuo affording 2a4 (S-enantiomer) and 2a5 (R-enantiomer).

Step 3:

The compound 2a4 (0.52 g; 2 mmol) is dissolved in a 1:1 mixture of MeOH and THF (10 mL) and treated with an aqueous solution of LiOH (840 mg in 3 mL of water, 2 mmol). The mixture is stirred at RT for 10 min, poured into a mixture of EtOAc and saturated aqueous NaHCO$_3$ solution. The layers are separated and the aqueous layer is acidified with 6N HCl and extracted with EtOAc (3×). The organic layer is dried over MgSO$_4$, filtered and concentrated in vacuo to afford 2a6 ($t_R$=1.05 min, (M+H)$^+$ 249).

Example 3

Preparation of Intermediate 3a4

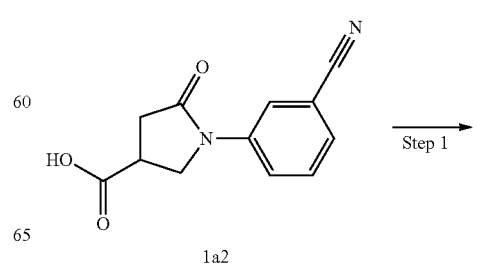

1a2

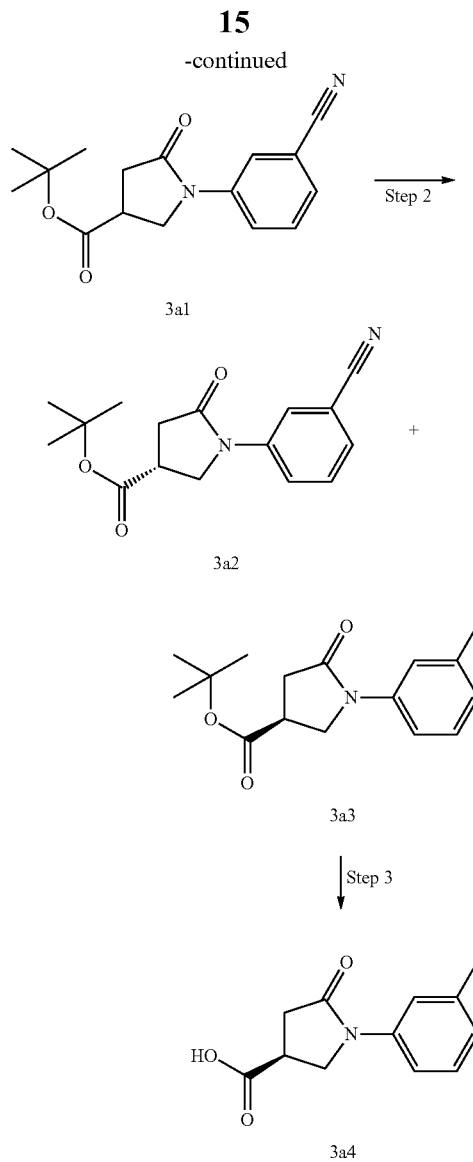

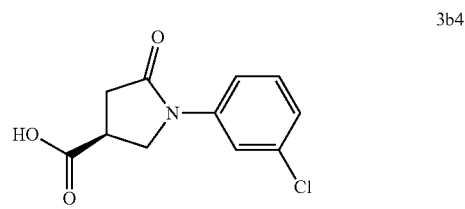 [SMILES: O=C(O)[C@H]1CC(=O)N(c2cccc(Cl)c2)C1]

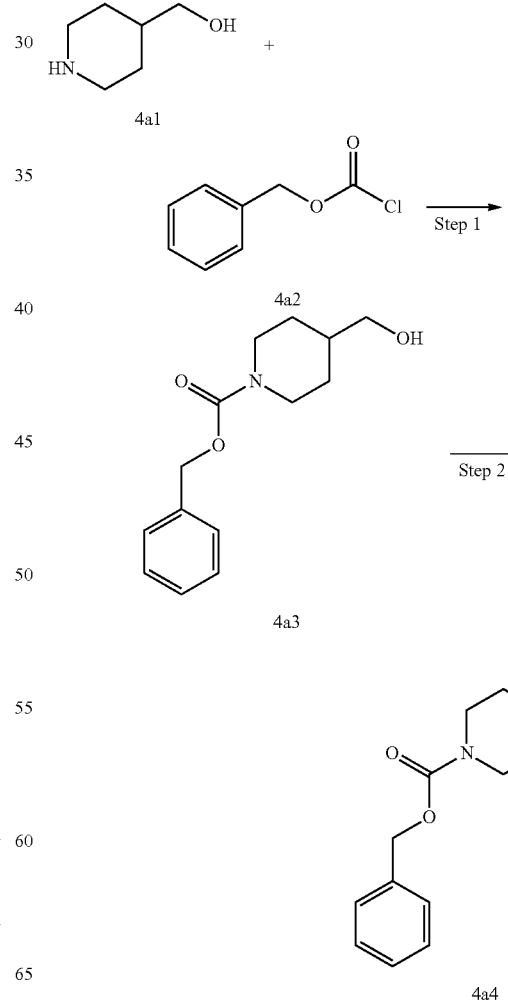

Step 3:

(S)-1-(3-cyano-phenyl)-5-oxo-pyrrolidine-3-carboxylic acid tert-butyl ester 3a3 (1.37 g; 4.8 mmol) is dissolved in DCM (25 mL) and treated with trifluoroacetic acid (25 mL, 0.32 mol). The mixture is stirred at RT for 1 h. Toluene (10 mL) is added and the solvent is evaporated. The residue is dried under high vacuum to afford 3a4 ($t_R$=0.59 min, $(M+H)^+$ 231.1).

The following intermediates are prepared analogously to the procedure described in Example 3 starting from the appropriate acid derivative.

Example 4

Preparation of Intermediate 4a4

Step 1:

To a mixture of the carboxylic acid 1a2 (5 g, 22 mmol), tert-butanol (5.7 mL, 59.5 mmol), triethylamine (6 mL, 43 mmol) and DMAP (250 mg, 2.1 mmol) in DCM (50 mL) at 0° C. is added 2,4,6-trichlorobenzoyl chloride (7 mL, 44.8 mmol). The ice bath is removed and the reaction mixture is stirred overnight at RT. The reaction mixture is poured into a mixture of water and EtOAc. The organic layer is separated and is washed with water and a saturated aqueous NaHCO$_3$ solution, dried over MgSO$_4$, filtered and concentrated in vacuo. Purification by Combi-Flash Rf (eluting 30-70% EtOAc/Hexanes) gives 3a1 ($t_R$=1.3 min, $(M+H)^+$ 287.0).

Step 2:

3a1 (4.8 g, 17 mmol) is dissolved in 96 mL of MeOH and the enantiomers are separated by SFC (multiple stacked injections): SFC-MS: Waters/Thar Prep 15, Column: IA 10×250 mm at 40° C., Eluent A: CO$_2$, Eluent B: MeOH, Gradient: Isocratic 80:20 CO$_2$:MeOH at 10 mL/min, Back Pressure Regulator: 150 Bars, Run Time: 7 min.

Desired fractions are collected and concentrated in vacuo to afford 3a2 (R-enantiomer) ($t_R$=1.31 min, $(M+H)^+$ 287.1) and 3a3 (S-enantiomer) ($t_R$=1.31 min, $(M+H)^+$ 287.1).

17

Step 1:

Piperidin-4-yl-methanol 4a1 (Lancaster, 5 g, 43 mmol) is dissolved in DCM (250 mL) and cooled to 0° C. The solution is treated with triethylamine (12 mL; 87 mmol) and dropwise addition of benzyl chloroformate 4a2 (12 mL; 87 mmol). The mixture is stirred overnight at RT. The mixture is diluted with DCM, washed with saturated aqueous NaHCO₃, water and brine, dried over MgSO₄, filtered and concentrated. Purification by Combiflash (80 g column, 50-100% EtOAc/Hex) gives 4a3.

Step 2:

Oxalyl chloride (9.4 g; 74 mmol) is dissolved in DCM (55 mL) and cooled to −78° C. DMSO (7.5 mL; 106 mmol) is added dropwise and the mixture is stirred for 15 min at −78° C. In a separate flask, 4a3 (13 g; 53 mmol) is dissolved in DCM (55 mL) and added dropwise to the first flask via cannula. Once the addition is finished, the mixture is stirred at −55° C. for 15 min. The reaction mixture is cooled to −78° C. and a solution of triethylamine (22 mL; 158 mmol) in DCM (28 mL) is added dropwise to the reaction mixture via cannula. The mixture is stirred for 1 h at −78° C. then 15 min at 0° C. and 30 min at RT. The reaction is neutralized with 11 mL of AcOH and diluted with 100 mL of DCM and 100 mL of water. The layers are separated and the aqueous layer is extracted with DCM (2×100 mL). The combined organic layers are washed with brine, dried over MgSO₄, filtered and concentrated. Purification by Combiflash (120 g column, 0-50% EtOAc/Hex) gives 4a4.

Example 5

Preparation of Intermediate 5a2

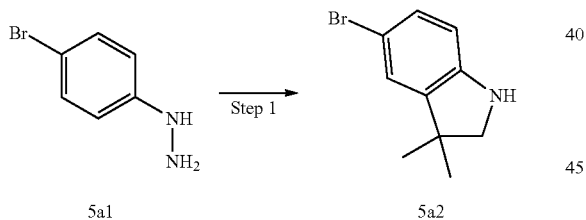

Step 1:

Hydrazine 5a1 (Matrix, 15 g, 67 mmol) is mixed with 2-methyl-propionaldehyde (Aldrich, 5.1 g, 70 mmol) and dissolved in DCM (105 mL). TFA (38 g, 340 mmol) is added to the reaction mixture and is refluxed for 1 h. Sodium borohydride (7.6 g, 201 mmol) is added to the mixture and after 10 min, the mixture is placed in an ice bath. Excess ammonium hydroxide (28% in water, 47 g, 1.3 mol) is added portionwise, followed by water (150 mL). The layers are separated and the organic layer is dried with sodium sulfate, filtered and concentrated under reduced pressure. The residue is purified by Combiflash RF (120 g column, 0-20% EtOAc:Hexanes) to give 5a2 ($t_R$=1.52 min, (M+H)⁺ 226; 228).

The following intermediates are prepared analogously to the procedure described in Example 5 starting from the appropriate hydrazine and aldehyde derivatives.

18

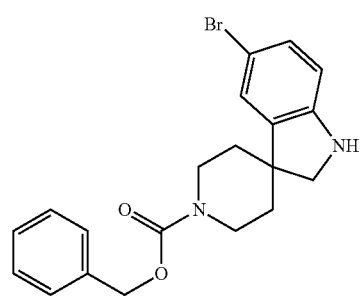
5b2

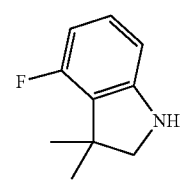
5c2

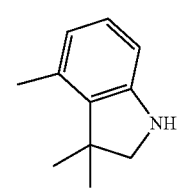
5d2

*(Mixture of 4- and 6-methyl)

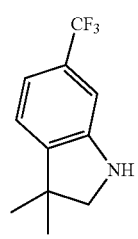
5e2

Example 6

Preparation of Intermediate 6a5

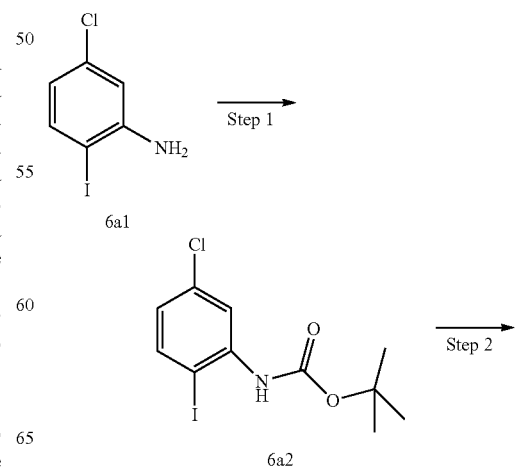

-continued

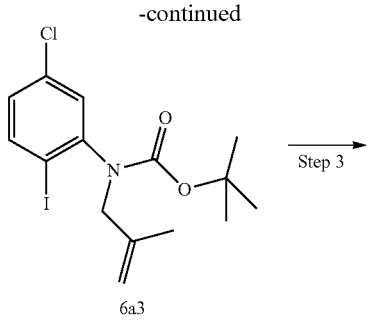

6a3

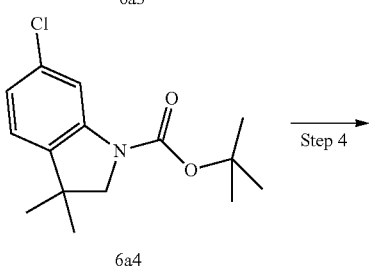

6a4

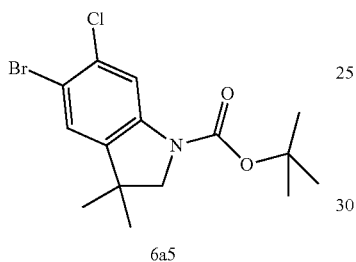

6a5

Step 1:

5-chloro-2-iodo-phenylamine 6a1 (Combi-Blocks, 15 g, 59 mmol) is dissolved in tetrahydrofuran (610 mL, 7.5 mol) and treated with boc anhydride (54 g; 250 mmol) and DMAP (720 mg, 5.9 mmol). The mixture is refluxed overnight. The reaction mixture is cooled to RT and diluted with EtOAc, washed with 1N HCl, saturated aqueous $NaHCO_3$ and brine, dried over $MgSO_4$, filtered and concentrated.

The crude bis-Boc product is taken into MeOH (609 mL, 15 mol), treated with potassium carbonate (25 g; 178 mmol) and refluxed for 2 h. The reaction mixture is cooled to RT and concentrated. The crude product is dissolved in EtOAc and water. The layers are separated and the organic layer is washed with water and brine, dried over $MgSO_4$, filtered and concentrated. Purification by Teledyne Torrent (330 g column, 0-10% EtOAc/Hex) affords 6a2 ($t_R$=1.94 min, (M–H)$^+$ 351.8; 353.8).

Step 2:

6a2 (2.5 g, 7 mmol) is dissolved in DMF (30 mL) and cooled to 0° C. NaH (60% in mineral oil, 880 mg; 27 mmol) is added. The mixture is stirred for 15 min at 0° C. and then 15 min at RT. 3-chloro-2-methyl-propene (Aldrich, 2.2 mL; 23 mmol) is added and the mixture is stirred at RT for 1.5 h. The reaction mixture is neutralized with the addition of water and EtOAc then diluted with EtOAc and water. The layers are separated and the organic layer is washed with water (4×) and brine, dried over $MgSO_4$, filtered and concentrated to afford 6a3 ($t_R$=2.12 min).

Step 3:

6a3 (2.9 g; 7 mmol) is dissolved in toluene (160 mL). Triphenyltinhydride (3 g; 8.5 mmol) is added followed by ACCN (259 mg; 1.1 mmol) and the mixture is bubbled with nitrogen for 15 min. The mixture is stirred at 80° C. for 1 h. Silica is added and the solvent is evaporated. Purification by Combiflash RF (80 g column, 0-100% toluene/Hex) gives 6a4 ($t_R$=2.07 min).

Step 4:

6a4 (1 g, 3.7 mmol) is dissolved in acetonitrile (120 mL) and 1-bromo-pyrrolidine-2,5-dione (720 mg; 4.1 mmol) is added. The mixture is stirred at RT for 45 min. The reaction mixture is concentrated to about 20 mL of MeCN, diluted with EtOAc, washed with saturated aqueous $Na_2S_2O_3$, 1N NaOH (3×) and brine, dried over $MgSO_4$, filtered and concentrated to afford 6a5 ($t_R$=2.22 min).

The following intermediates are prepared analogously to the procedure described in Example 6 starting from the appropriate aniline derivative.

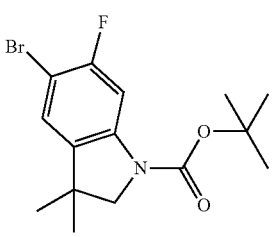

6b5

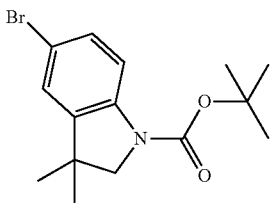

6c5

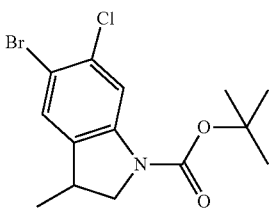

6d5

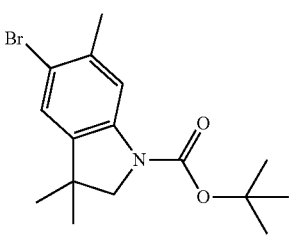

6e5

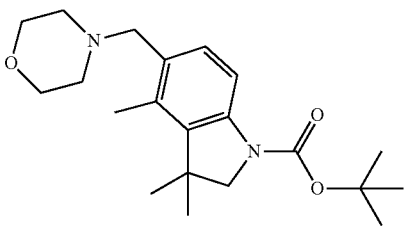

6f5

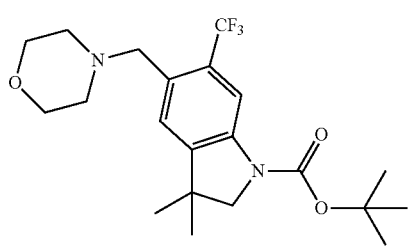

6g5

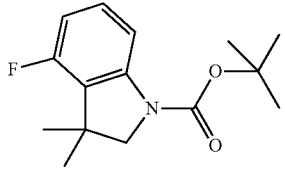

7b1

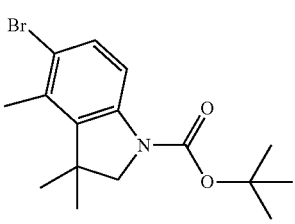

7c1

(Mixture of regioisomers)

Example 7

Preparation of Intermediate 7a1

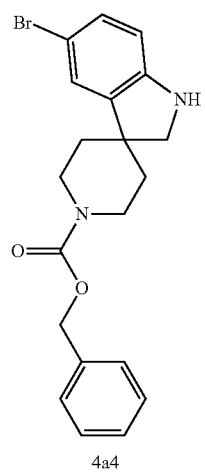

4a4

Step 1 →

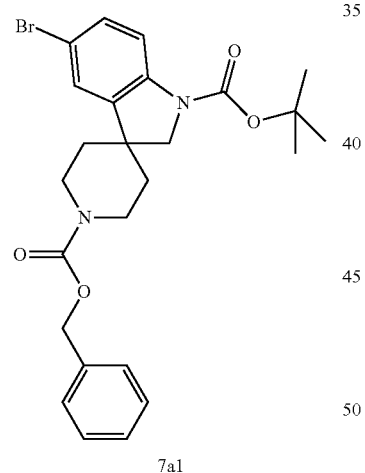

7a1

7d1

7e1

Example 8

Preparation of Intermediate 8a1

7a1

Step 1 →

Step 1:

4a4 (1 g, 2.5 mmol) is dissolved in DCM (15 mL) and treated with a solution of boc anhydride (600 mg; 2.7 mmol) in DCM (5 mL) followed by the addition of diisopropylamine (0.9 mL, 5 mmol). The mixture is stirred at RT for 2 days. The reaction mixture is diluted with EtOAc and washed with 1 N HCl. The aqueous layer is extracted with EtOAc (2×). The combined organic layers are washed with water and brine, dried over MgSO$_4$, filtered and concentrated. Purification by Combiflash RF (80 g column, 0-40% toluene/Hex) gives 7a1 ($t_R$=2.37 min, (M+H)$^+$ 501.3; 503.3).

The following intermediates are prepared analogously to the procedure described in Example 7 starting from the appropriate amine derivative.

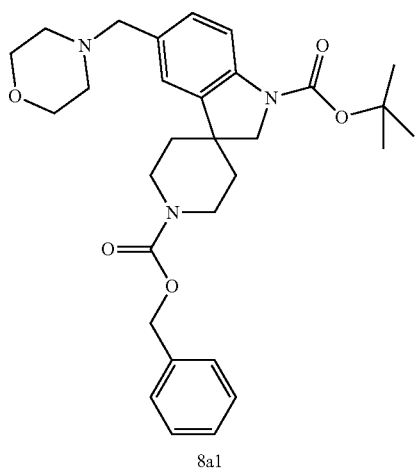

8a1

Step 1:

A pressure vessel equipped with a Teflon stir bar is charged with 7a1 (700 mg; 1.4 mmol), potassium (morpholin-4-yl)methyltrifluoroborate (350 mg, 1.7 mmol), cesium carbonate (1.4 g; 4.2 mmol), palladium (II) acetate (31 mg; 0.14 mmol) and 2-dicyclohexylphosphino-2',4',6'-tri-i-propyl-1,1'-biphenyl (130 mg; 0.28 mmol). Tetrahydrofuran (7 mL) and water (0.7 mL) are added and the solution is degassed by bubbling argon for 5 min. The vessel is sealed and heated at 80° C. overnight. The reaction mixture is cooled to RT, filtered over Celite and washed with EtOAc. Water is added and the aqueous layer is extracted with EtOAc (3×). The combined organic layers are washed with brine, dried over MgSO$_4$, filtered and concentrated. Purification by Combiflash RF (25 g column, 70-100% EtOAc/Hex) gives 8a1 (t$_R$=1.88 min, (M+H)$^+$ 522.2).

The following intermediates are prepared analogously to the procedure described in Example 8 starting from the appropriate bromoindoline derivative.

8b1

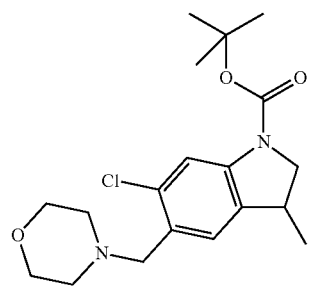 [SMILES: CC1CN(C(=O)OC(C)(C)C)c2cc(Cl)c(CN3CCOCC3)cc21]

8c1

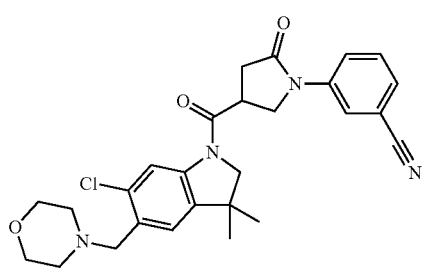 [SMILES: CC1(C)CN(C(=O)C2CC(=O)N(c3cccc(C#N)c3)C2)c2cc(Cl)c(CN3CCOCC3)cc21]

8d1

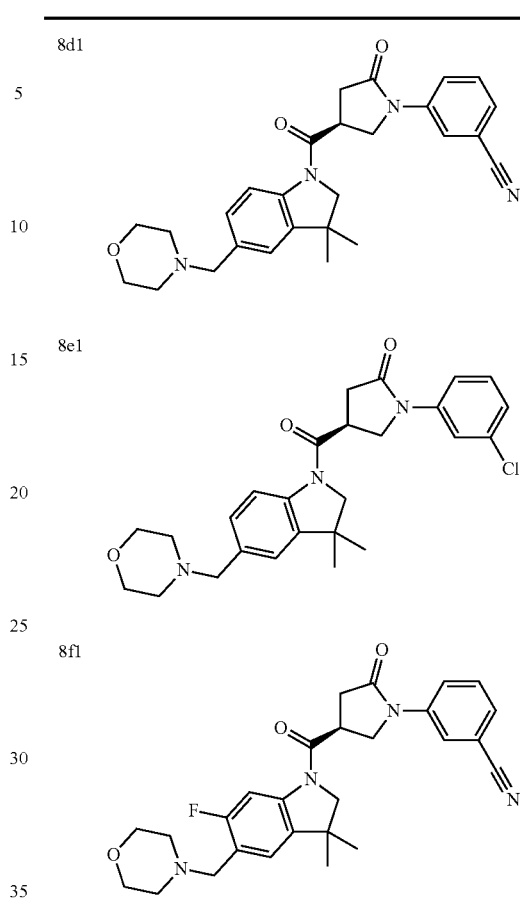

8e1

8f1

8g1

8h1

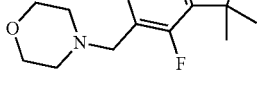
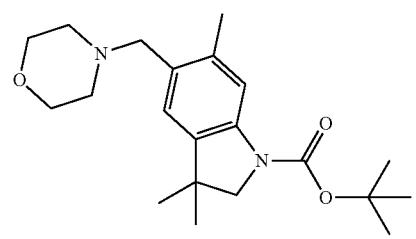 [SMILES: Cc1cc2c(cc1CN1CCOCC1)C(C)(C)CN2C(=O)OC(C)(C)C]

8i1

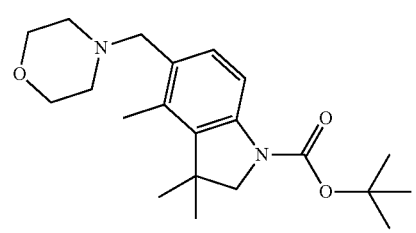 [SMILES: Cc1c(CN2CCOCC2)ccc2c1C(C)(C)CN2C(=O)OC(C)(C)C]

-continued
| | | |
|---|---|---|
| 8j1 | 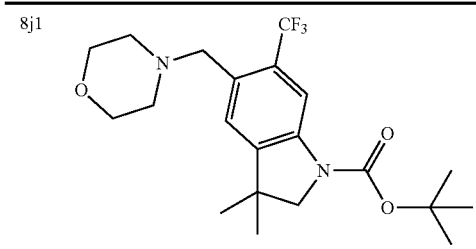 | |
| 8k1 | 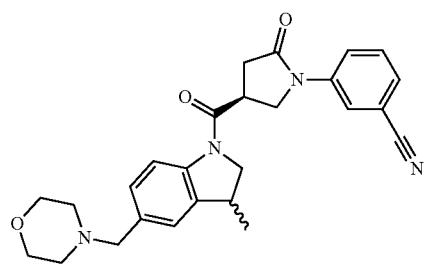 [SMILES: CC1CN(C(=O)[C@H]2CC(=O)N(c3cccc(C#N)c3)C2)c2ccc(CN3CCOCC3)cc21] | |
| 8l1 | 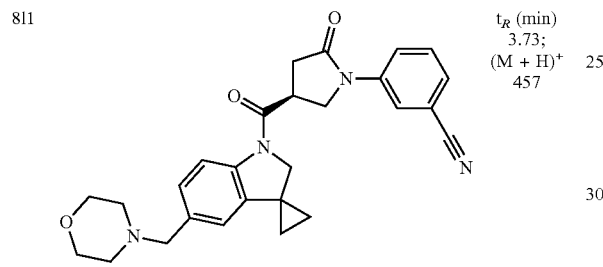 | $t_R$ (min) 3.73; $(M + H)^+$ 457 |
| 8l2 | 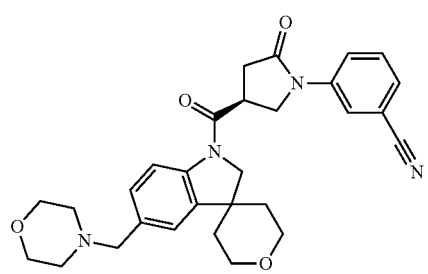 [SMILES: N#Cc1cccc(N2C[C@@H](C(=O)N3CC4(CCOCC4)c4cc(CN5CCOCC5)ccc43)CC2=O)c1] | |
| 8m1 | 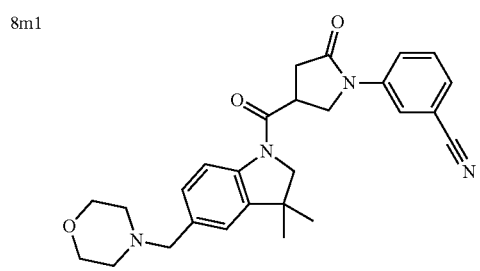 | |
| 8n1 | 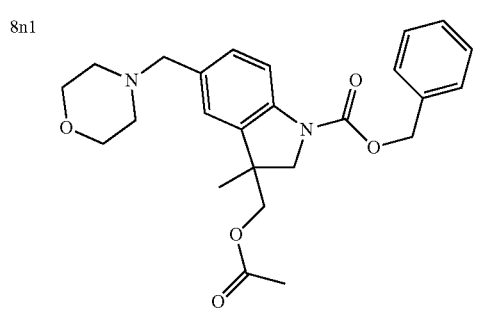 | |
-continued
| | |
|---|---|
| 8o1 | 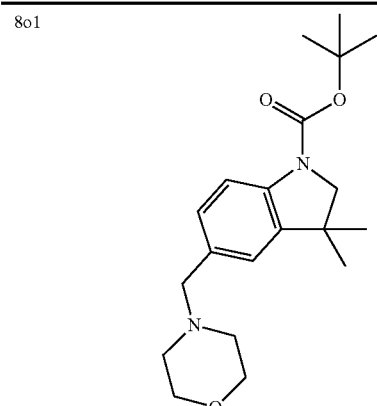 |
Example 9
Preparation of Intermediate 9a2
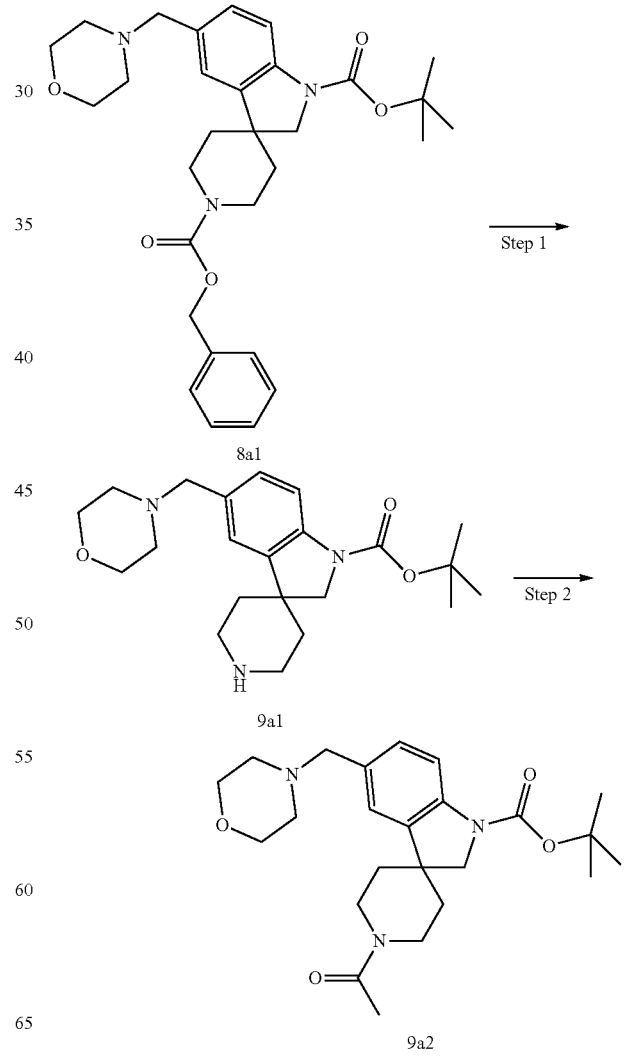

Step 1:

8a1 (600 mg, 1.1 mmol) is dissolved in EtOH (12 mL) and purged under argon. Pd/C (10% w/w, 182 mg, 0.2 mmol) is added. The mixture is purged under argon and then placed under H$_2$ (1 atm) for 2 h. The reaction mixture is filtered through a pad of celite and washed with MeOH. The filtrate is concentrated to dryness to afford 9a1 (t$_R$=0.95 min, (M+H)$^+$ 388.3).

Step 2:

9a1 (430 mg, 1.1 mmol) is dissolved in DCM (44 mL) and treated with acetyl chloride (94 μL, 1.3 mmol) followed by triethylamine (0.31 mL, 2.2 mmol).

The mixture is stirred at RT for 16 h. Water and DCM are added and the layers are separated. The aqueous layer is extracted with DCM (3×). The combined organic layers are washed with water, brine, dried over MgSO$_4$, filtered and concentrated to afford 9a2 (t$_R$=1.34 min, (M+H)$^+$ 430.3).

Example 10

Preparation of Intermediate 10a1

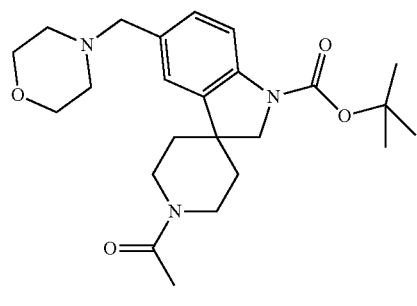

9a2

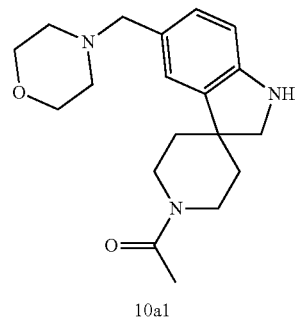

10a1

Step 1:

9a2 (50 mg, 0.1 mmol) is treated with a solution of HCl in 1,4-dioxane (4M, 1 mL, 4 mmol) at RT for 2 h. The mixture is concentrated to dryness to afford 10a1 (t$_R$=0.95 min, (M+H)$^+$ 388.3).

The following intermediates are prepared analogously to the procedure described in Example 10 starting from the appropriate BOC derivative.

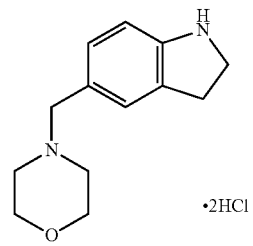

10b1

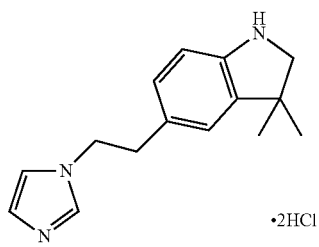

10c1

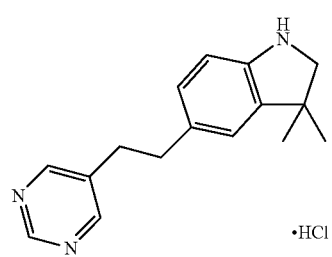

10d1

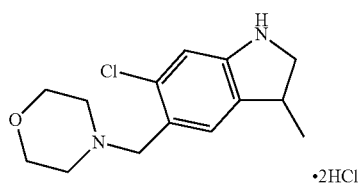

10e1

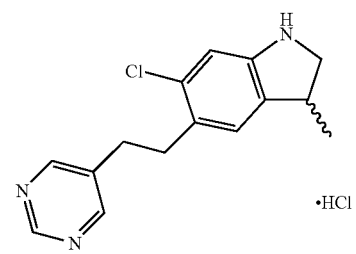

10f1

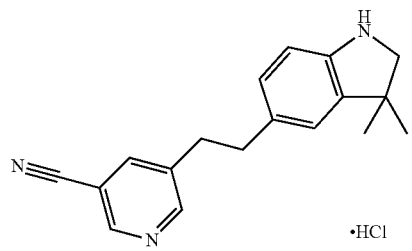

10g1

10h1 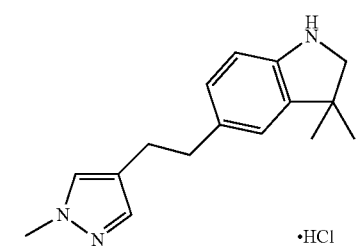
10i1 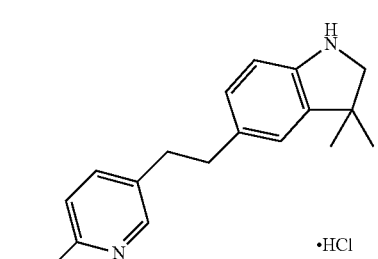
10j1 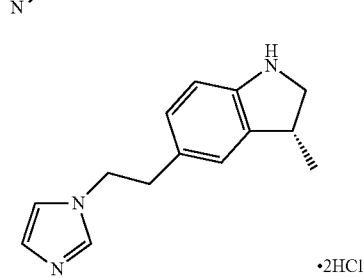
10k1 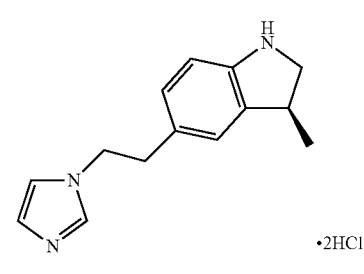
10l1 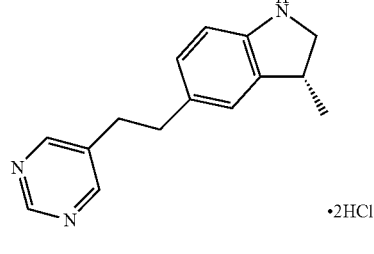
10m1 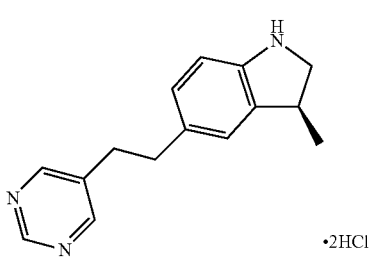
10n1 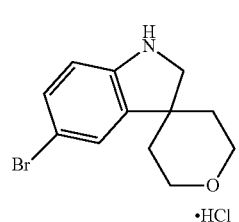
10o1 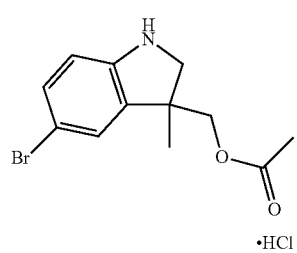
10p1 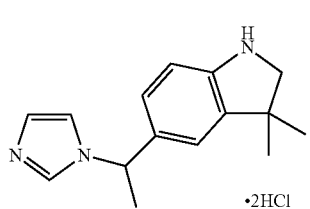
10q1 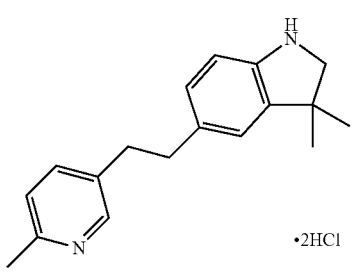
10r1 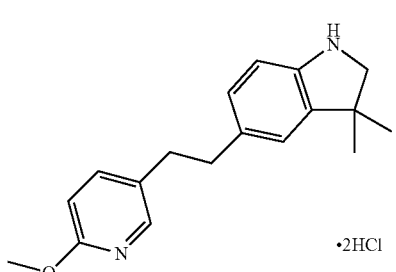
10s1 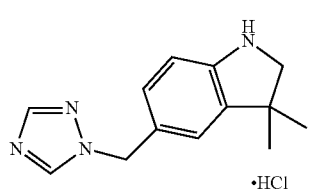
10t1 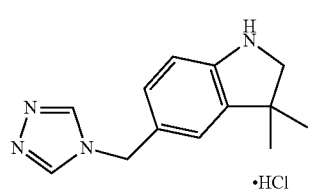

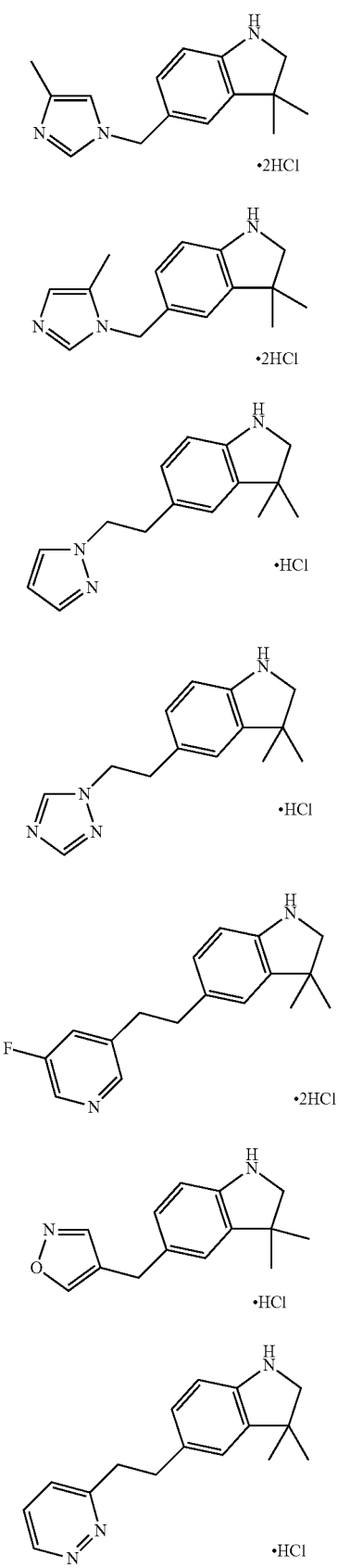

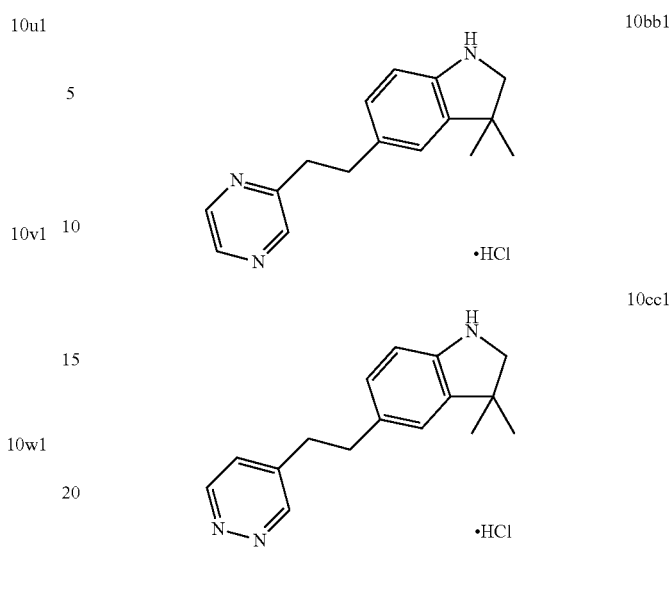

Example 10-1

Preparation of Intermediate 10-1a1

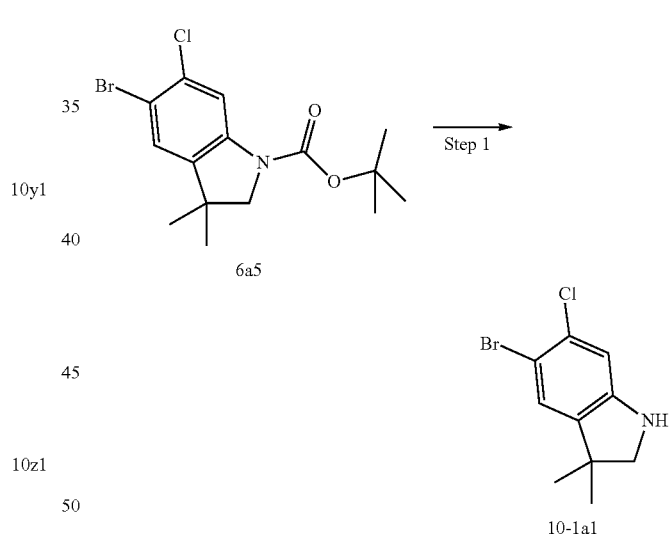

Step 1:

6a5 (1.1 g; 3.1 mmol) is dissolved in DCM (15 mL) and the solution is treated by dropwise addition of trifluoroacetic acid (15 mL). The mixture is stirred for 30 min and the solvent is evaporated. The crude product is taken in DCM (75 mL). A saturated aqueous NaHCO$_3$ solution is added and the mixture is stirred for 1 h. The layers are separated and the aqueous layer is extracted twice with DCM. The combined organic layers are dried over MgSO$_4$, filtered and concentrated to afford 10-1a1 ($t_R$=1.71 min, (M–H)$^+$ 260; 261.9).

The following intermediates are prepared analogously to the procedure described in Example 10-1 starting from the appropriate BOC derivative

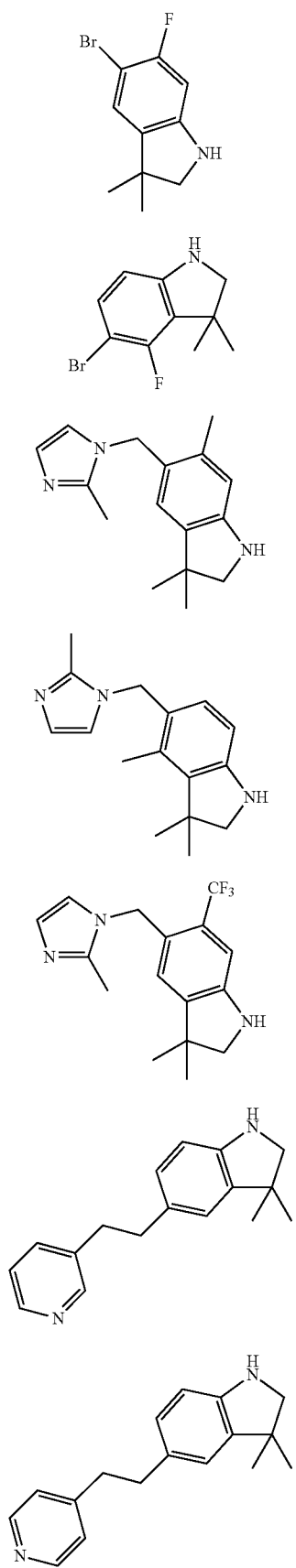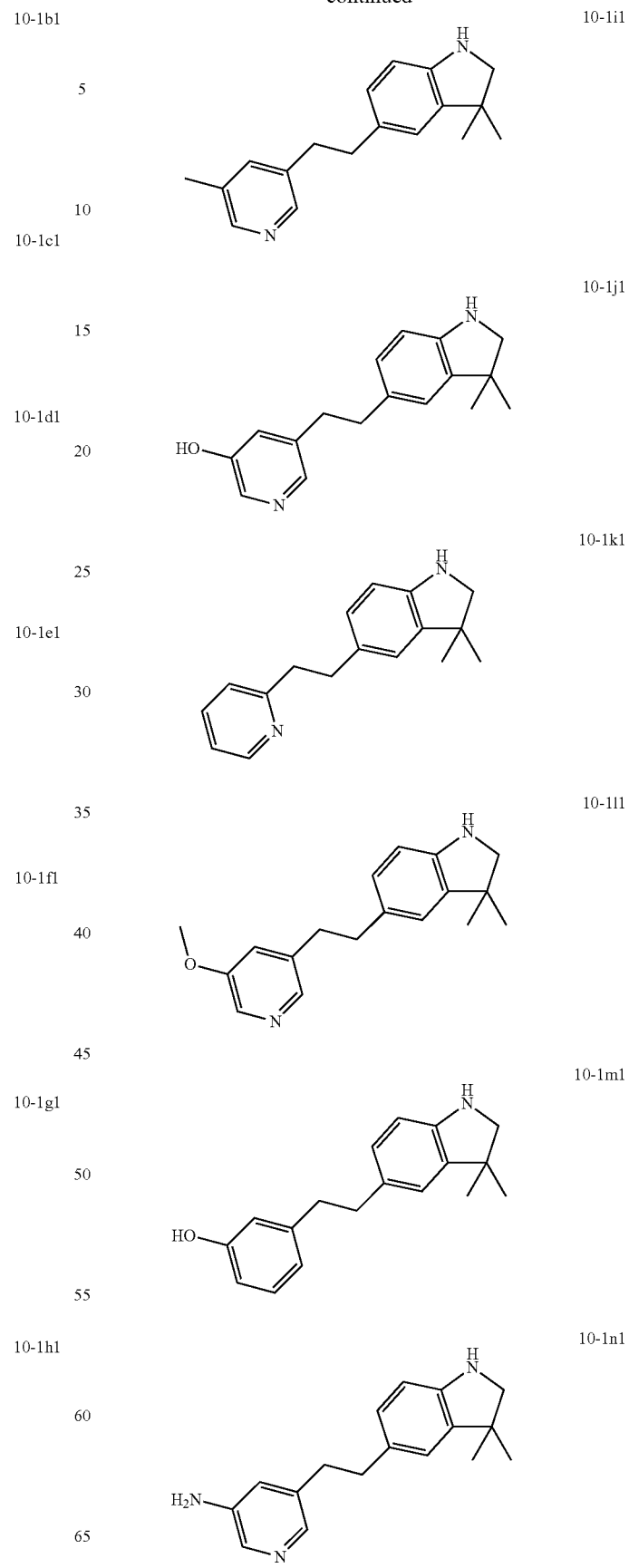

Example 11

Preparation of 11a1

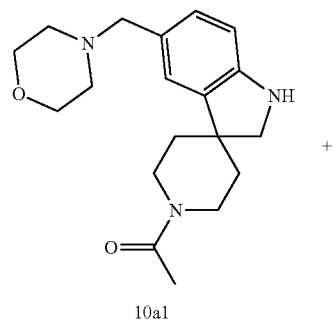

10a1

+

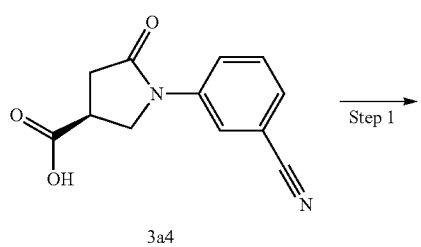

3a4

→ Step 1

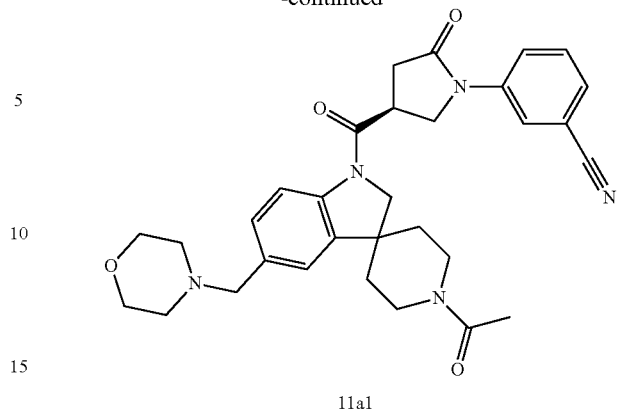

11a1

Step 1:
To the acid 3a4 (24 mg, 0.11 mmol) in NMP (1 mL) is added HATU (80 mg, 0.2 mmol) and 2,6-lutidine (73 μL, 0.63 mmol). A solution of the amine 10a1 (42 mg, 0.12 mmol) in NMP (0.25 mL) is added and the mixture is stirred at RT for 2.5 h.

The reaction mixture is diluted with AcOH/MeOH (to provide 2 mL of solution), filtered through an Acrodisc filter and purified by preparative-HPLC MeOH/H$_2$O (containing 5 mM of ammonium formate). The pure fractions are combined, concentrated, diluted with a mixture of MeCN/H$_2$O, frozen and lyophilized to afford 11a1 (t$_R$=1.07 min, (M+H)$^+$ 542.5).

The following compounds are prepared analogously to the procedure described in Example 11 starting from the appropriate acid and indoline derivative.

11b1

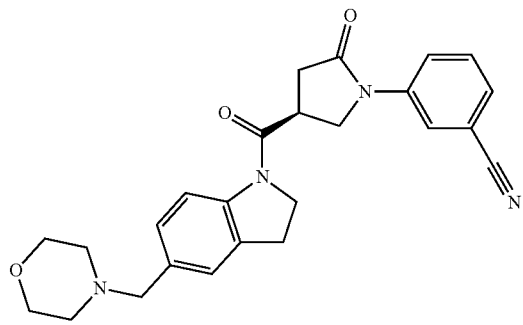 [SMILES: N#Cc1cccc(N2C[C@@H](C(=O)N3CCc4cc(CN5CCOCC5)ccc43)CC2=O)c1]

11c1

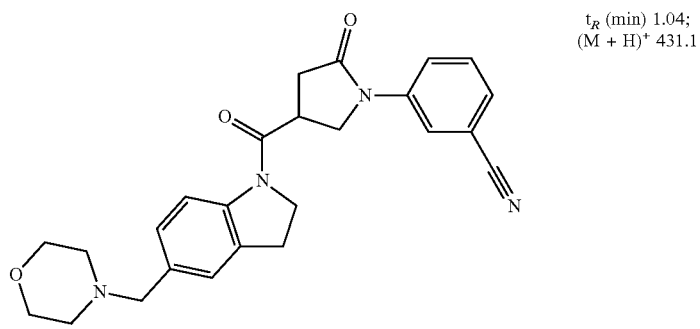

t$_R$ (min) 1.04; (M + H)$^+$ 431.1

| | | |
|---|---|---|
| 11d1 | 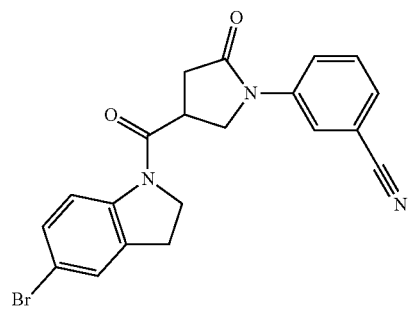 [SMILES: N#Cc1cccc(N2CC(C(=O)N3CCc4cc(Br)ccc43)CC2=O)c1] | |
| 11e1 | 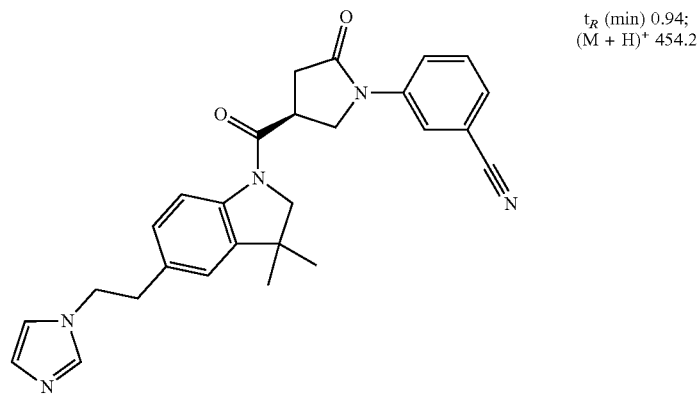 | $t_R$ (min) 0.94; $(M + H)^+$ 454.2 |
| 11f1 | 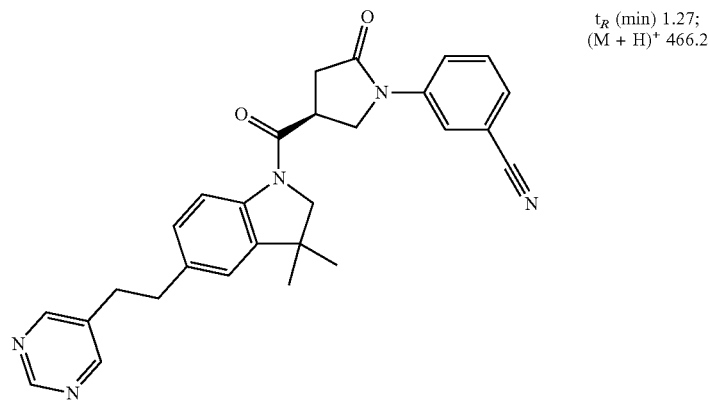 | $t_R$ (min) 1.27; $(M + H)^+$ 466.2 |
| 11g1 | 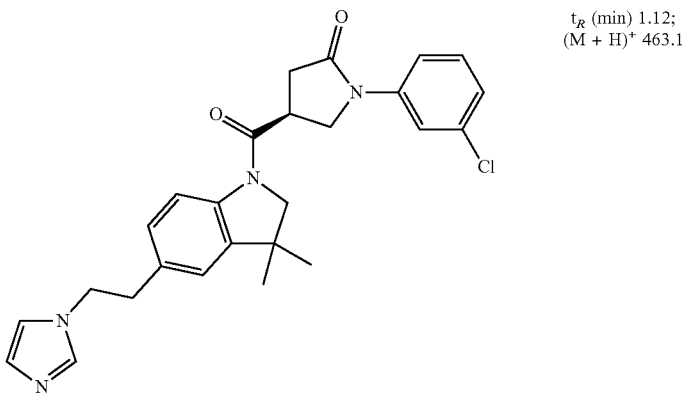 | $t_R$ (min) 1.12; $(M + H)^+$ 463.1 |

| | | |
|---|---|---|
| 11h1 | 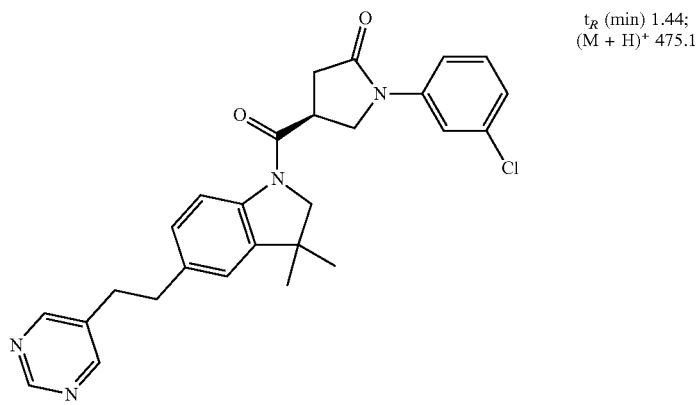 | $t_R$ (min) 1.44; (M + H)+ 475.1 |
| 11i1 | 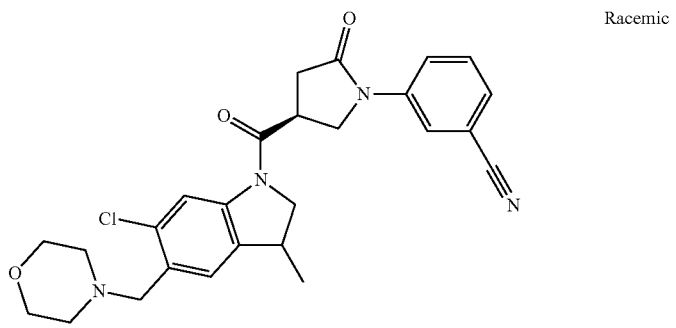 | Racemic |
| 11j1 | 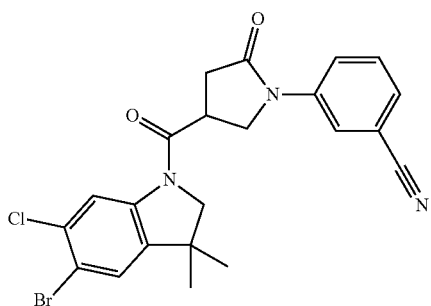 [SMILES: CC1(C)CN(C(=O)C2CC(=O)N(c3cccc(C#N)c3)C2)c2cc(Cl)c(Br)cc21] | |
| 11k1 | 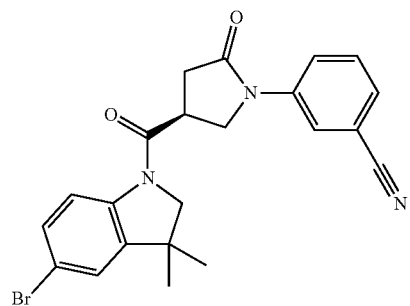 [SMILES: CC1(C)CN(C(=O)[C@H]2CC(=O)N(c3cccc(C#N)c3)C2)c2ccc(Br)cc21] | |

| | | |
|---|---|---|
| 11l1 | 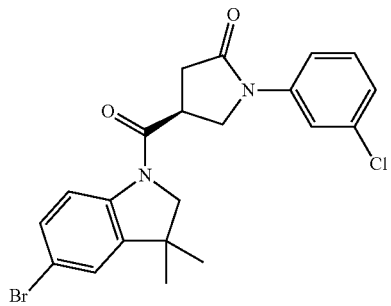 [SMILES: CC1(C)CN(C(=O)[C@H]2CC(=O)N(c3cccc(Cl)c3)C2)c2ccc(Br)cc21] | |
| 11m1 | 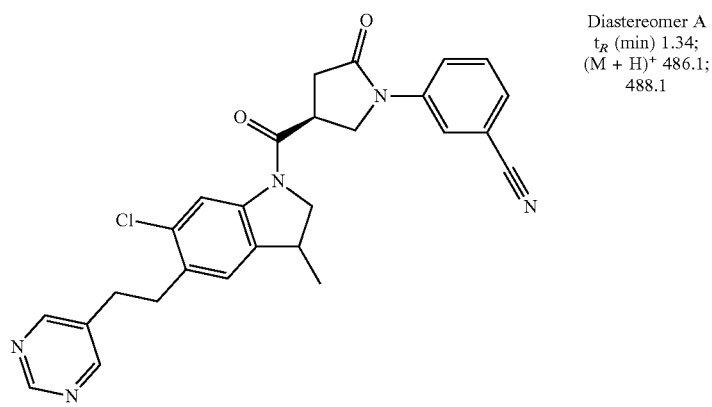 | Diastereomer A<br>$t_R$ (min) 1.34;<br>$(M + H)^+$ 486.1;<br>488.1 |
| 11n1 | 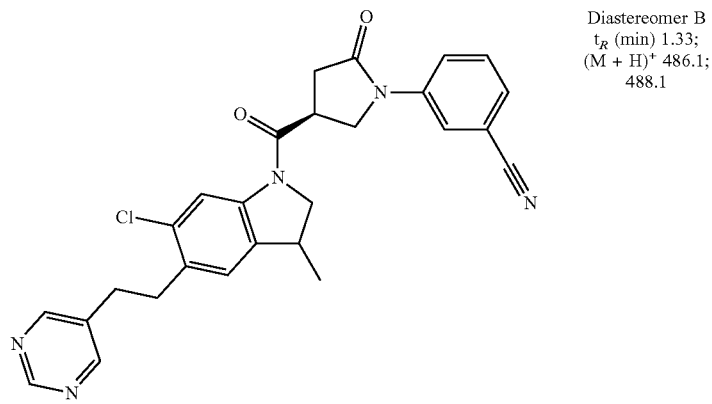 | Diastereomer B<br>$t_R$ (min) 1.33;<br>$(M + H)^+$ 486.1;<br>488.1 |
| 11o1 | 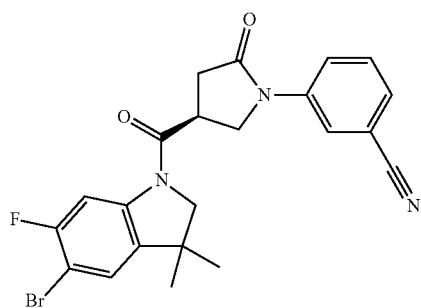 [SMILES: CC1(C)CN(C(=O)[C@H]2CC(=O)N(c3cccc(C#N)c3)C2)c2cc(F)c(Br)cc21] | |

| | | |
|---|---|---|
| 11p1 | 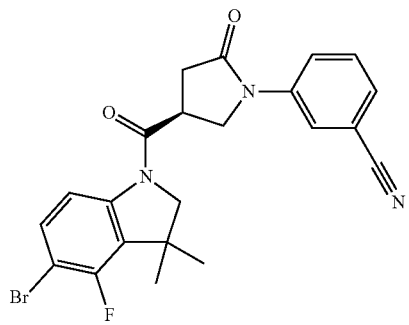 [SMILES: CC1(C)CN(C(=O)[C@H]2CC(=O)N(c3cccc(C#N)c3)C2)c2ccc(Br)c(F)c21] | |
| 11q1 | 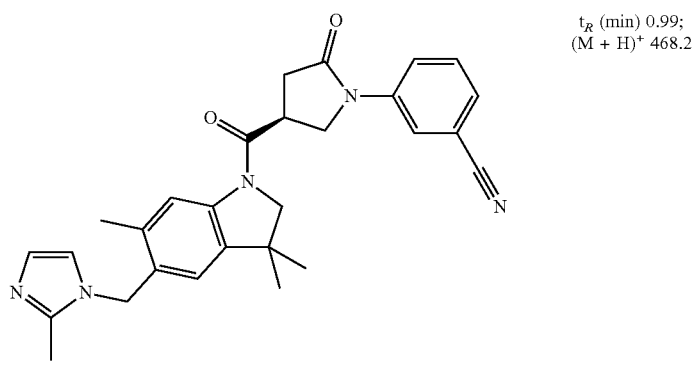 | $t_R$ (min) 0.99; $(M + H)^+$ 468.2 |
| 11r1 | 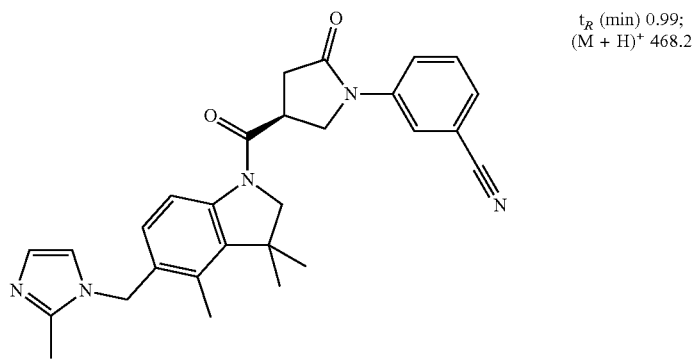 | $t_R$ (min) 0.99; $(M + H)^+$ 468.2 |
| 11s1 | 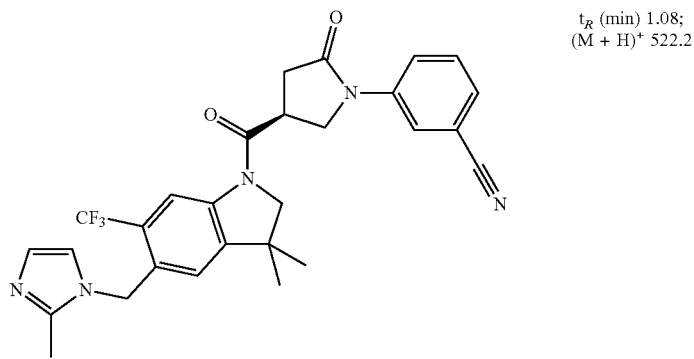 | $t_R$ (min) 1.08; $(M + H)^+$ 522.2 |

| | | |
|---|---|---|
| 11t1 | 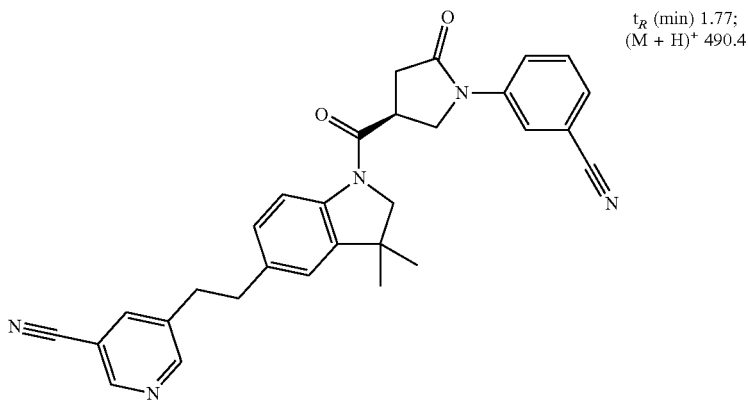 | $t_R$ (min) 1.77; (M + H)$^+$ 490.4 |
| 11u1 | 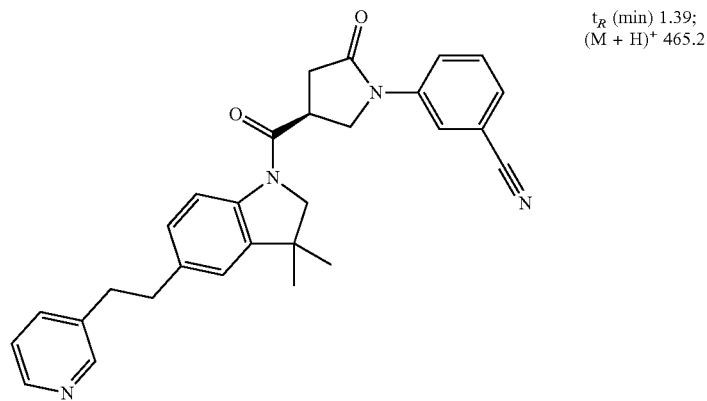 | $t_R$ (min) 1.39; (M + H)$^+$ 465.2 |
| 11v1 | 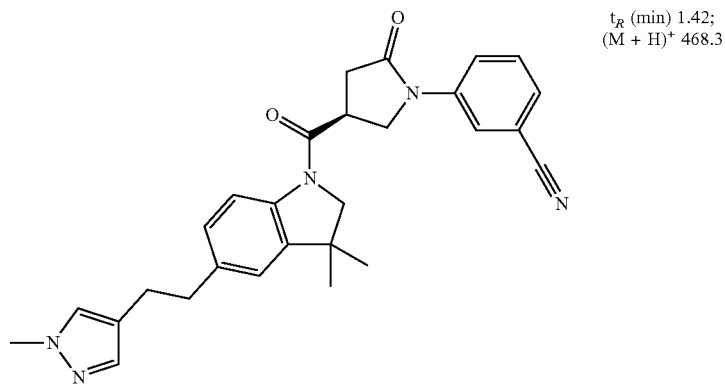 | $t_R$ (min) 1.42; (M + H)$^+$ 468.3 |
| 11w1 | 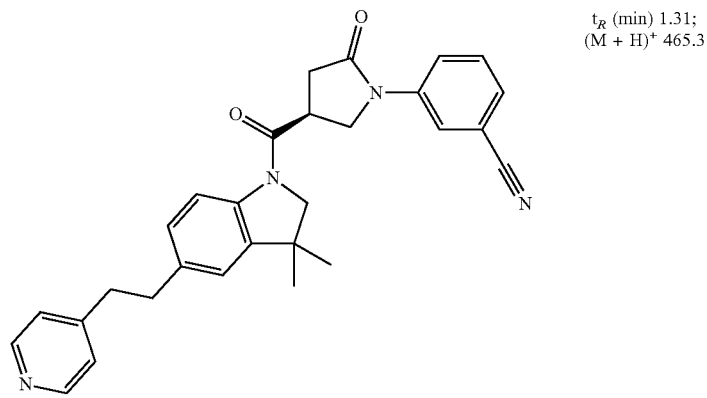 | $t_R$ (min) 1.31; (M + H)$^+$ 465.3 |

| | | |
|---|---|---|
| 11x1 | 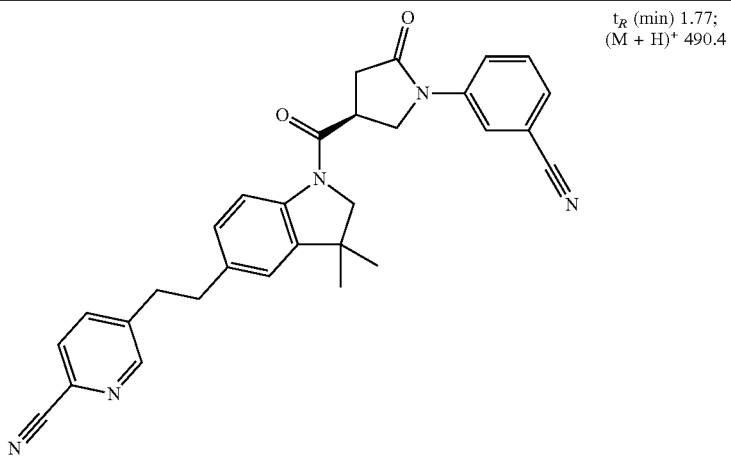 | $t_R$ (min) 1.77; $(M + H)^+$ 490.4 |
| 11y1 | 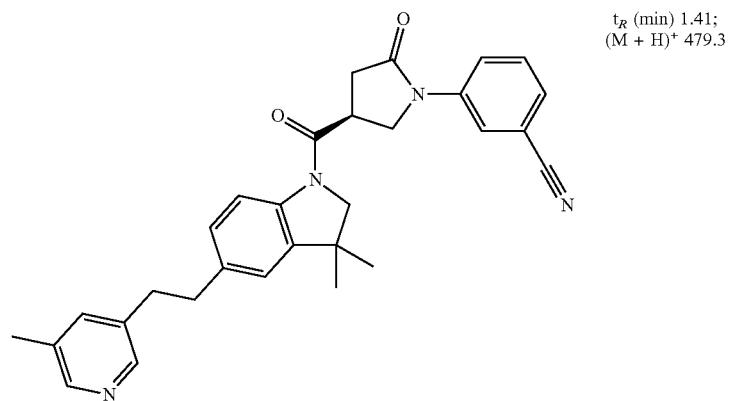 | $t_R$ (min) 1.41; $(M + H)^+$ 479.3 |
| 11z1 | 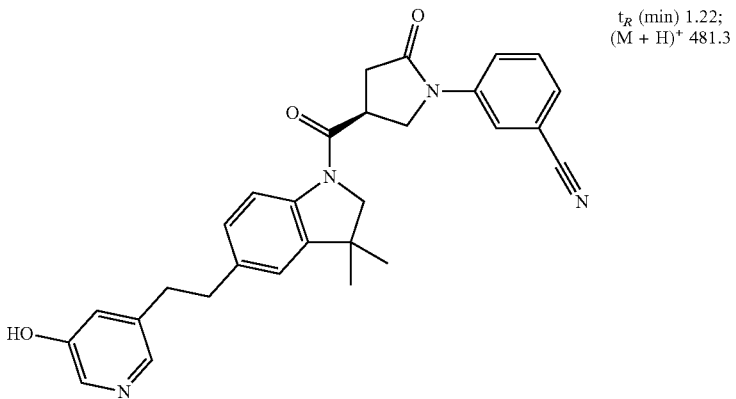 | $t_R$ (min) 1.22; $(M + H)^+$ 481.3 |
| 11aa1 | 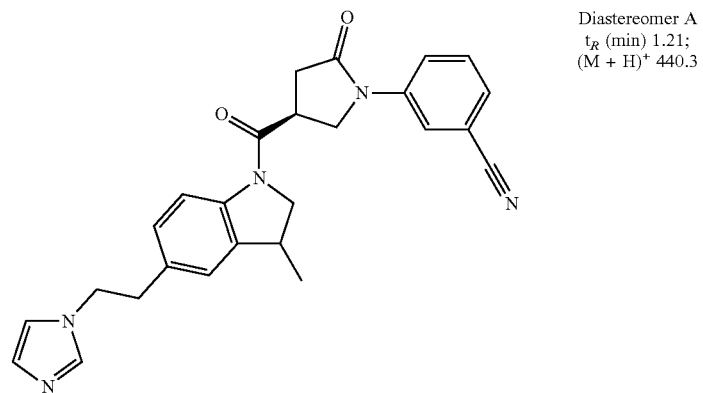 | Diastereomer A $t_R$ (min) 1.21; $(M + H)^+$ 440.3 |

| | | |
|---|---|---|
| 11bb1 | 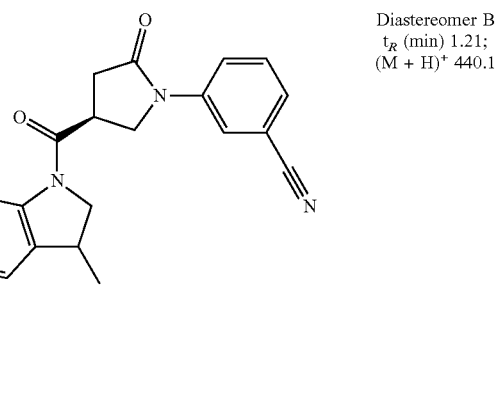 | Diastereomer B<br>$t_R$ (min) 1.21;<br>$(M + H)^+$ 440.1 |
| 11cc1 | 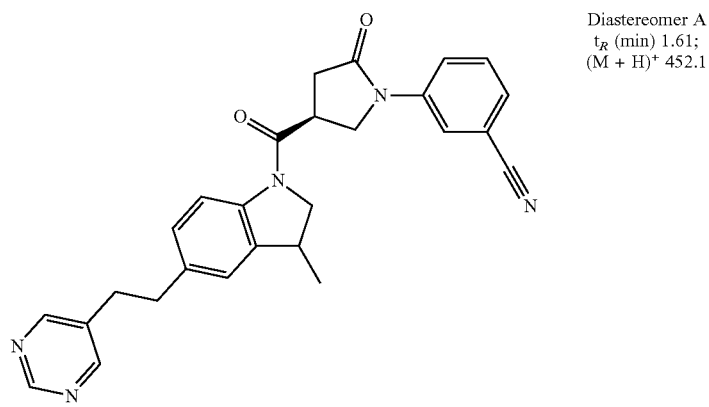 | Diastereomer A<br>$t_R$ (min) 1.61;<br>$(M + H)^+$ 452.1 |
| 11dd1 | 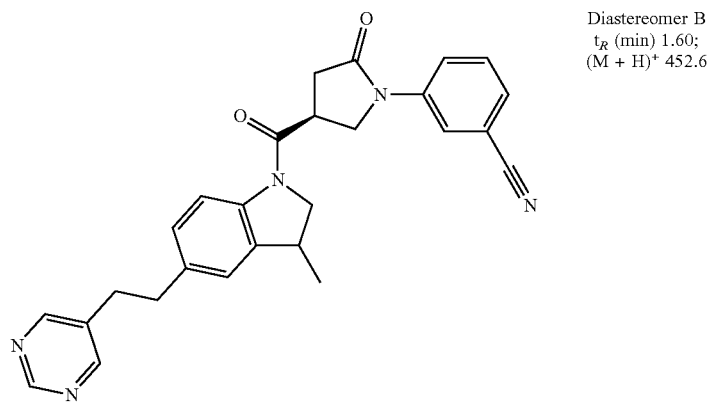 | Diastereomer B<br>$t_R$ (min) 1.60;<br>$(M + H)^+$ 452.6 |
| 11ee1 | 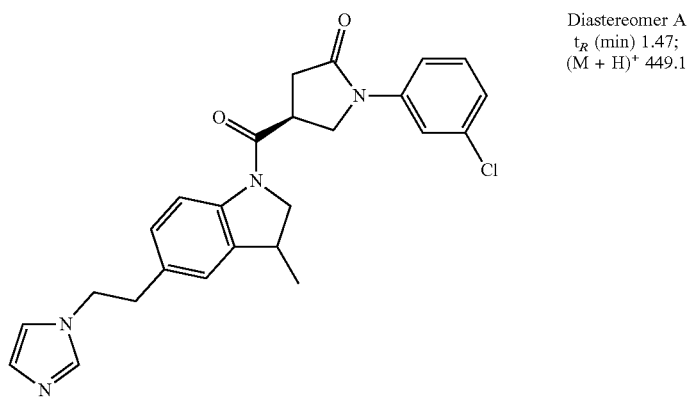 | Diastereomer A<br>$t_R$ (min) 1.47;<br>$(M + H)^+$ 449.1 |

| | | |
|---|---|---|
| 11ff1 | 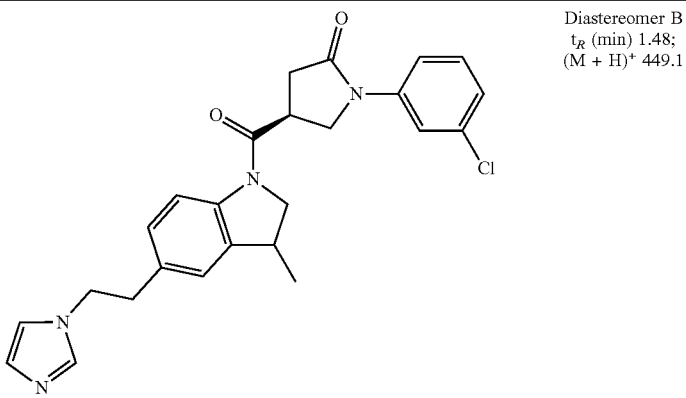 | Diastereomer B<br>$t_R$ (min) 1.48;<br>$(M + H)^+$ 449.1 |
| 11gg1 | 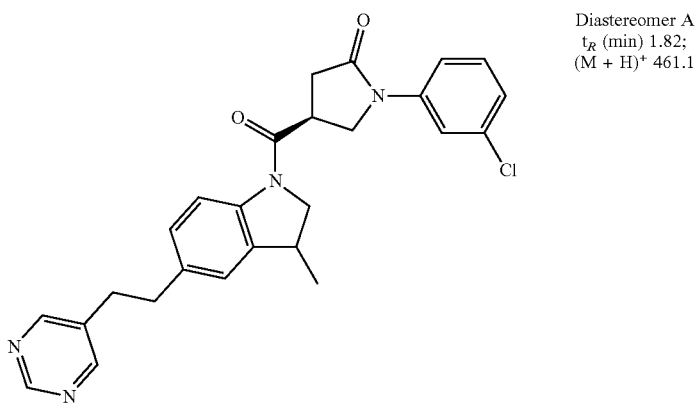 | Diastereomer A<br>$t_R$ (min) 1.82;<br>$(M + H)^+$ 461.1 |
| 11hh1 | 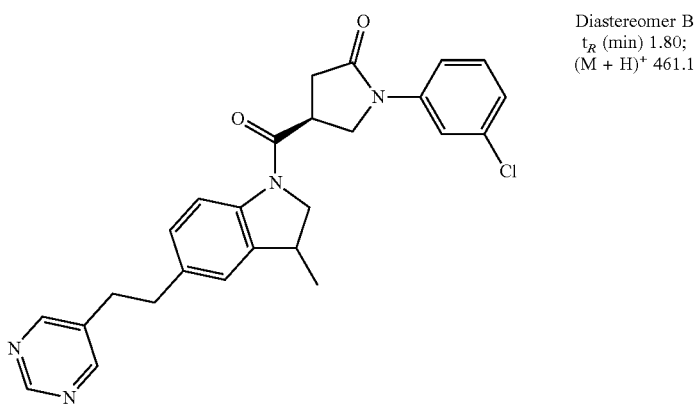 | Diastereomer B<br>$t_R$ (min) 1.80;<br>$(M + H)^+$ 461.1 |
| 11ii1 | 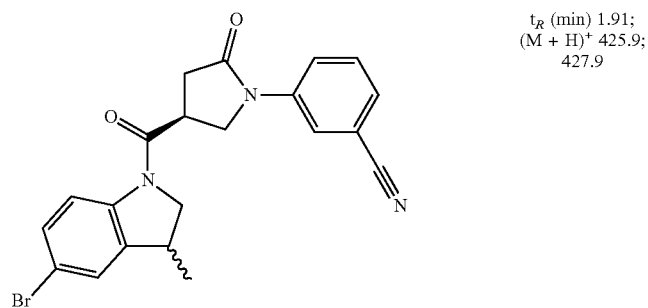 | $t_R$ (min) 1.91;<br>$(M + H)^+$ 425.9;<br>427.9 |

11jj1 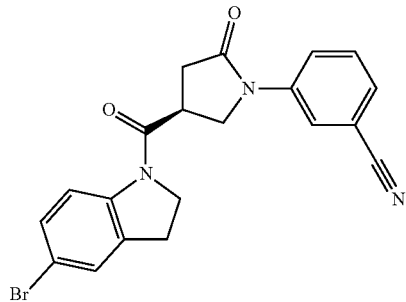 [SMILES: N#Cc1cccc(N2C[C@@H](C(=O)N3CCc4cc(Br)ccc43)CC2=O)c1]
11kk1 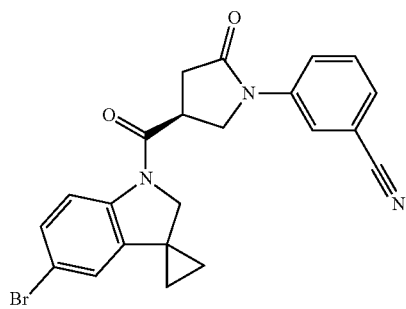 [SMILES: N#Cc1cccc(N2C[C@@H](C(=O)N3CC4(CC4)c4cc(Br)ccc43)CC2=O)c1]
11ll1 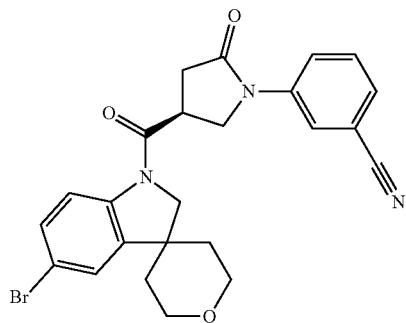 [SMILES: N#Cc1cccc(N2C[C@@H](C(=O)N3CC4(CCOCC4)c4cc(Br)ccc43)CC2=O)c1]
11mm1 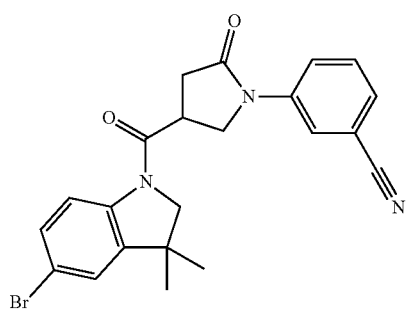 [SMILES: CC1(C)CN(C(=O)C2CC(=O)N(c3cccc(C#N)c3)C2)c2ccc(Br)cc21]
11nn1 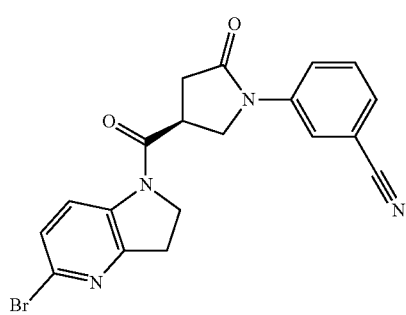 [SMILES: N#Cc1cccc(N2C[C@@H](C(=O)N3CCc4nc(Br)ccc43)CC2=O)c1]

| | | |
|---|---|---|
| 11oo1 | 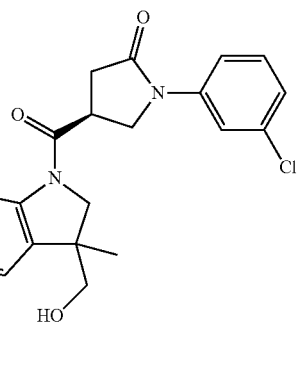 | $t_R$ (min) 0.94; (M + H)+ 493.2; 495.2 Single diastereomer |
| 11pp1 | 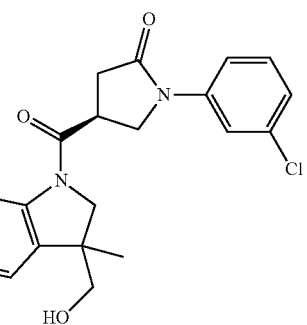 | Diastereomer A $t_R$ (min) 1.24; (M + H)+ 480.1; 482.1 |
| 11qq1 | 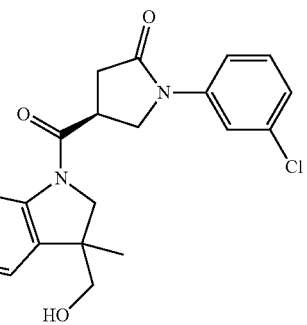 | Diastereomer B $t_R$ (min) 1.29; (M + H)+ 480.1; 482.1 |
| 11rr1 | 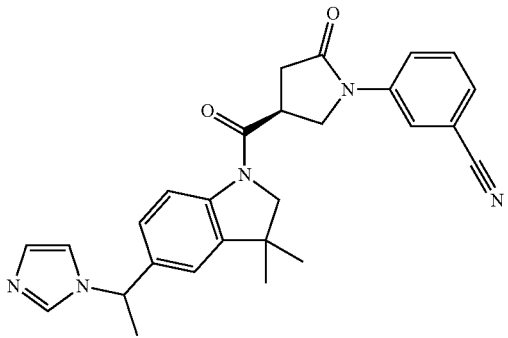 [SMILES: CC(c1ccc2c(c1)C(C)(C)CN2C(=O)[C@H]1CC(=O)N(c2cccc(C#N)c2)C1)n1ccnc1] | $t_R$ (min) 1.25; (M + H)+ 454.4 Racemic |

-continued
| | | |
|---|---|---|
| 11ss1 | 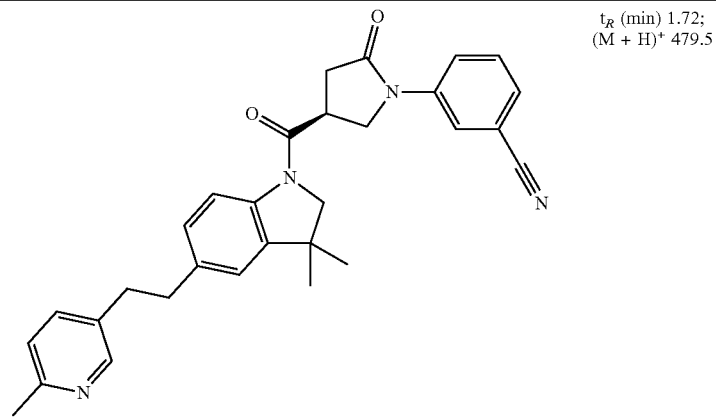 | $t_R$ (min) 1.72; $(M + H)^+$ 479.5 |
| 11tt1 | 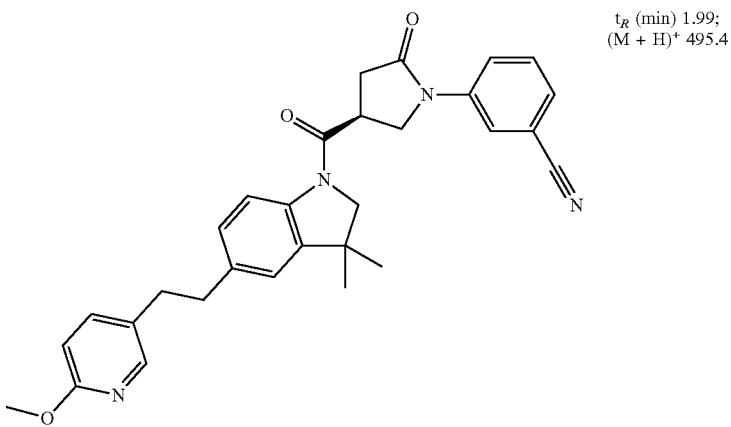 | $t_R$ (min) 1.99; $(M + H)^+$ 495.4 |
| 11uu1 | 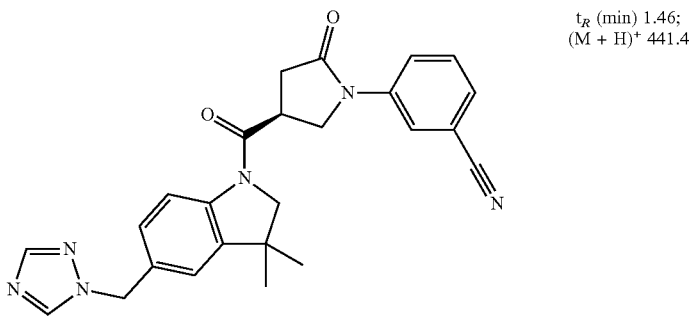 | $t_R$ (min) 1.46; $(M + H)^+$ 441.4 |
| 11vv1 | 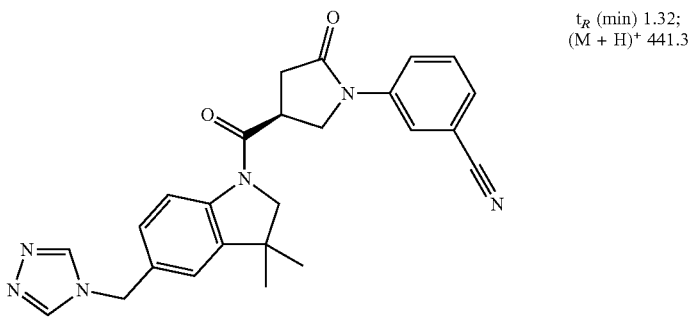 | $t_R$ (min) 1.32; $(M + H)^+$ 441.3 |

| | | |
|---|---|---|
| 11ww1 | 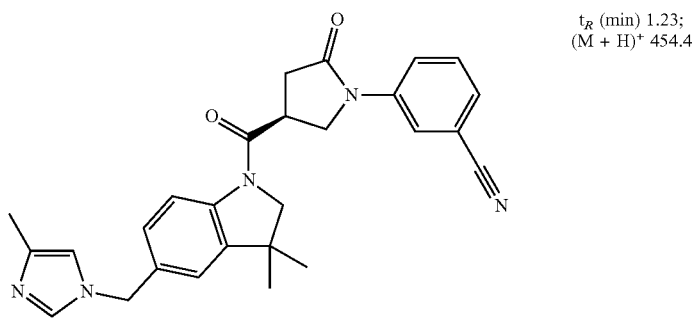 | t_R (min) 1.23; (M + H)+ 454.4 |
| 11xx1 | 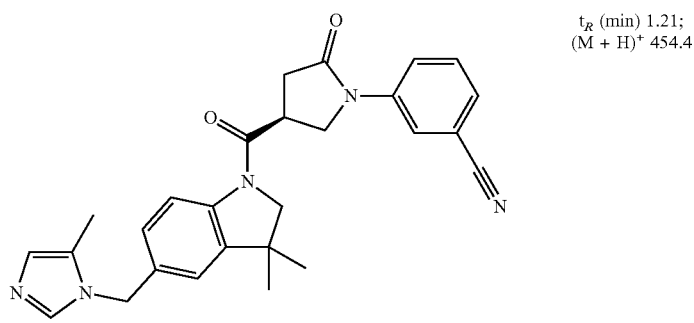 | t_R (min) 1.21; (M + H)+ 454.4 |
| 11yy1 | 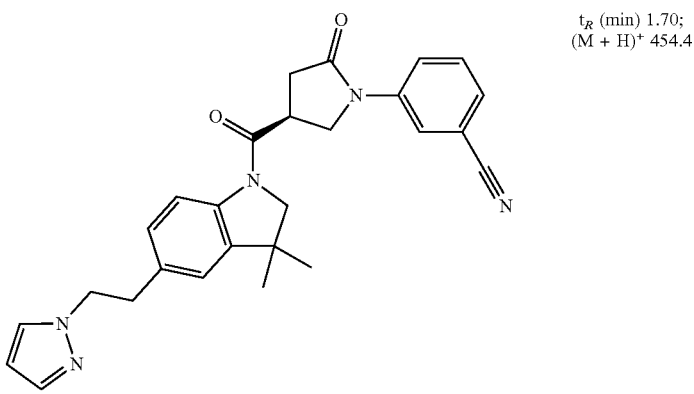 | t_R (min) 1.70; (M + H)+ 454.4 |
| 11zz1 | 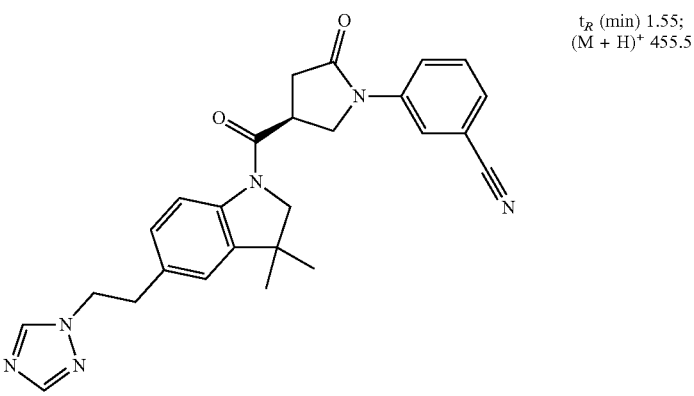 | t_R (min) 1.55; (M + H)+ 455.5 |

-continued
11aaa1 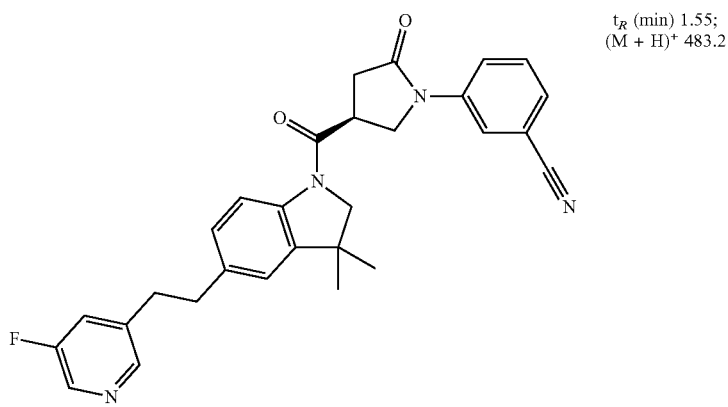 $t_R$ (min) 1.55; $(M + H)^+$ 483.2
11bbb1 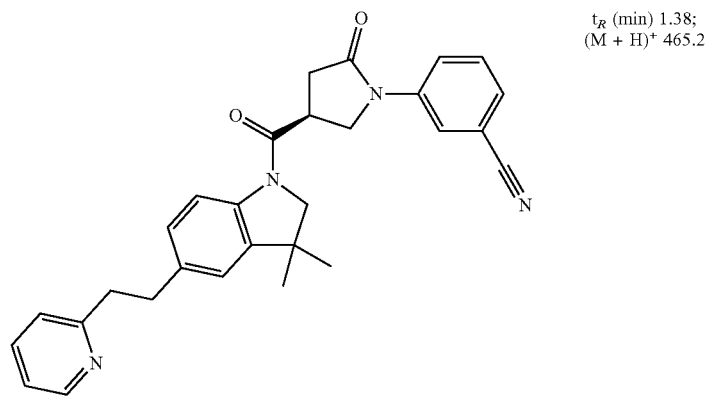 $t_R$ (min) 1.38; $(M + H)^+$ 465.2
11bbb2 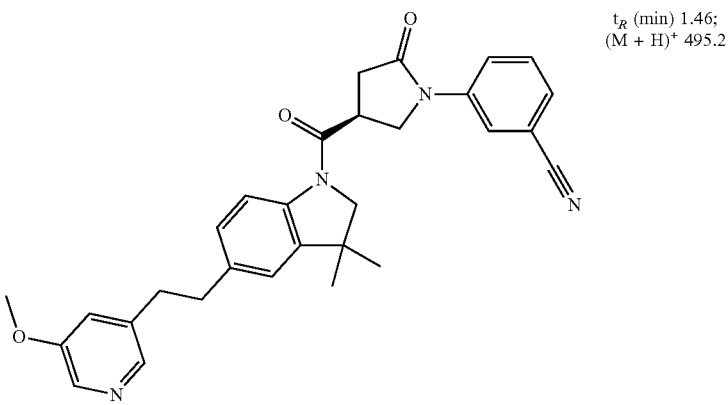 $t_R$ (min) 1.46; $(M + H)^+$ 495.2
11ccc1 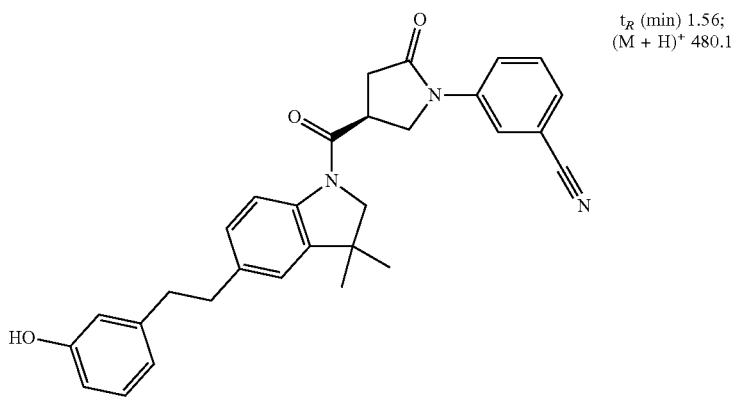 $t_R$ (min) 1.56; $(M + H)^+$ 480.1

| | | |
|---|---|---|
| 11ddd1 | 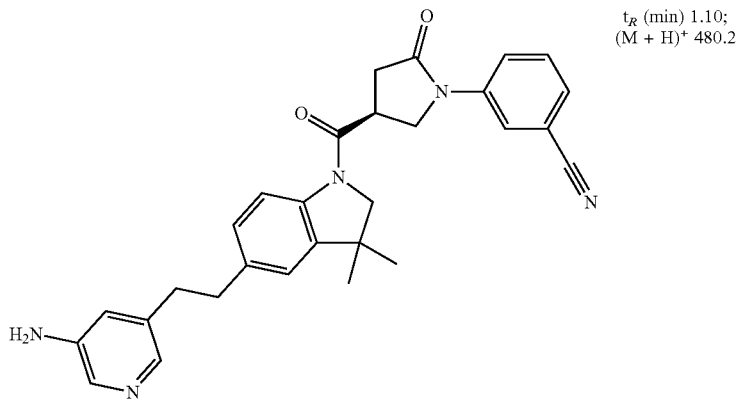 | $t_R$ (min) 1.10; $(M + H)^+$ 480.2 |
| 11eee1 | 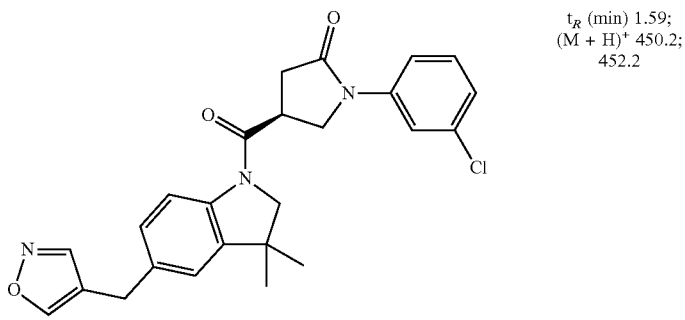 | $t_R$ (min) 1.59; $(M + H)^+$ 450.2; 452.2 |
| 11fff1 | 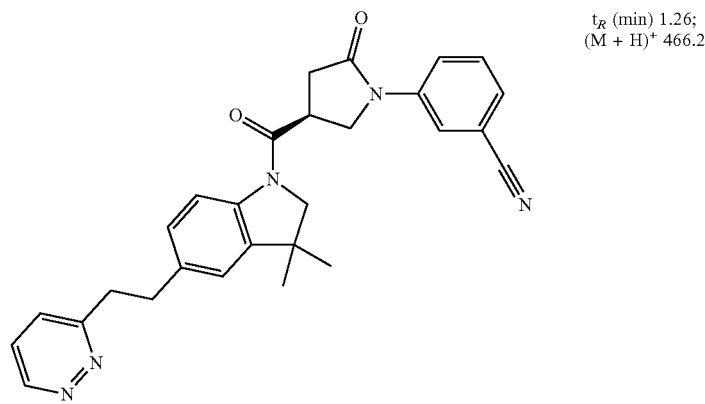 | $t_R$ (min) 1.26; $(M + H)^+$ 466.2 |
| 11ggg1 | 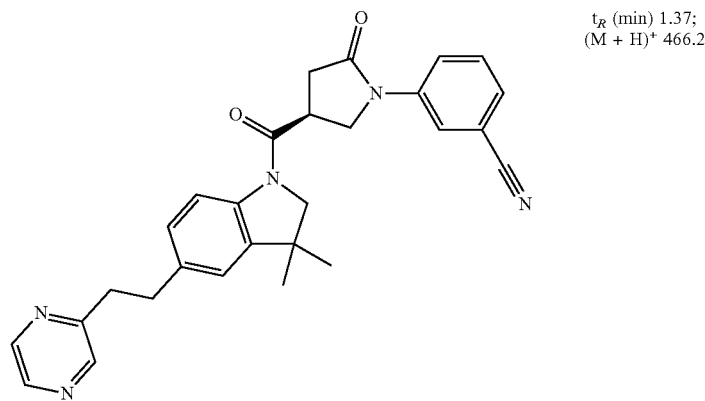 | $t_R$ (min) 1.37; $(M + H)^+$ 466.2 |

| | | |
|---|---|---|
| 11hhh1 | 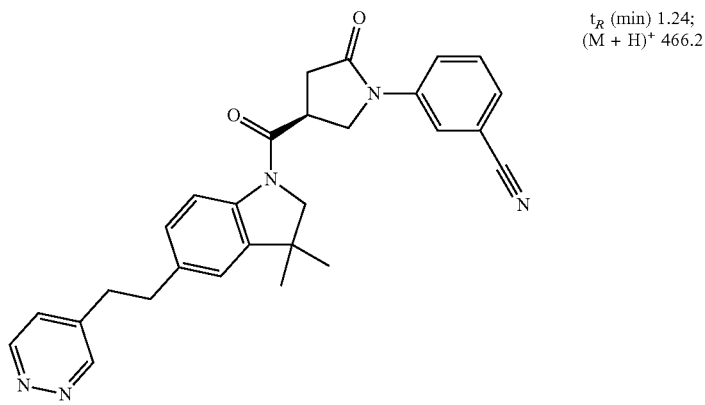 | $t_R$ (min) 1.24; $(M + H)^+$ 466.2 |
| 11iii1 | 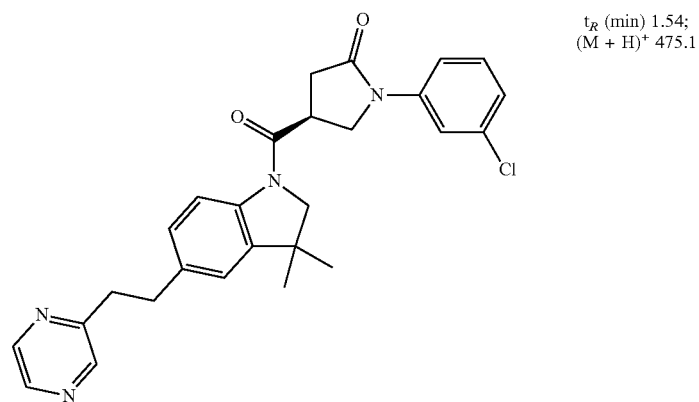 | $t_R$ (min) 1.54; $(M + H)^+$ 475.1 |
| 11jjj1 | 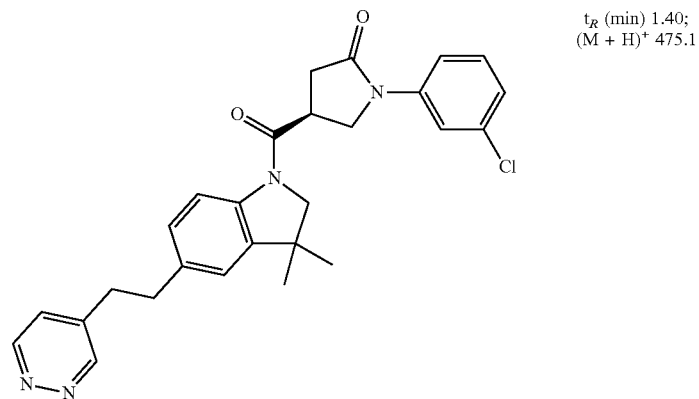 | $t_R$ (min) 1.40; $(M + H)^+$ 475.1 |

Example 12

Preparation of Intermediate 12a1

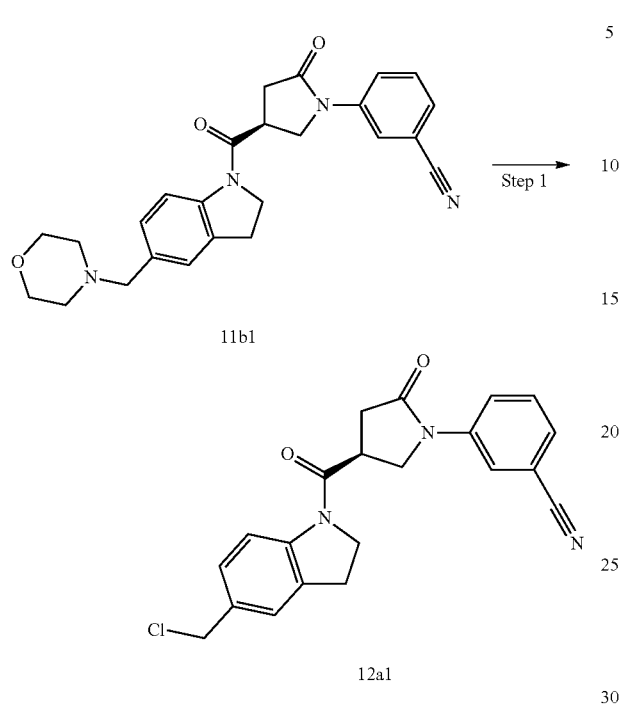

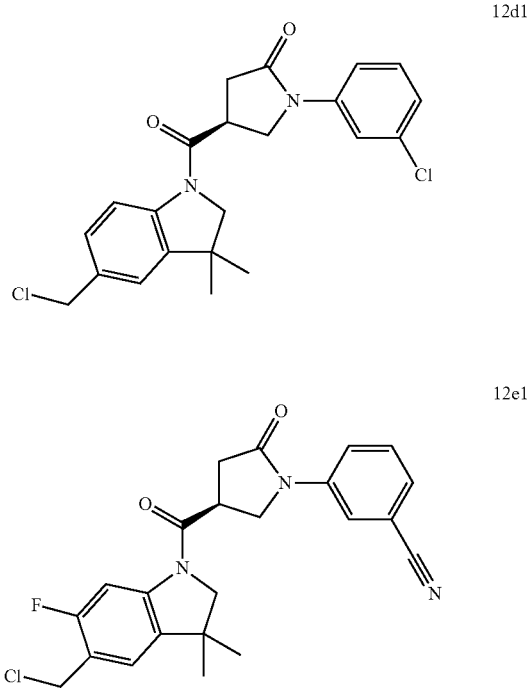

Step 1:

A rounded-bottom flask equipped with a Teflon stir bar is charged with 11b1 (750 mg, 1.7 mmol), chloroform (75 mL) and ethyl chloroformate (330 μL, 3.5 mmol). The mixture is refluxed for 3 h. The mixture is cooled to RT, diluted with DCM, washed with 1N HCl and brine, dried over MgSO$_4$, filtered and concentrated. Purification by Combiflash RF (25 g column, 0-20% MeCN/DCM) gives 12a1 ($t_R$=0.93 min, (M+H—Cl)$^+$ 344.1).

The following intermediates are prepared analogously to the procedure described in Example 12 starting from the appropriate morpholine derivative.

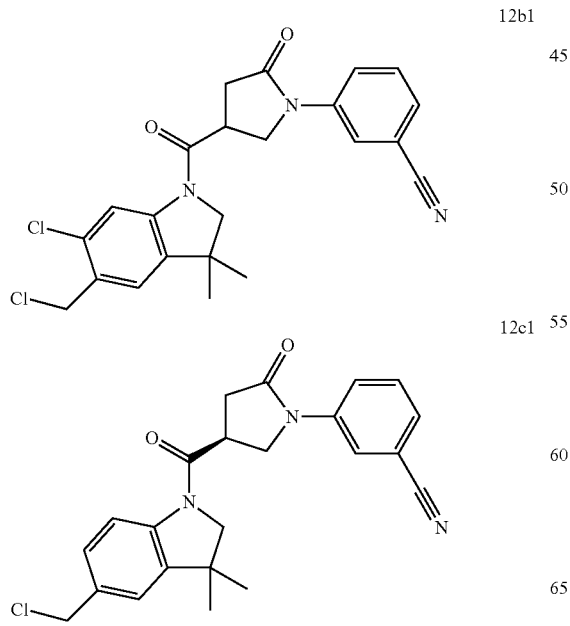

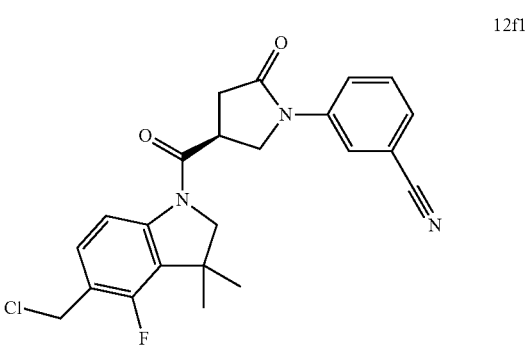

| | |
|---|---|
| 12i1 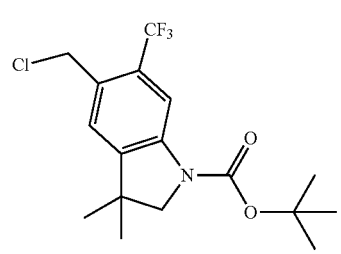 | 12m1 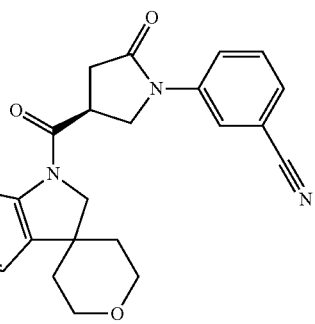 |
| 12j1 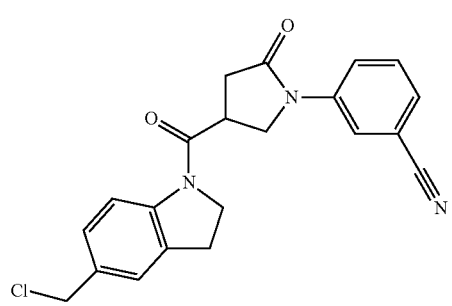 | 12n1 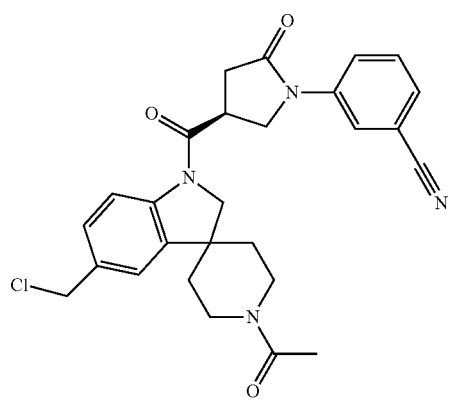 |
| 12k1 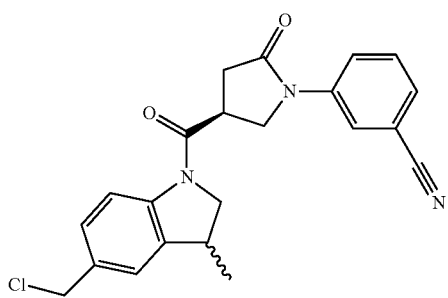 | 12o1 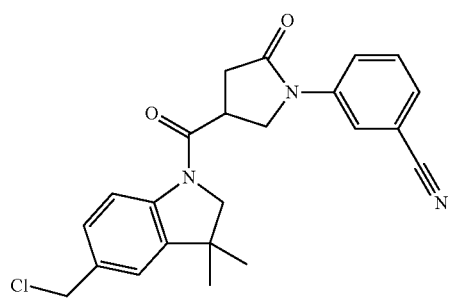 |
| 12l1 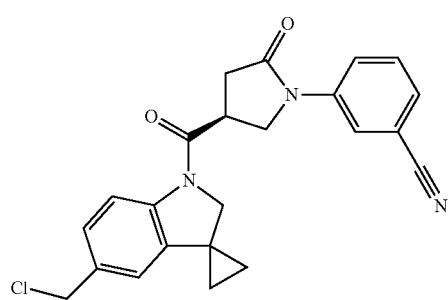 | 12p1 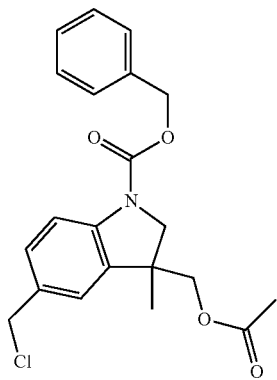 |

12q1

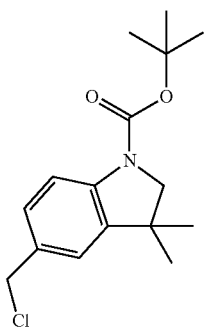

Example 13

Preparation of 13a1

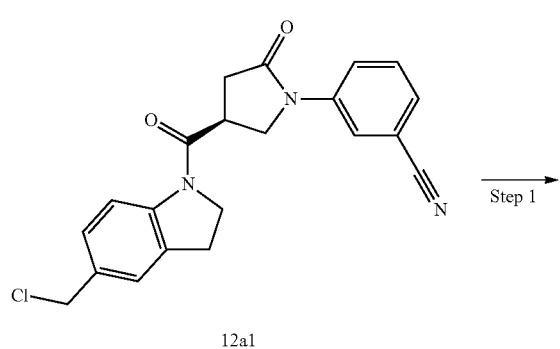

12a1

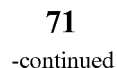

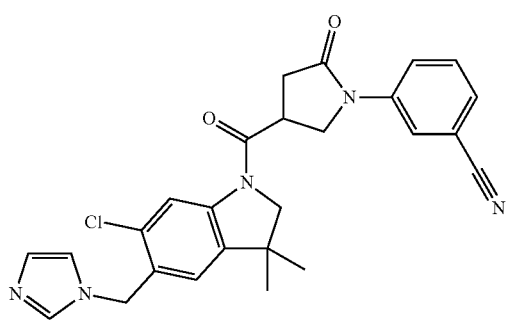 [SMILES: CC1(C)CN(C(=O)C2CC(=O)N(c3cccc(C#N)c3)C2)c2cc(Cl)c(Cn3ccnc3)cc21]

13a1

Step 1:

To 12a1 (560 mg, 1.5 mmol) in DMF (4.7 mL) is added imidazole (510 mg, 7.4 mol) and the mixture is stirred at 80° C. for 1.5 h. The mixture is cooled to RT, diluted with AcOH/MeOH, filtered with an Acrodisc filter and purified by preparative-HPLC MeCN/H$_2$O (containing 5 mM of ammonium formate). The pure fractions are combined, concentrated, diluted with a mixture of MeCN/H$_2$O, frozen and lyophilized to afford 13a1 (t$_R$=0.76 min, (M+H)$^+$ 412.1).

The following compounds are prepared analogously to the procedure described in Example 13 starting from the appropriate chloro or mesylate derivative.

| | | |
|---|---|---|
| 13b1 | 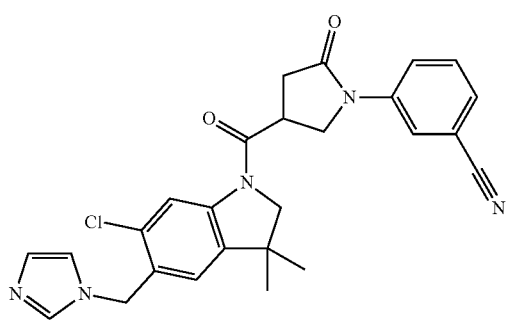 [SMILES: CC1(C)CN(C(=O)C2CC(=O)N(c3cccc(C#N)c3)C2)c2cc(Cl)c(Cn3ccnc3)cc21] | t$_R$ (min) 1.02; (M + H)$^+$ 474.1; 476.0 |
| 13c1 | 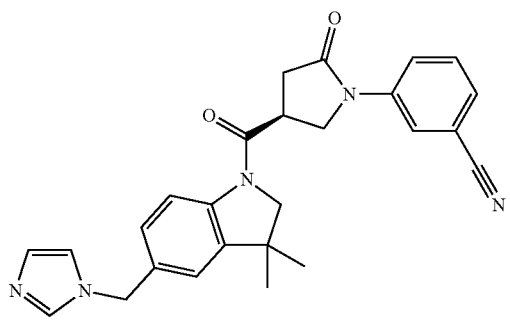 [SMILES: CC1(C)CN(C(=O)[C@H]2CC(=O)N(c3cccc(C#N)c3)C2)c2ccc(Cn3ccnc3)cc21] | t$_R$ (min) 0.90; (M + H)$^+$ 440.1 |

-continued
| | | |
|---|---|---|
| 13d1 | 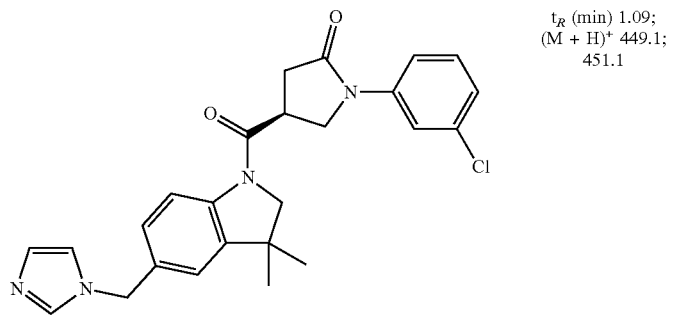 | $t_R$ (min) 1.09; (M + H)$^+$ 449.1; 451.1 |
| 13e1 | 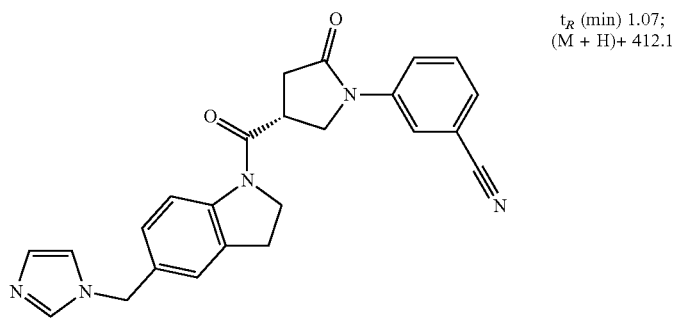 | $t_R$ (min) 1.07; (M + H)+ 412.1 |
| 13f1 | 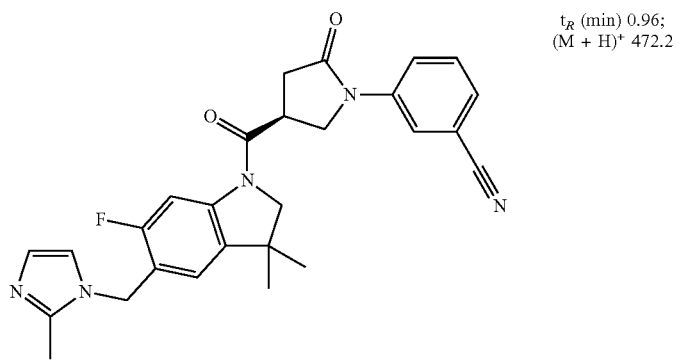 | $t_R$ (min) 0.96; (M + H)$^+$ 472.2 |
| 13g1 | 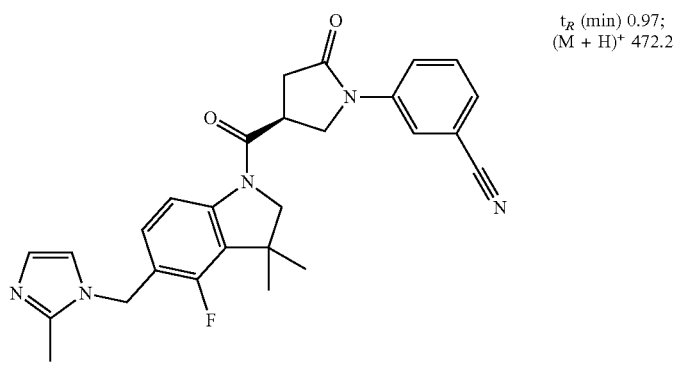 | $t_R$ (min) 0.97; (M + H)$^+$ 472.2 |
| 13h1 | 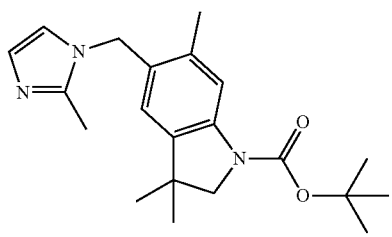 [SMILES: Cc1cc2c(cc1Cn1ccnc1C)C(C)(C)CN2C(=O)OC(C)(C)C] | |

| | | |
|---|---|---|
| 13i1 | 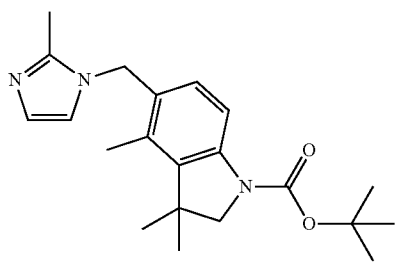 [SMILES: Cc1c(Cn2ccnc2C)ccc2c1C(C)(C)CN2C(=O)OC(C)(C)C] | |
| 13j1 | 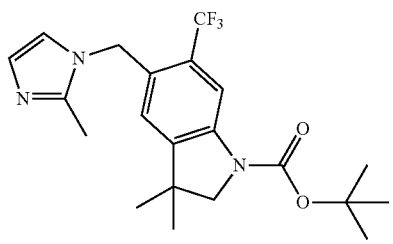 [SMILES: Cc1nccn1Cc1cc2c(cc1C(F)(F)F)N(C(=O)OC(C)(C)C)CC2(C)C] | |
| 13k1 | 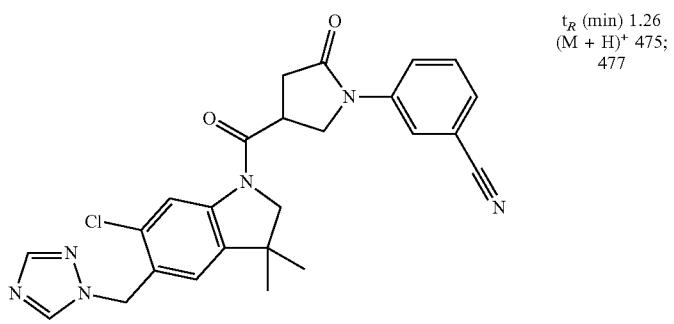 | t<sub>R</sub> (min) 1.26<br>(M + H)<sup>+</sup> 475;<br>477 |
| 13l1 | 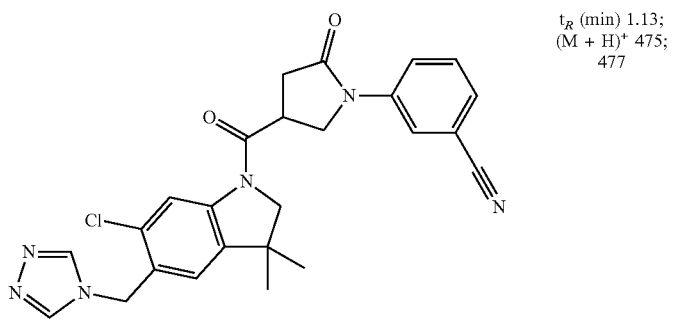 | t<sub>R</sub> (min) 1.13;<br>(M + H)<sup>+</sup> 475;<br>477 |
| 13n1 | 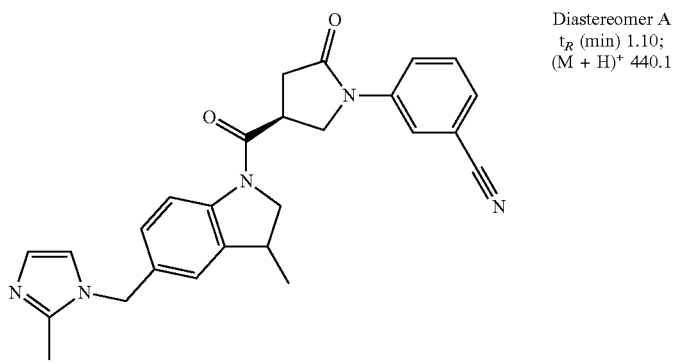 | Diastereomer A<br>t<sub>R</sub> (min) 1.10;<br>(M + H)<sup>+</sup> 440.1 |

| | | |
|---|---|---|
| 13o1 | 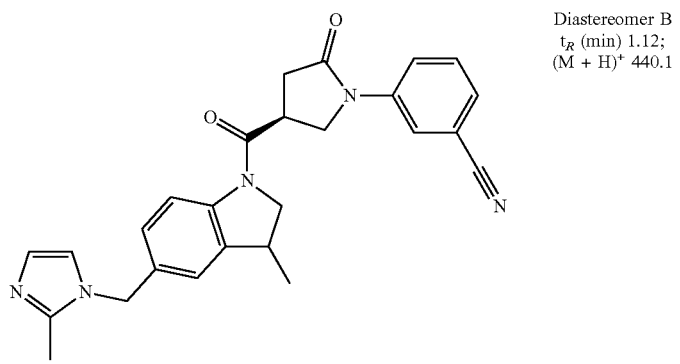 | Diastereomer B<br>$t_R$ (min) 1.12;<br>$(M + H)^+$ 440.1 |
| 13p1 | 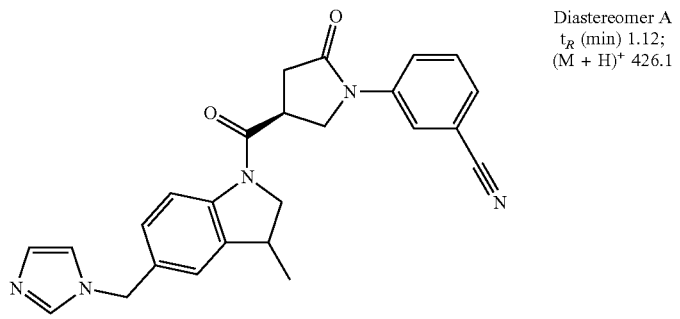 | Diastereomer A<br>$t_R$ (min) 1.12;<br>$(M + H)^+$ 426.1 |
| 13q1 | 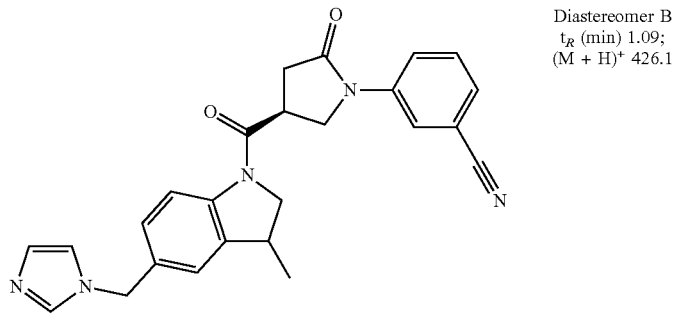 | Diastereomer B<br>$t_R$ (min) 1.09;<br>$(M + H)^+$ 426.1 |
| 13r1 | 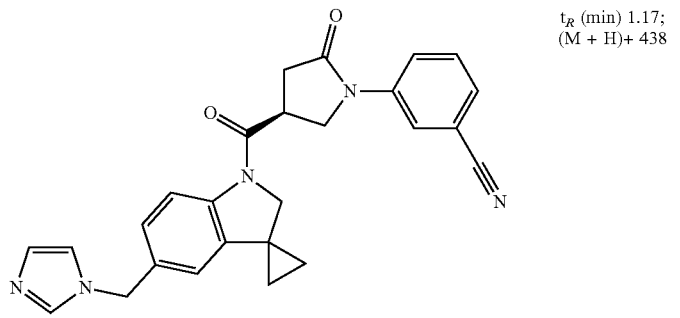 | $t_R$ (min) 1.17;<br>$(M + H)+$ 438 |

| | | |
|---|---|---|
| 13s1 | 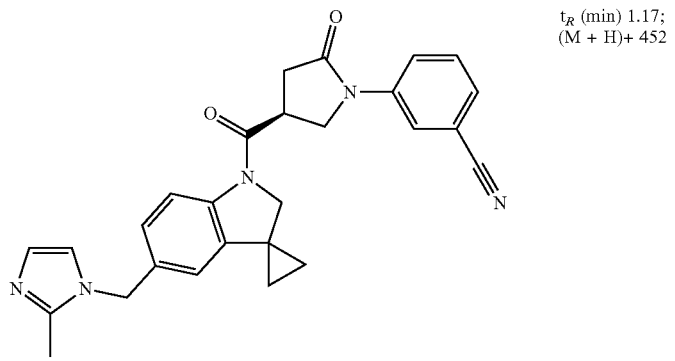 | t_R (min) 1.17; (M + H)+ 452 |
| 13t1 | 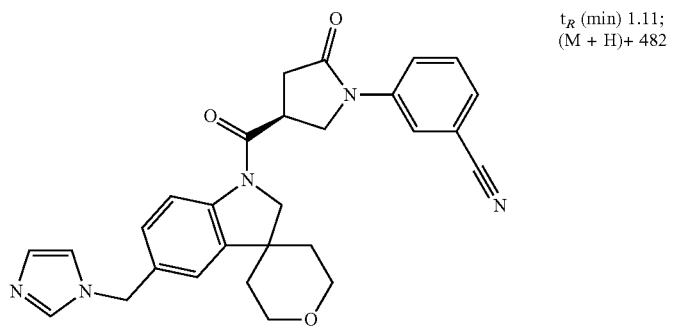 | t_R (min) 1.11; (M + H)+ 482 |
| 13u1 | 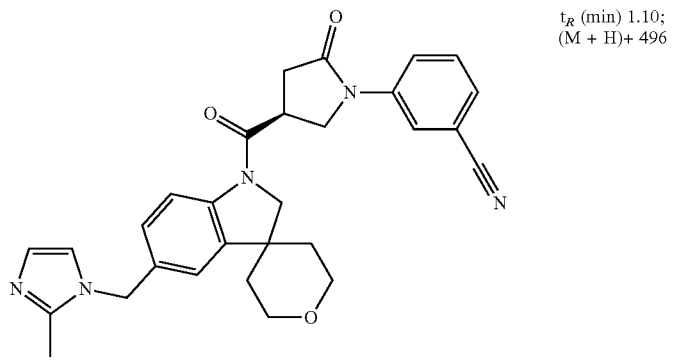 | t_R (min) 1.10; (M + H)+ 496 |
| 13v1 | 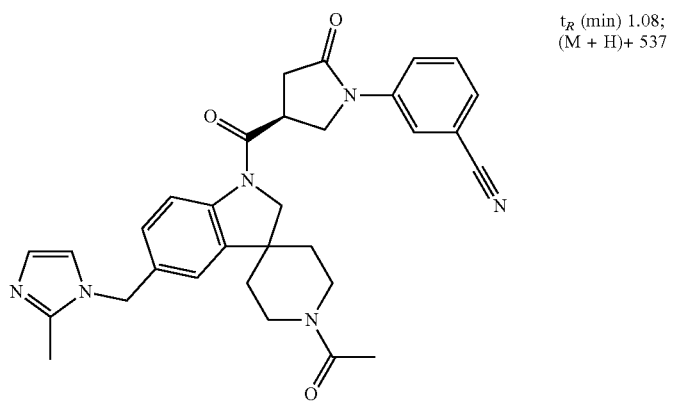 | t_R (min) 1.08; (M + H)+ 537 |

| | | |
|---|---|---|
| 13w1 | 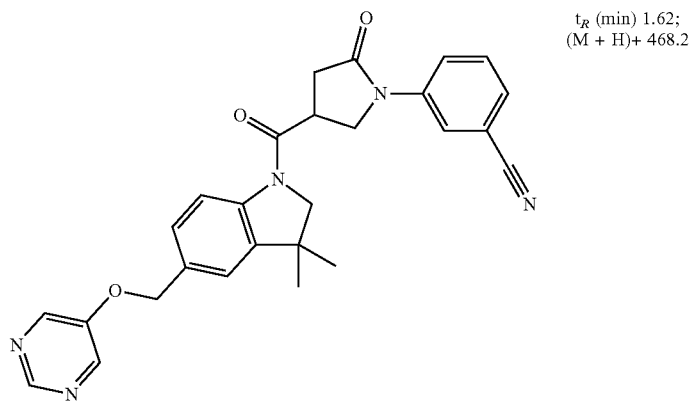 | $t_R$ (min) 1.62; (M + H)+ 468.2 |
| 13w2 | 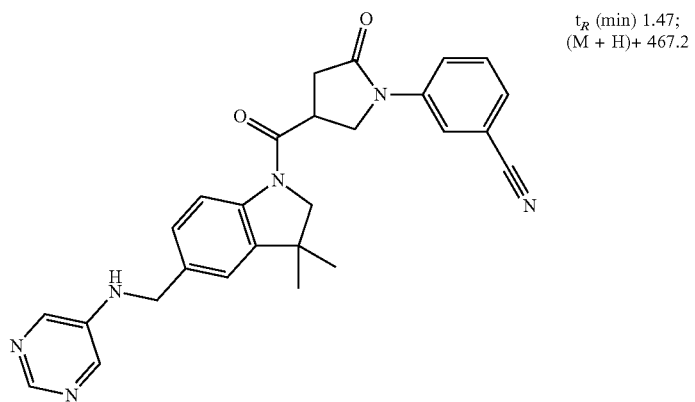 | $t_R$ (min) 1.47; (M + H)+ 467.2 |
| 13x1 | 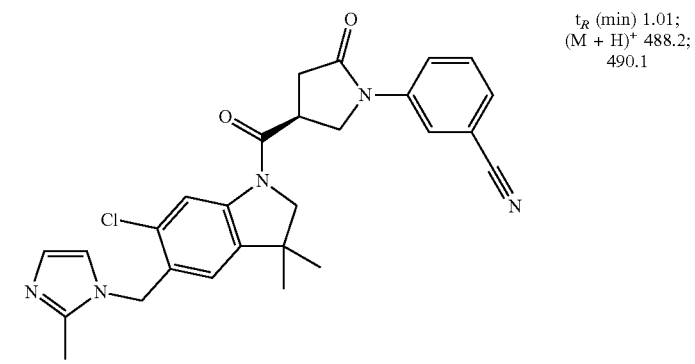 | $t_R$ (min) 1.01; (M + H)$^+$ 488.2; 490.1 |
| 13y1 | 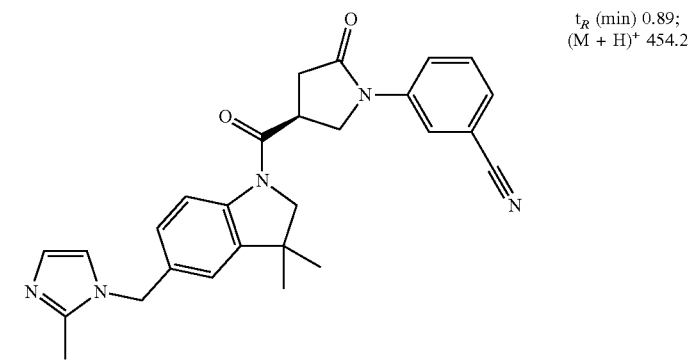 | $t_R$ (min) 0.89; (M + H)$^+$ 454.2 |

13z1
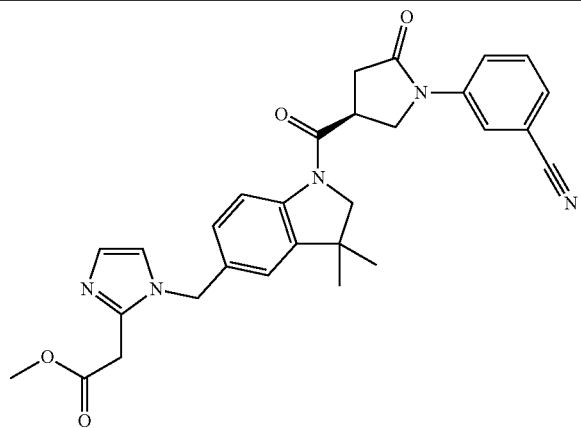
13aa1
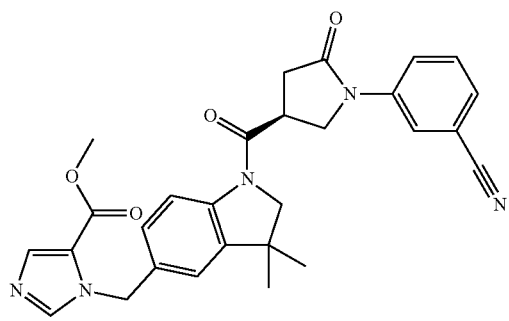 [SMILES: COC(=O)c1cncn1Cc1ccc2c(c1)C(C)(C)CN2C(=O)[C@H]1CC(=O)N(c2cccc(C#N)c2)C1]
13bb1
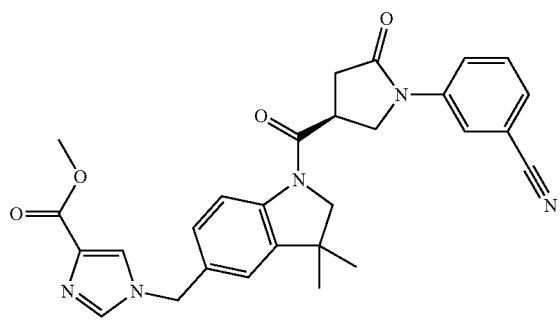 [SMILES: COC(=O)c1cn(Cc2ccc3c(c2)C(C)(C)CN3C(=O)[C@H]2CC(=O)N(c3cccc(C#N)c3)C2)cn1]
13cc1
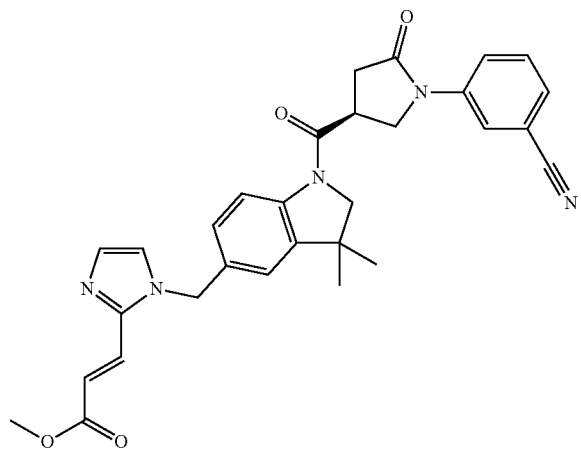 [SMILES: COC(=O)/C=C/c1nccn1Cc1ccc2c(c1)C(C)(C)CN2C(=O)[C@H]1CC(=O)N(c2cccc(C#N)c2)C1]

-continued
13dd1
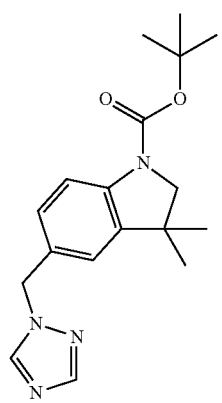 [SMILES: CC(C)(C)OC(=O)N1CC(C)(C)c2cc(Cn3cncn3)ccc21]
13ee1
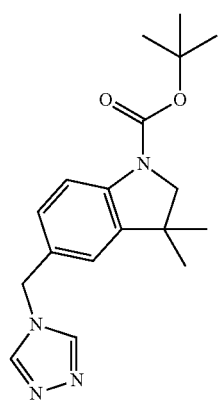 [SMILES: CC(C)(C)OC(=O)N1CC(C)(C)c2cc(Cn3cnnc3)ccc21]
13ff1
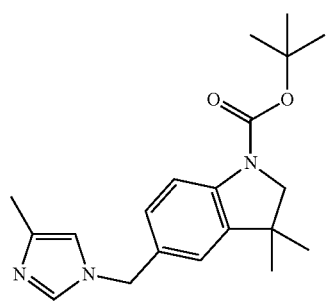 [SMILES: Cc1cn(Cc2ccc3c(c2)C(C)(C)CN3C(=O)OC(C)(C)C)cn1]
13gg1
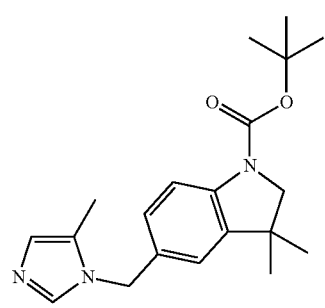 [SMILES: Cc1cncn1Cc1ccc2c(c1)C(C)(C)CN2C(=O)OC(C)(C)C]

Example 14

Preparation of Intermediate 14a1

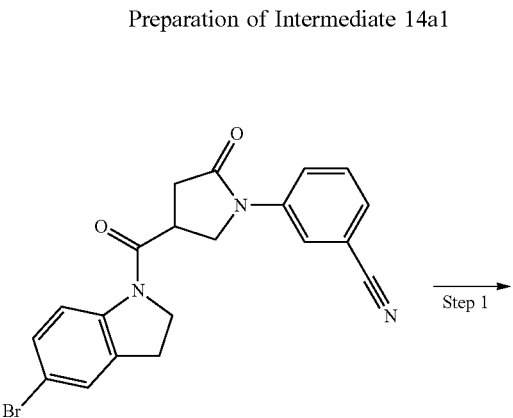

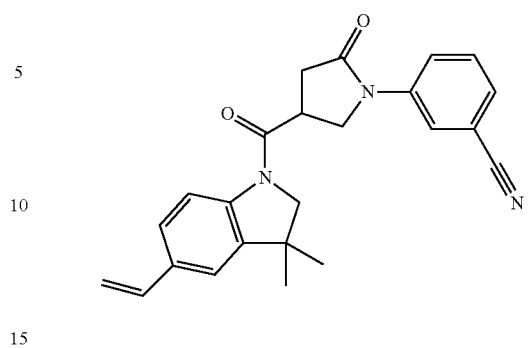

Step 1:

A pressure vessel equipped with a Teflon stir bar is charged with 11d1 (690 mg, 1.7 mmol), 2,4,6-trivinylcyclotriboroxane pyridine complex (420 mg, 1.7 mmol), sodium carbonate (2M in water, 5 mL, 10 mmol), Pd(PPh$_3$)$_4$ (180 mg; 0.15 mmol) and DME (20 mL). The solution is degassed by bubbling argon for 5 min. The vessel is sealed and heated at 80° C. overnight. The reaction mixture is cooled to RT, poured into EtOAc, washed with water and brine, dried over MgSO$_4$, filtered and concentrated. Purification by Combiflash RF (24 g column, 0-30% MeCN/DCM) gives 14a1 ($t_R$=1.78 min, (M+H)$^+$ 358).

The following intermediates are prepared analogously to the procedure described in Example 14 starting from the appropriate bromo and boronic acid derivatives.

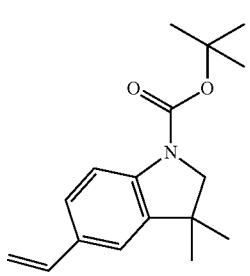

Example 15

Preparation of Intermediate 15a1

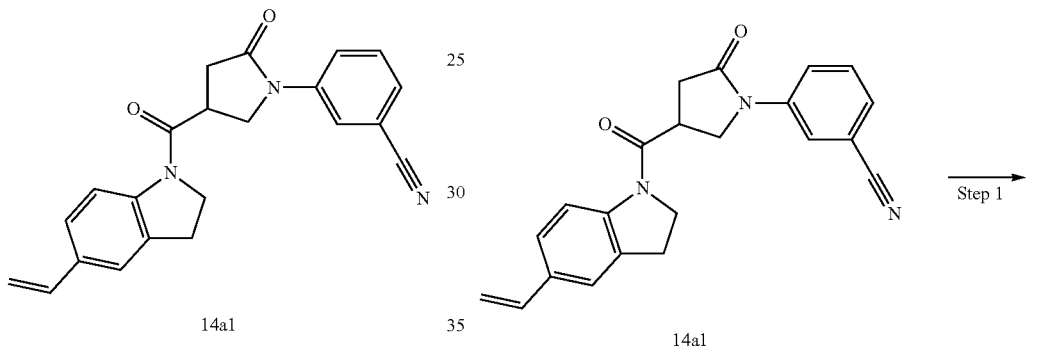

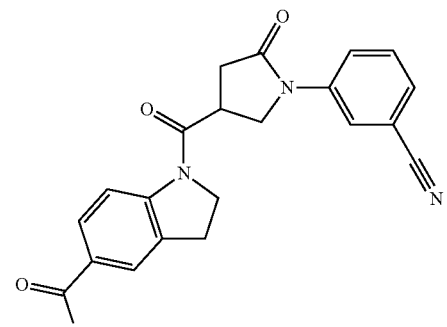

Step 1:

A mixture of the olefin 14a1 (470 mg, 1.3 mmol), a solution of OsO$_4$ in t-BuOH (0.1 M, 260 μL, 0.03 mmol) and a solution of NaIO$_4$ in water (0.5 M, 9.3 mL, 4.6 mmol) in THF (10 mL) are stirred at RT for 4 h. The mixture is poured in water and extracted twice with EtOAc. The organic layer is dried with MgSO$_4$, filtered and evaporated to generate 15a1 ($t_R$=1.48 min, (M+H)$^+$ 360).

The following intermediate is prepared analogously to the procedure described in Example 15 starting from the appropriate vinyl derivative.

Example 16

Preparation of 16a3

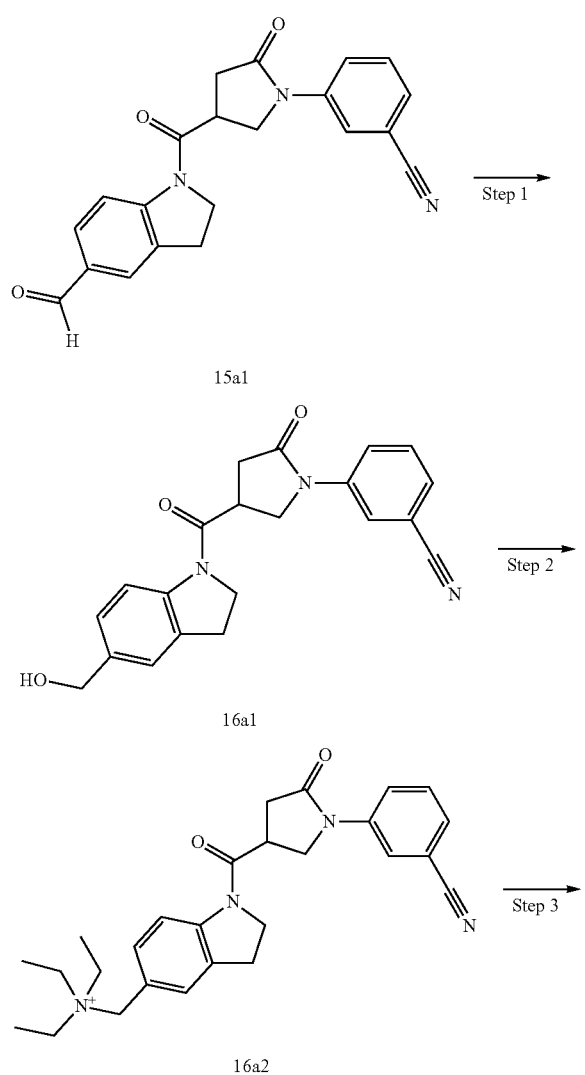
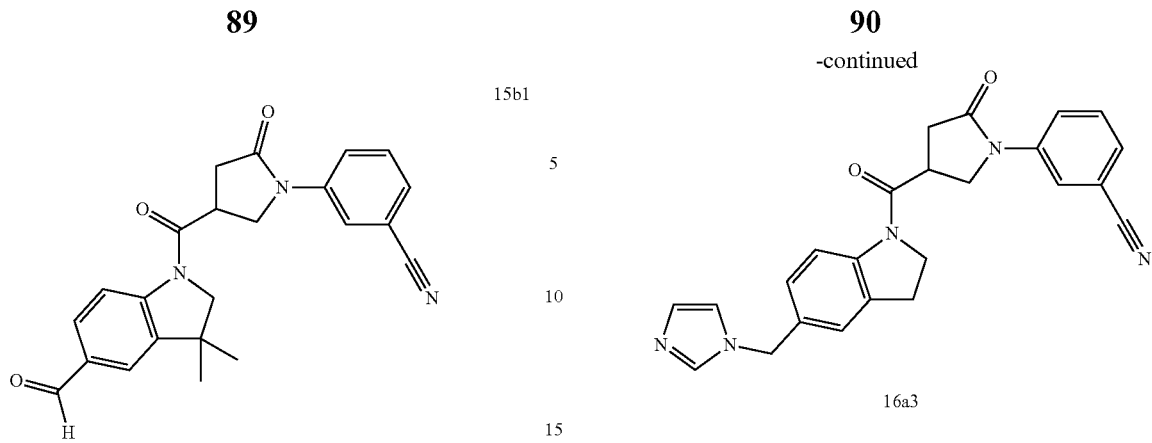

Step 1:

A mixture of aldehyde 15a1 (390 mg, 1.1 mmol) in MeOH (10 mL) (1 mL of THF is added to complete the solubilization) is stirred at RT under $N_2$ (g). $NaBH_4$ (81 mg, 2.1 mmol) is added and the mixture is stirred at RT for 2 h. The reaction mixture is neutralized with 1N HCl and then concentrated. EtOAc is added and the organic layer is washed with brine, dried over $Na_2SO_4$, filtered and evaporated. Purification by Combi-Flash Rf (0-50% MeCN/$CH_2Cl_2$ as eluent in 25 min with a 4 g column) affords 16a1 ($t_R$=1.33 min, $(M+OMe)^+$=376.1).

Step 2:

A solution of alcohol 16a1 (160 mg, 0.4 mmol) in $CH_2Cl_2$ (110 mL) is stirred at 0° C. under $N_2$ (g). $Et_3N$ (0.15 mL, 1.1 mmol) is added followed by methanesulfonylchloride (50 μL, 0.65 mmol) over 15 min. The reaction mixture is warmed to RT over 2 h. Water is added and the layers are separated. The organic layer is washed with brine, dried over $MgSO_4$, filtered then evaporated to give 16a2 ($t_R$=1.05 min, $(M+H)^+$=445.1).

Step 3:

To 16a2 (40 mg, 0.09 mmol) in DMF (2 mL) is added imidazole (31 mg, 0.45 mmol) and the mixture is stirred at 140° C. for 16 h. The mixture is cooled to RT, diluted with AcOH/MeOH, filtered with an Acrodisc filter and purified by preparative-HPLC MeOH/$H_2O$ (containing 5 mM of ammonium formate). The pure fractions are combined, concentrated, diluted with a mixture of MeCN/$H_2O$, frozen and lyophilized to afford 16a3 (($t_R$=1.06 min, $(M+H)^+$ 412.0).

The following compounds are prepared analogously to the procedure described in Example 16 starting from the appropriate aldehyde derivative.

| | | |
|---|---|---|
| 16b3 | 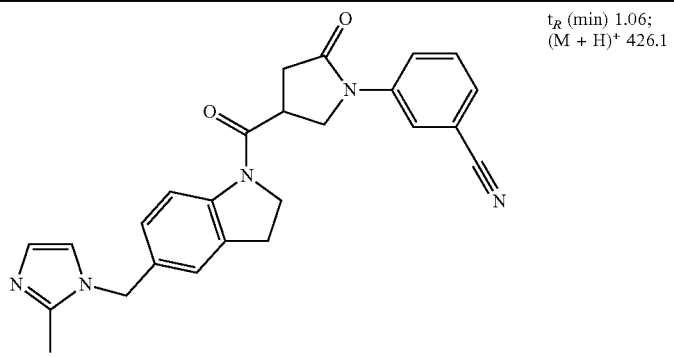 | $t_R$ (min) 1.06; $(M + H)^+$ 426.1 |
| 16c3 | 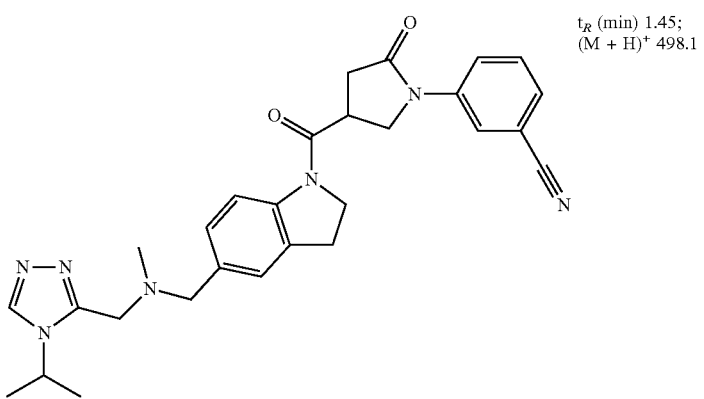 | $t_R$ (min) 1.45; $(M + H)^+$ 498.1 |
| 16d3 | 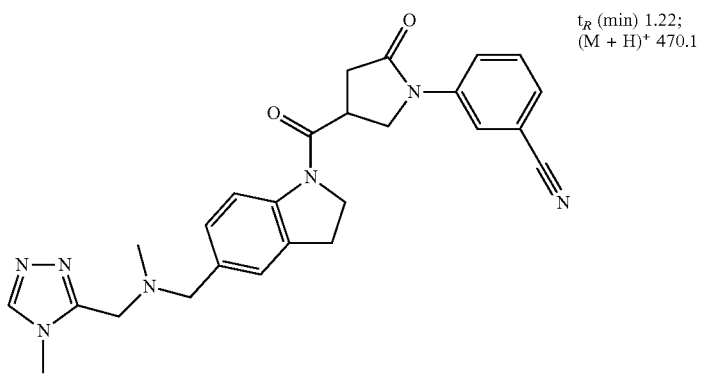 | $t_R$ (min) 1.22; $(M + H)^+$ 470.1 |
Example 17
Preparation of Intermediate 17a1
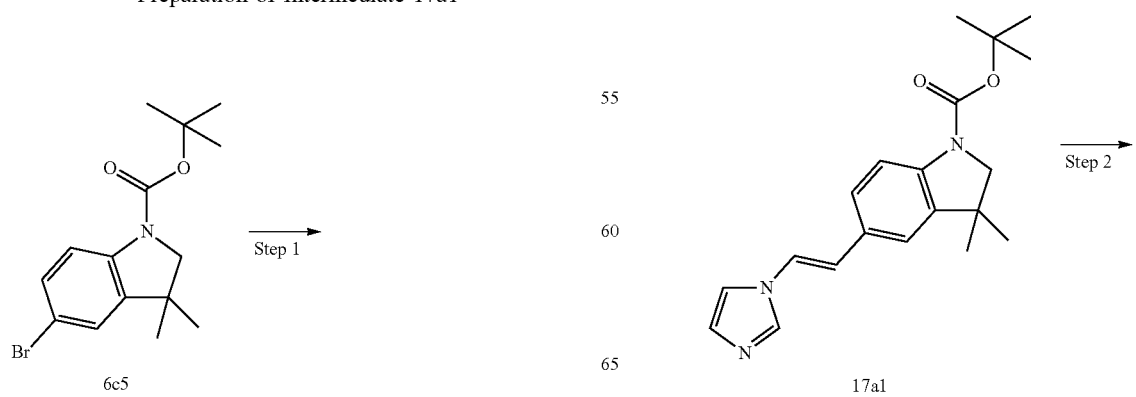

-continued

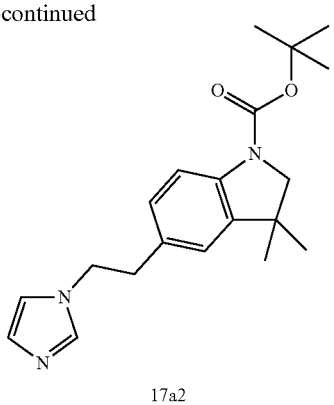

17a2

Step 1:
A pressure vessel equipped with a Teflon stir bar is charged with 6c5 (250 mg, 0.8 mmol), 1-vinylimidazole (90 mg, 1 mmol), tri-o-tolyphosphine (33 mg, 0.11 mmol), diisopropylamine (0.4 mL, 2.3 mmol), Pd(OAc)$_2$ (12 mg; 0.05 mmol) and DMF (18 mL). The solution is degassed by bubbling argon for 5 min. The vessel is sealed and heated at 110° C. overnight. The reaction mixture is cooled to RT, poured into EtOAc and extracted with 0.1N HCl. The aqueous layer is basified with potassium carbonate and extracted with EtOAc. The organic layer is washed with brine, dried over MgSO$_4$, filtered and concentrated to afford 17a1 ($t_R$=1.52 min, (M+H)$^+$ 340).

Step 2:
17a1 (190 mg, 0.55 mmol) is dissolved in EtOH (20 mL) and purged under argon. Pd/C (10% w/w) is added. The mixture is purged under argon and then placed under H$_2$ (1 atm) for 16 h. The reaction mixture is filtered through a pad of celite and washed with MeOH. The filtrate is concentrated to dryness to afford 17a2 ($t_R$=1.21 min, (M+H)$^+$ 342.2).

The following compounds are prepared analogously to the procedure described in Example 17 starting from the appropriate bromo and vinylic derivatives.

17b1

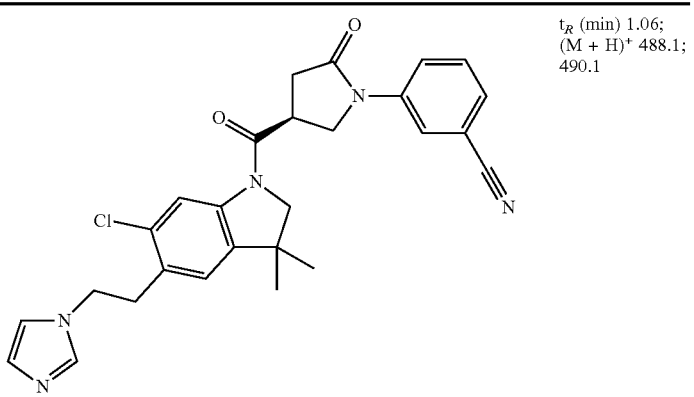

$t_R$ (min) 1.06;
(M + H)$^+$ 488.1;
490.1

17c1

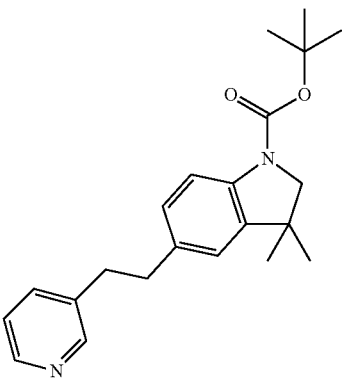 [SMILES: CC(C)(C)OC(=O)N1CC(C)(C)c2cc(CCc3cccnc3)ccc21]

17c1

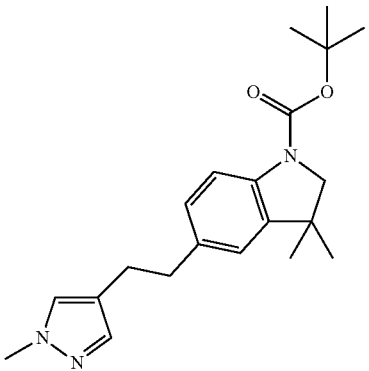 [SMILES: Cn1cc(CCc2ccc3c(c2)C(C)(C)CN3C(=O)OC(C)(C)C)cn1]

-continued
17d1 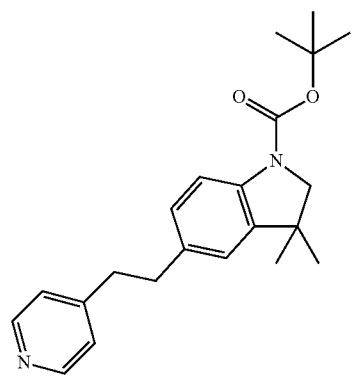 [SMILES: CC(C)(C)OC(=O)N1CC(C)(C)c2cc(CCc3ccncc3)ccc21]
17e1 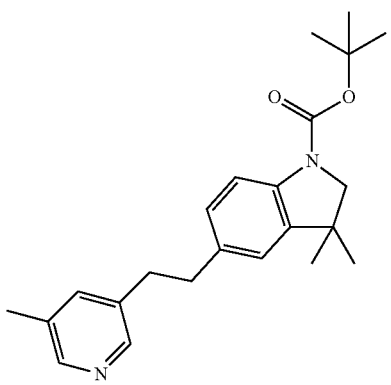 [SMILES: Cc1cncc(CCc2ccc3c(c2)C(C)(C)CN3C(=O)OC(C)(C)C)c1]
17e1 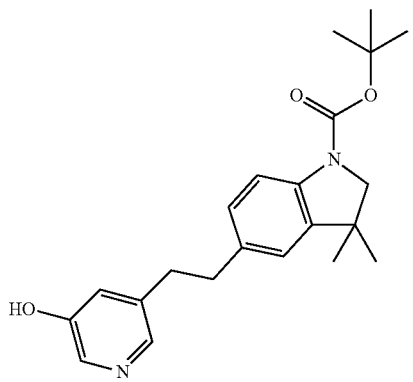 [SMILES: CC(C)(C)OC(=O)N1CC(C)(C)c2cc(CCc3cncc(O)c3)ccc21]
17f1 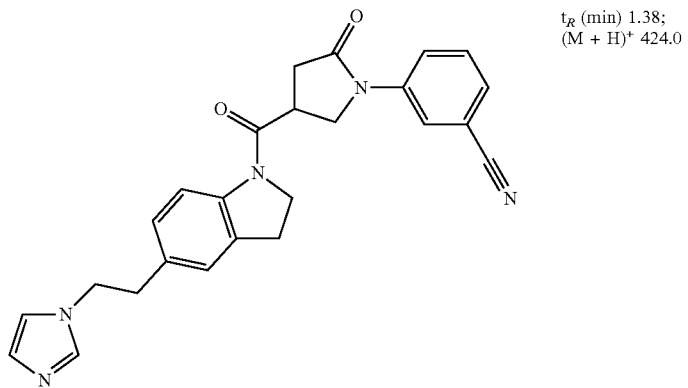 $t_R$ (min) 1.38; $(M + H)^+$ 424.0

-continued
| | | |
|---|---|---|
| 17g1 | 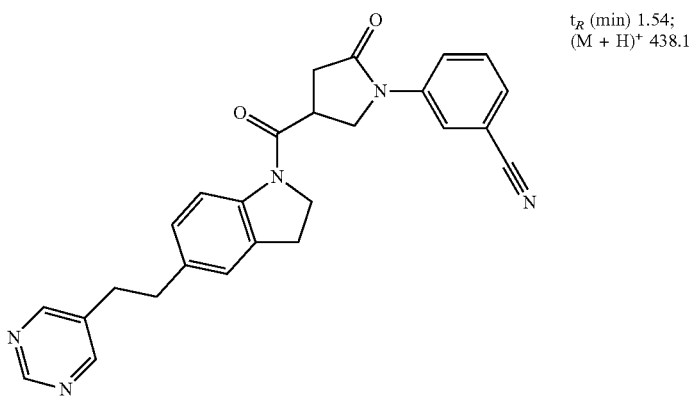 | $t_R$ (min) 1.54; $(M + H)^+$ 438.1 |
| 17h1 | 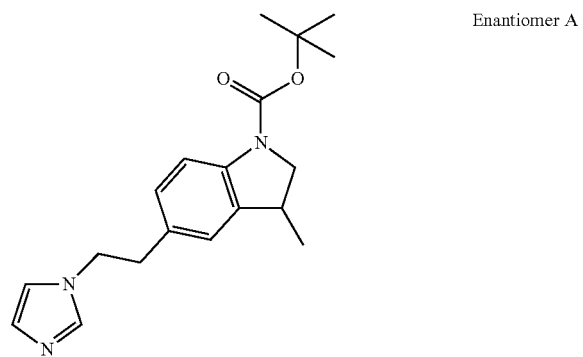 | Enantiomer A |
| 17i1 | 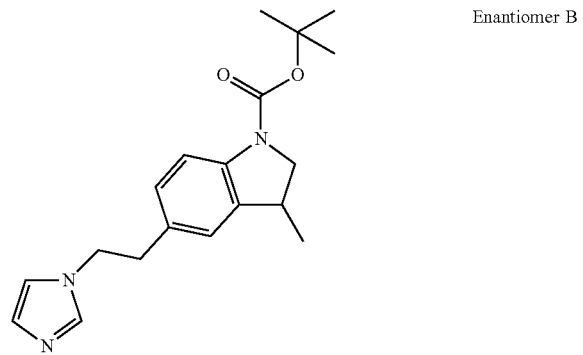 | Enantiomer B |
| 17j1 | 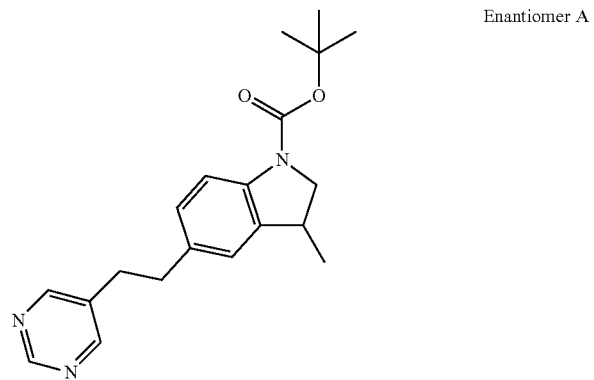 | Enantiomer A |

| | | |
|---|---|---|
| 17k1 | 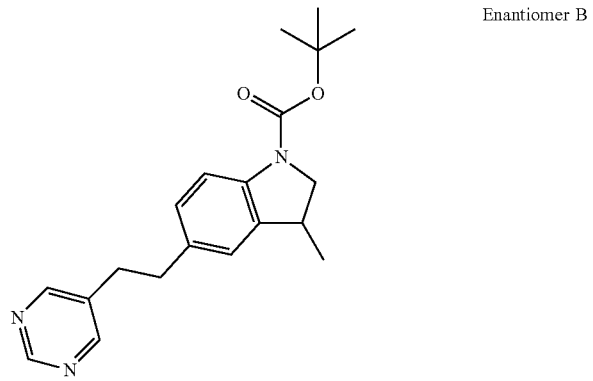 | Enantiomer B |
| 17l1 | 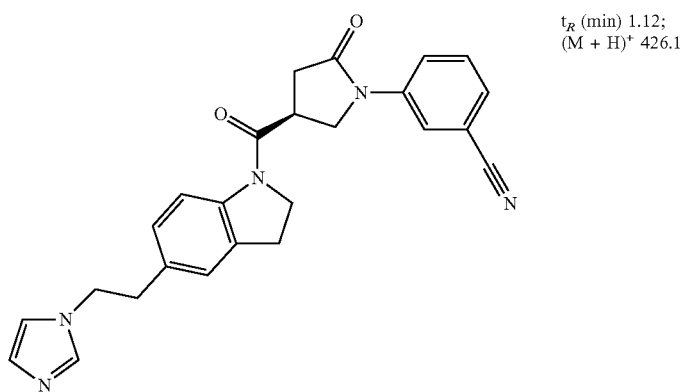 | $t_R$ (min) 1.12; $(M + H)^+$ 426.1 |
| 17m1 | 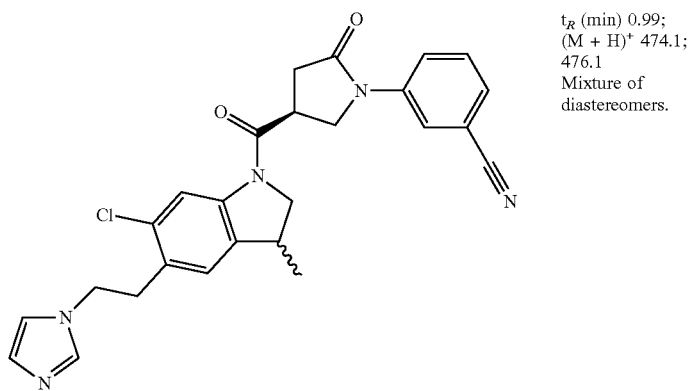 | $t_R$ (min) 0.99; $(M + H)^+$ 474.1; 476.1 Mixture of diastereomers. |
| 17n1 | 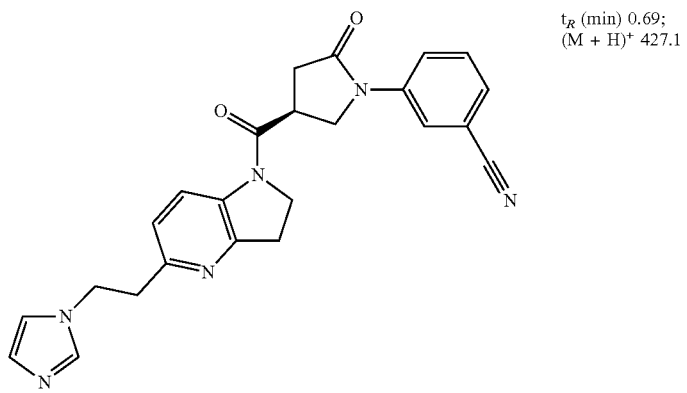 | $t_R$ (min) 0.69; $(M + H)^+$ 427.1 |

| | | |
|---|---|---|
| 17o1 | 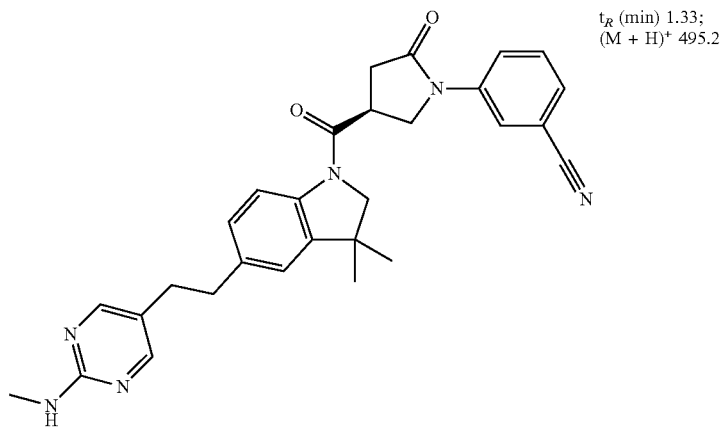 | t$_R$ (min) 1.33; (M + H)$^+$ 495.2 |
| 17p1 | 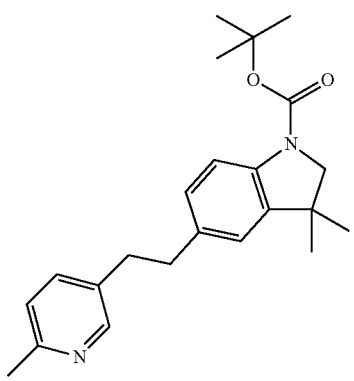 | |
| 17q1 | 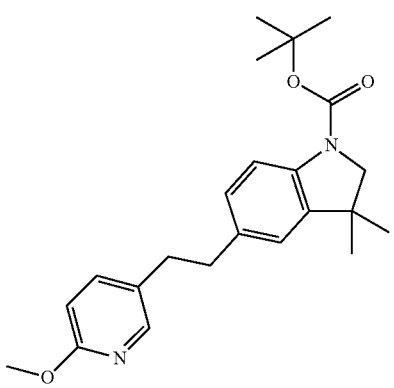 | |
| 17r1 | 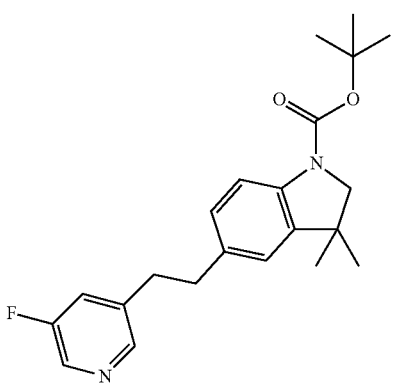 [SMILES: CC(C)(C)OC(=O)N1CC(C)(C)c2cc(CCc3cncc(F)c3)ccc21] | |

17s1 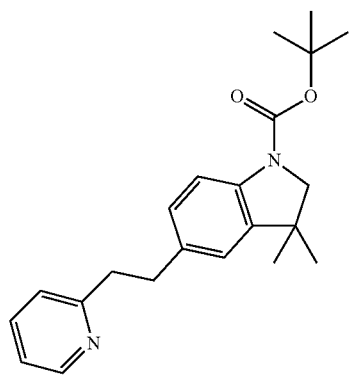 [SMILES: CC(C)(C)OC(=O)N1CC(C)(C)c2cc(CCc3ccccn3)ccc21]
17t1 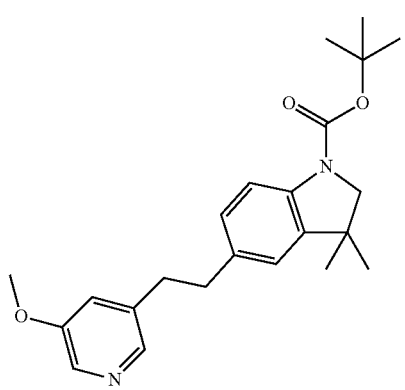 [SMILES: COc1cncc(CCc2ccc3c(c2)C(C)(C)CN3C(=O)OC(C)(C)C)c1]
17u1 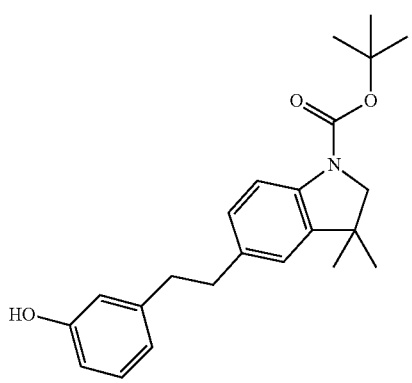 [SMILES: CC(C)(C)OC(=O)N1CC(C)(C)c2cc(CCc3cccc(O)c3)ccc21]
17v1 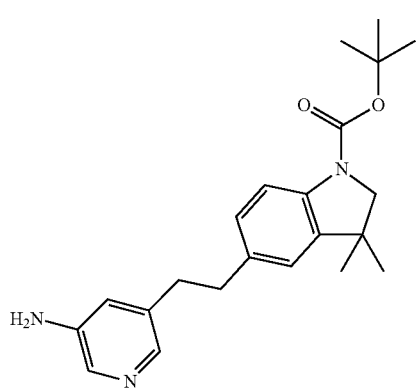 [SMILES: CC(C)(C)OC(=O)N1CC(C)(C)c2cc(CCc3cncc(N)c3)ccc21]

Example 18

Preparation of Intermediate 18a4

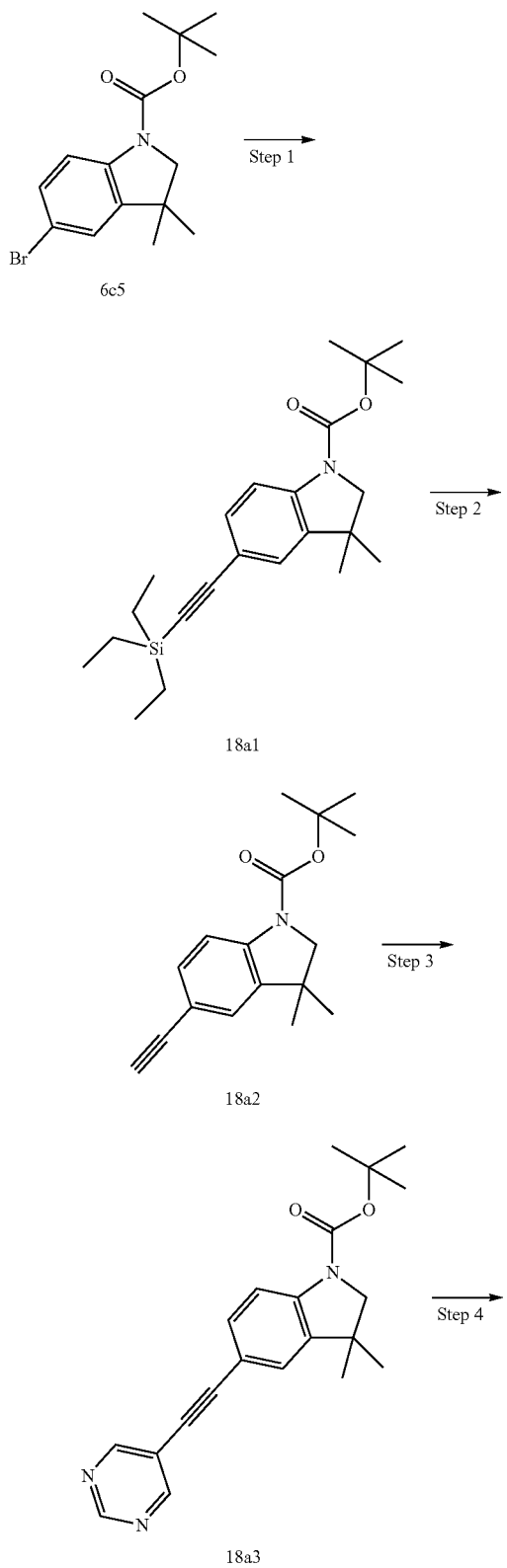

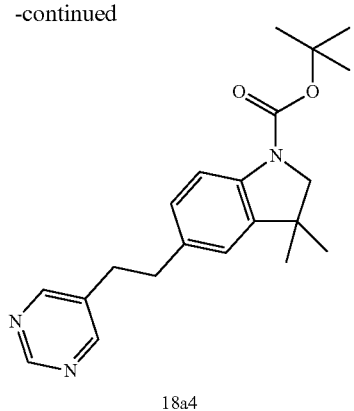

Step 1:

A pressure vessel equipped with a Teflon stir bar is charged with 6c5 (410 mg, 1.3 mmol), (triethylsilyl)acetylene (220 mg, 1.6 mmol), diethylamine (650 µL, 6.3 mmol), copper iodide (24 mg, 0.13 mmol), Pd(PPh$_3$)$_4$ (130 mg; 0.12 mmol) and DMF (5.5 mL). The solution is degassed by bubbling argon for 5 min. The vessel is sealed and heated at 90° C. overnight. The reaction mixture is cooled to RT and poured into EtOAc. The organic layer is washed with a 1N solution of citric acid and brine, dried over MgSO$_4$, filtered and concentrated. Purification by Combi-Flash Rf (0-2% EtOAc/Hexanes as eluent on a 12 g column) affords 18a1 ($t_R$=2.52 min).

Step 2:

18a1 (450 mg, 1.2 mmol) is dissolved in MeOH (18 mL) and treated with a solution of TBAF in THF (1M, 1.3 mL, 1.3 mmol) at 70° C. for 16 h. The reaction mixture is cooled to RT and concentrated. Purification by Combi-Flash Rf (0-10% EtOAc/Hexanes as eluent on a 12 g column) affords 18a2 ($t_R$=1.93 min).

Step 3:

A pressure vessel equipped with a Teflon stir bar is charged with 18a2 (260 mg, 0.95 mmol), 5-bromopyrimidine (190 mg, 1.2 mmol), diethylamine (491 µL, 4.8 mmol), copper iodide (18 mg, 0.10 mmol), Pd(PPh$_3$)$_4$ (100 mg; 0.09 mmol) and DMF (4.0 mL). The solution is degassed by bubbling argon for 5 min. The vessel is sealed and heated at 90° C. overnight. The reaction mixture is cooled to RT and poured into EtOAc. The organic layer is washed with a saturated aqueous solution of ammonium chloride and brine, dried over MgSO$_4$, filtered and concentrated. Purification by Combi-Flash Rf (0-20% EtOAc/Hexanes as eluent on a 12 g column) affords 18a3 ($t_R$=1.88 min, (M+H)$^+$=350.1).

Step 4:

18a3 (205 mg, 0.59 mmol) is dissolved in EtOH (20 mL) and purged under argon. Pd/C (10% w/w) is added. The mixture is purged under argon and then placed under H$_2$ (1 atm) for 16 h. The reaction mixture is filtered through a pad of celite and concentrated to dryness. Purification by Combi-Flash Rf (0-50% EtOAc/Hexanes as eluent on a 4 g column) affords 18a4 ($t_R$=1.65 min, (M+H)$^+$=298.1).

The following intermediates are prepared analogously to the procedure described in Example 18 starting from the appropriate bromo derivative.

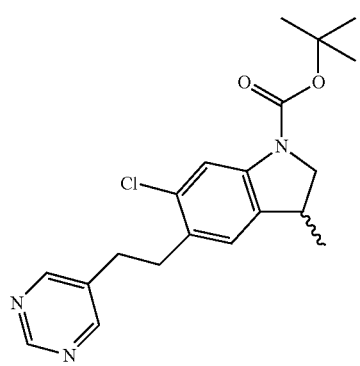

18b4

Example 19

Preparation of 19a2

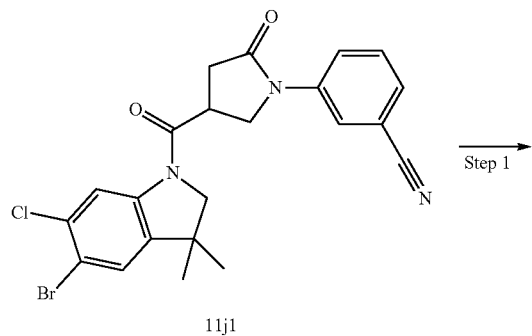

11j1

Step 1 →

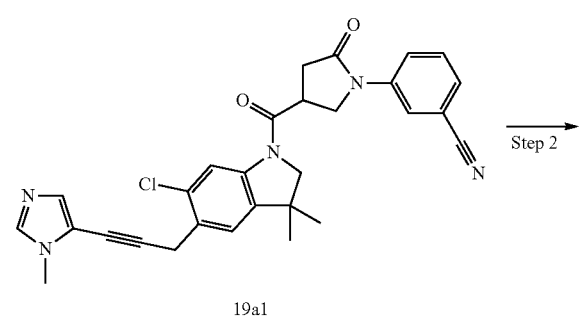

19a1

Step 2 →

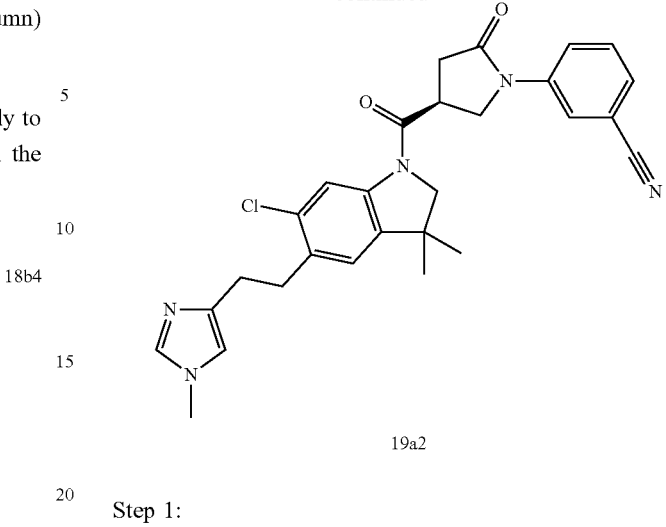

19a2

Step 1:

A pressure vessel equipped with a Teflon stir bar is charged with 11j1 (100 mg, 0.21 mmol), 5-ethynyl-1-methyl-1H-imidazole (28 mg, 0.26 mmol), diethylamine (1094, 1.1 mmol), copper iodide (4 mg, 0.02 mmol), Pd(PPh$_3$)$_4$ (22 mg; 0.02 mmol) and DMF (1 mL). The solution is degassed by bubbling argon for 5 min. The vessel is sealed and heated at 90° C. overnight. The reaction mixture is cooled to RT and poured into EtOAc and water. The residue is filtered and the filtrate is dried under high vacuum to afford 19a1 ($t_R$=1.38 min, (M+H)$^+$=498; 500).

Step 2:

19a1 (25 mg, 0.05 mmol) is dissolved in a mixture of MeOH (1 mL) and THF (1 mL). The slurry is treated with 20% Pd/C w/w (Degussa type E101 NE/W, 4 mg), purged under argon and then placed under H$_2$ (1 atm) for 16 h. The reaction mixture is filtered through an Acrodisc filter and concentrated to dryness. The residue is diluted with DMSO and purified by preparative-HPLC MeCN/H$_2$O (containing 5 mM of ammonium formate). The pure fractions are combined, concentrated, diluted with a mixture of MeCN/H$_2$O, frozen and lyophilized to afford 19a2 as a racemic mixture. The enantiomers are separated by SFC (multiple stacked injections): SFC-MS: Waters Prep 15, Column: IA 10×250 mm at 40° C., Eluent A: CO$_2$, Eluent B: MeOH–2 mM ammonium bicarbonate, Gradient:Isocratic 50:50 CO$_2$:MeOH+2 mM AmBic at 10 mL/min, Back Pressure Regulator: 150 Bars, Run Time: 12 min.

The desired fractions are collected and concentrated in vacuo to afford 19a2 ($t_R$=1.09 min, (M+H)$^+$ 502.1; 504.0).

The following compounds are prepared analogously to the procedure described in Example 19 starting from the appropriate bromoindoline derivative.

| 19b2 | 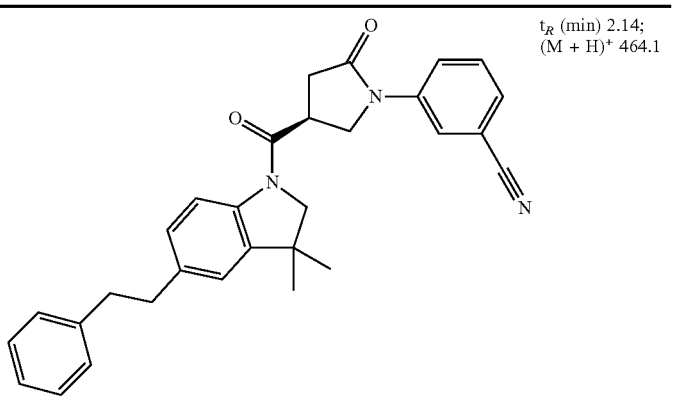 | $t_R$ (min) 2.14; (M + H)⁺ 464.1 |
| --- | --- | --- |
| 19c2 | 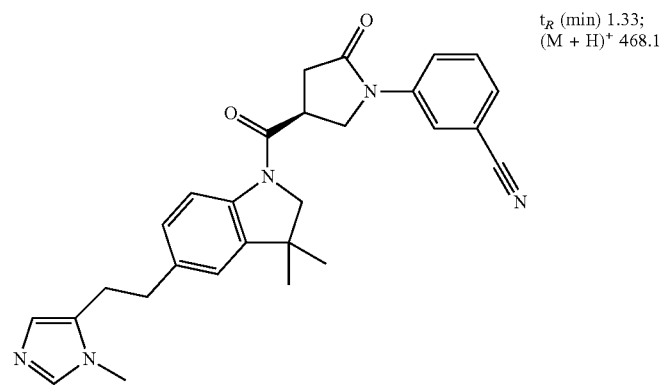 | $t_R$ (min) 1.33; (M + H)⁺ 468.1 |
| 19d2 | 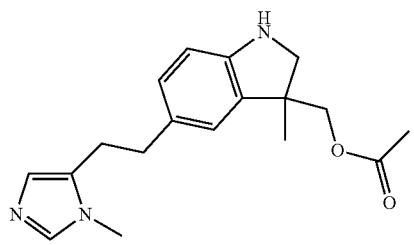 [SMILES: CC(=O)OCC1(C)CNc2ccc(CCc3cncn3C)cc21] | |
Example 20
Preparation of Intermediate 20a1
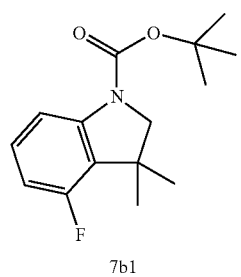
-continued
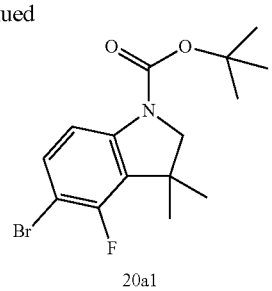
Step 1:
7b1 (450 mg, 1.7 mmol) is dissolved in acetonitrile (55 mL) and 1-bromo-pyrrolidine-2,5-dione (330 mg; 1.9 mmol) is added. The mixture is stirred at RT for 45 min. The reaction mixture is concentrated to about 20 mL of MeCN, diluted with EtOAc, washed with saturated aqueous Na$_2$S$_2$O$_3$, 1N NaOH (3×) and brine, dried over MgSO$_4$, filtered and concentrated to afford 20a1 (t$_R$=2.14 min, (M+H)$^+$ 331; 333).

The following intermediates are prepared analogously to the procedure described in Example 20 starting from the appropriate derivative.

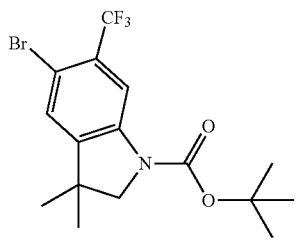
20b1

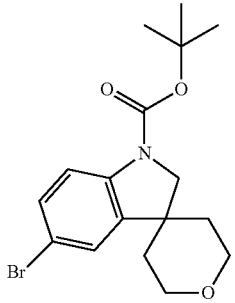
20c1

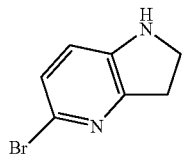
20d1

Example 21

Preparation of Intermediate 21a1

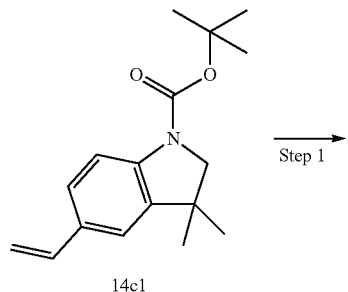
14c1

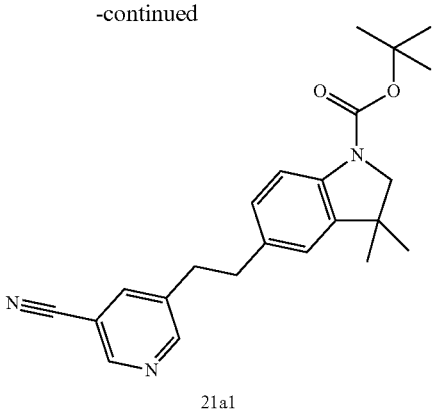
21a1

Step 1:
A solution of 14c1 (42 mg, 0.15 mmol) and 9-BBN (0.5M in THF, 1.2 mL, 0.6 mmol) is stirred at RT for 1 h. 65 μL of water is added and this mixture is stirred at RT for 10 min. A solution of K$_2$CO$_3$ (2M in water, 250 μL, 0.5 mmol) is added and this mixture is stirred for 25 min. A solution of 5-bromo-nicotinonitrile (42 mg, 0.23 mmol) and Pd(PPh$_3$)$_4$ (8.9 mg, 0.01 mmol) in THF (0.4 mL) are added. The solution is degassed by bubbling N$_2$ and stirred under microwave irradiation for 20 min at 120° C. The mixture is concentrated and the residue is dissolved in EtOAc and water. The organic layers are washed with brine, dried over Na$_2$SO$_4$, filtered and concentrated. The crude product is purified by combi-flash RF (4 g column eluting 0-40% EtOAc/Hexanes) to afford 21a1 (t$_R$=1.88 min, (M+H)$^+$ 378.2).

The following intermediates are prepared analogously to the procedure described in Example 21 starting from the appropriate halo and vinylic derivatives.

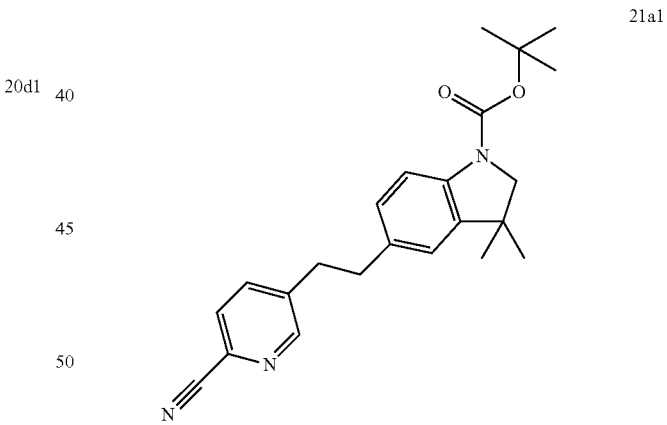
21a1

21b1

-continued

21c1

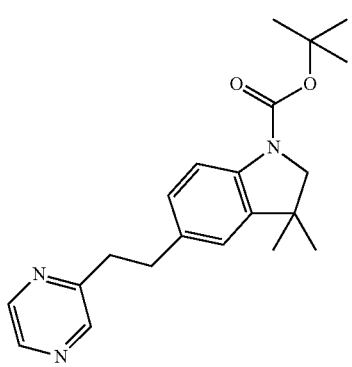

21d1

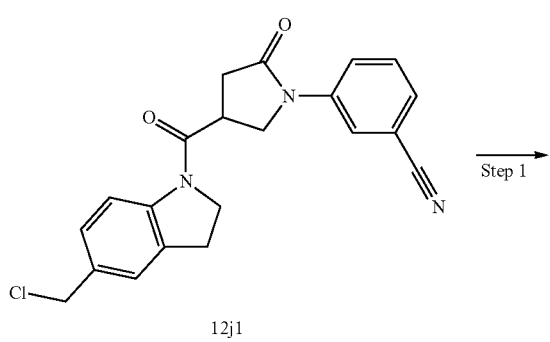

Example 22

Preparation of 22a1

-continued

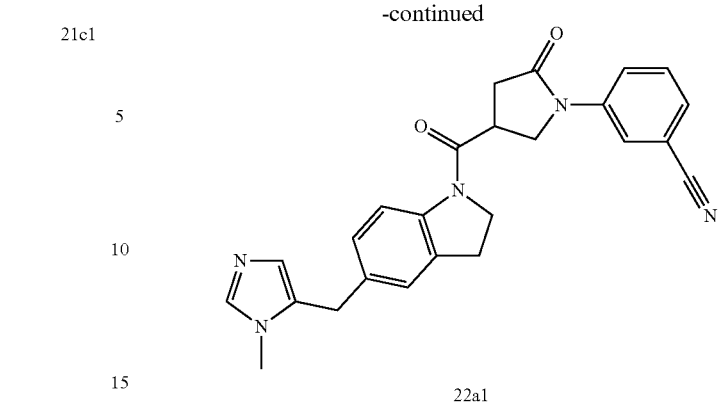

22a1

Step 1:

A pressure vessel equipped with a Teflon stir bar is charged with 12j1 (25 mg, 0.07 mmol), (1-methyl-1H-imidazol-5-yl)boronic acid (17 mg, 0.13 mmol), $K_3PO_4$ (84 mg, 0.39 mmol), Pd(OAc)$_2$ (3 mg; 0.01 mmol), triphenylphosphine (6.9 mg, 0.03 mmol) and DMF (1.6 mL). The solution is degassed by bubbling argon for 5 min. The vessel is sealed and heated under microwave irradiation at 110° C. for 10 min. The reaction mixture is cooled to RT, filtered through an Acrodisc filter and purified by preparative-HPLC MeCN/H$_2$O (containing 5 mM of ammonium formate). The pure fractions are combined, concentrated, diluted with a mixture of MeCN/H$_2$O, frozen and lyophilized to afford 22a1 ($t_R$=1.13 min, (M+H)$^+$ 426.1).

The enantiomers can be separated on SFC-MS using specific conditions from the matrix of conditions described in the general SFC procedures.

The following compounds are prepared analogously to the procedure described in Example 22 starting from the appropriate chloro and boronic acid derivatives.

| 22a2 | 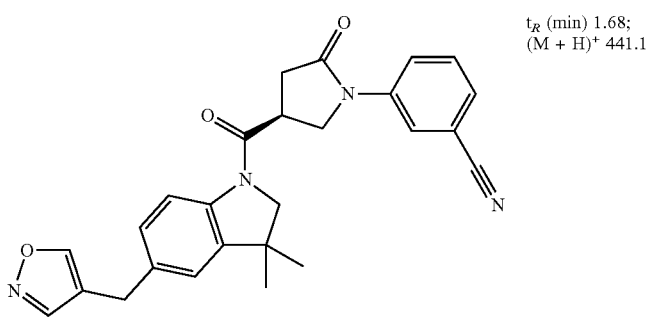 | $t_R$ (min) 1.68; (M + H)$^+$ 441.1 |

| | | |
|---|---|---|
| 22b1 | 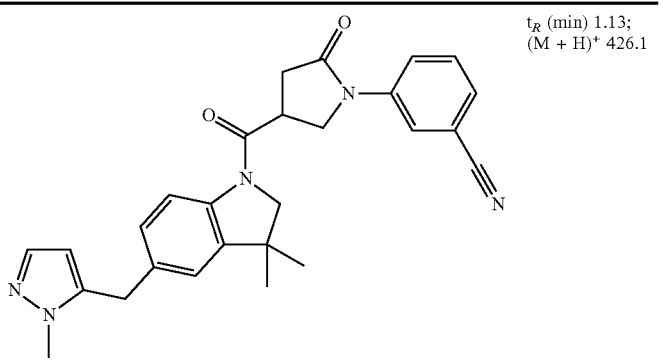 | $t_R$ (min) 1.13; $(M + H)^+$ 426.1 |
| 22c1 | 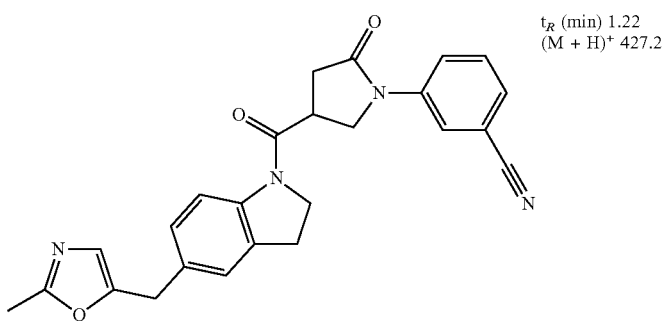 | $t_R$ (min) 1.22 $(M + H)^+$ 427.2 |
| 22d1 | 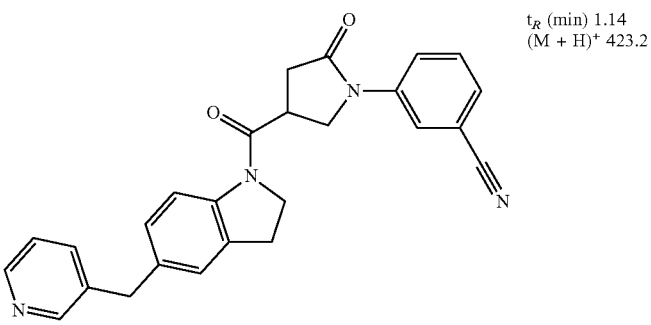 | $t_R$ (min) 1.14 $(M + H)^+$ 423.2 |
| 22e1 | 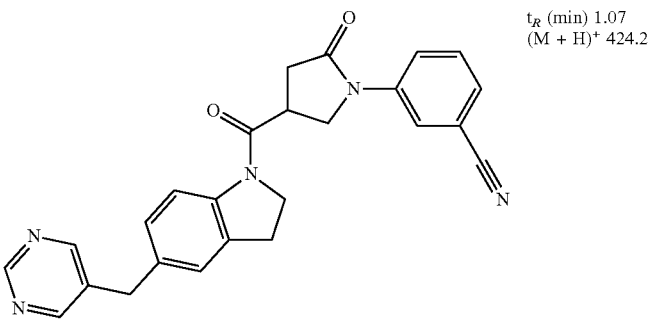 | $t_R$ (min) 1.07 $(M + H)^+$ 424.2 |
| 22f1 | 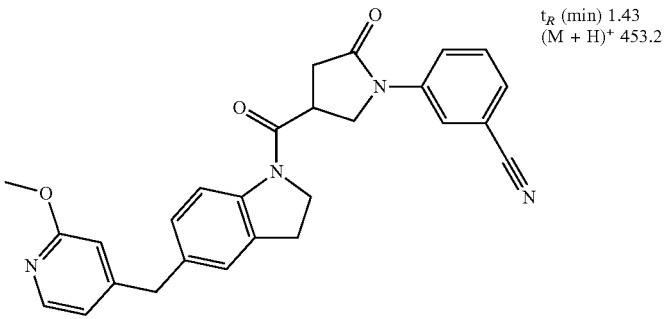 | $t_R$ (min) 1.43 $(M + H)^+$ 453.2 |

| | | |
|---|---|---|
| 22g1 | 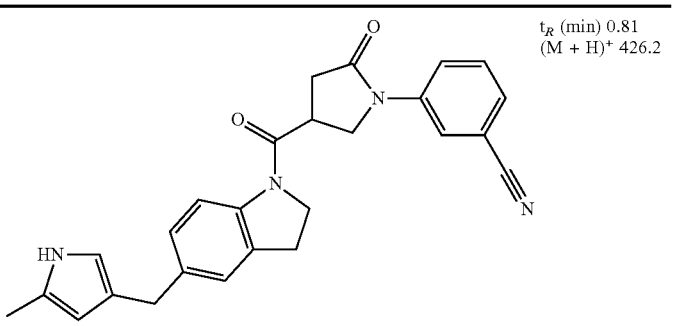 | t_R (min) 0.81<br>(M + H)⁺ 426.2 |
| 22h1 | 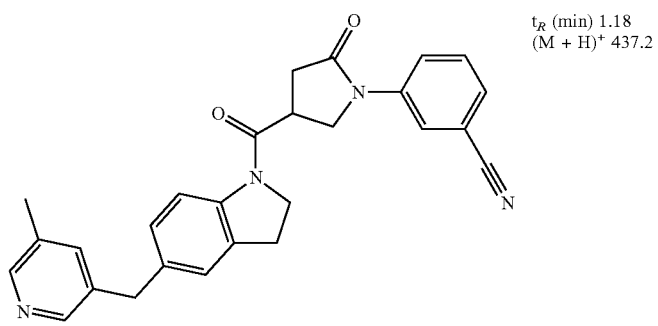 | t_R (min) 1.18<br>(M + H)⁺ 437.2 |
| 22i1 | 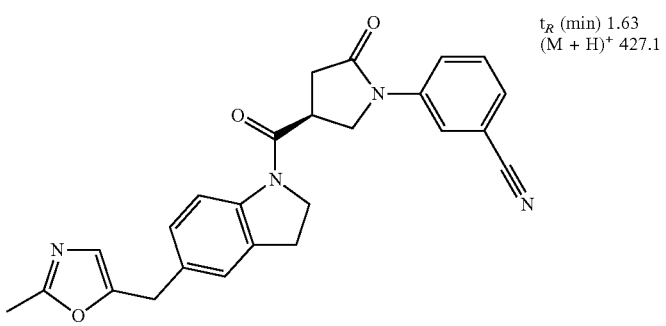 | t_R (min) 1.63<br>(M + H)⁺ 427.1 |
| 22j1 | 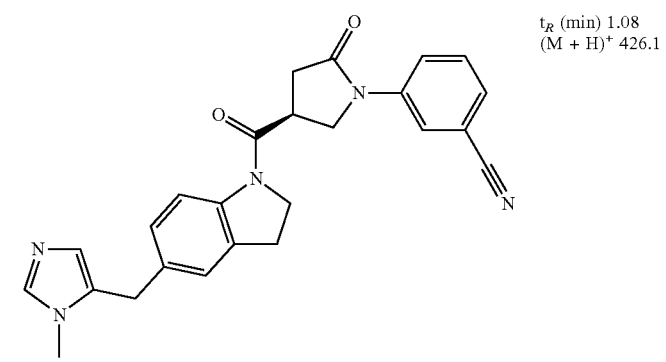 | t_R (min) 1.08<br>(M + H)⁺ 426.1 |
| 22k1 | 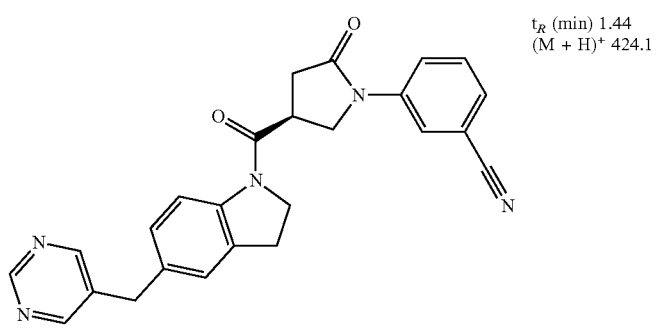 | t_R (min) 1.44<br>(M + H)⁺ 424.1 |

| | | |
|---|---|---|
| 22l1.1 | 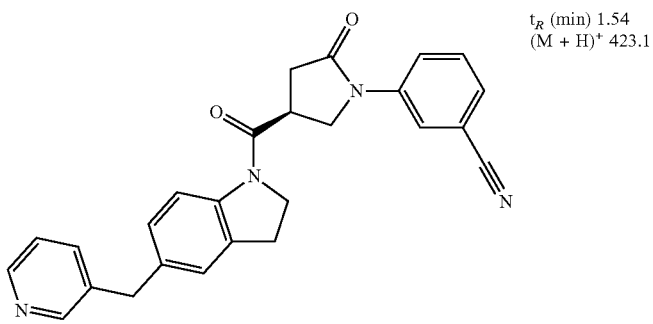 | $t_R$ (min) 1.54<br>$(M + H)^+$ 423.1 |
| 22l1.2 | 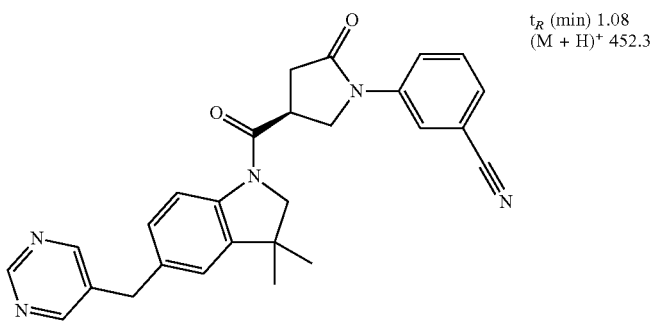 | $t_R$ (min) 1.08<br>$(M + H)^+$ 452.3 |
| 22m1 | 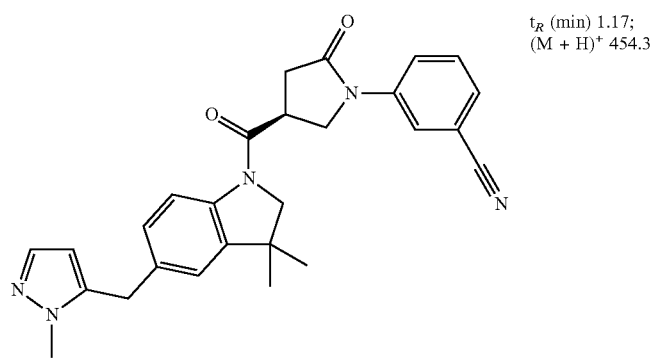 | $t_R$ (min) 1.17;<br>$(M + H)^+$ 454.3 |
| 22n1 | 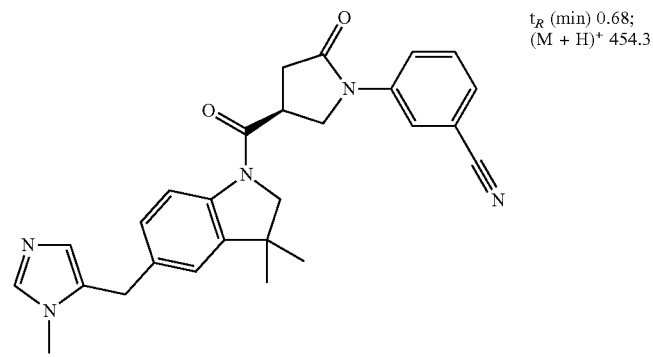 | $t_R$ (min) 0.68;<br>$(M + H)^+$ 454.3 |

-continued
| | | |
|---|---|---|
| 22o1 | 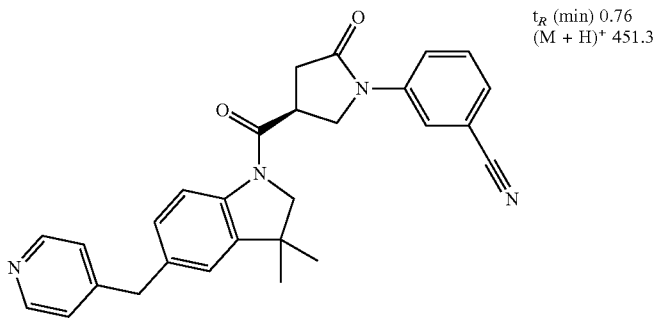 | $t_R$ (min) 0.76<br>$(M + H)^+$ 451.3 |
| 22p1 | 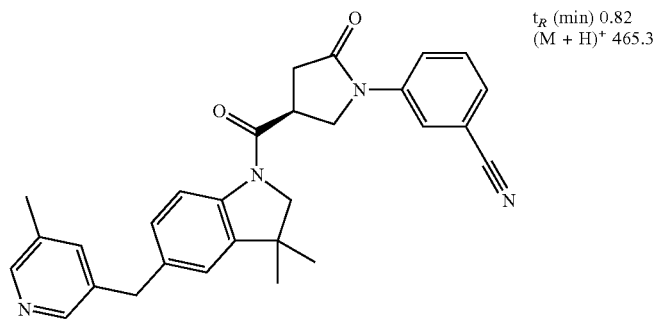 | $t_R$ (min) 0.82<br>$(M + H)^+$ 465.3 |
| 22q1 | 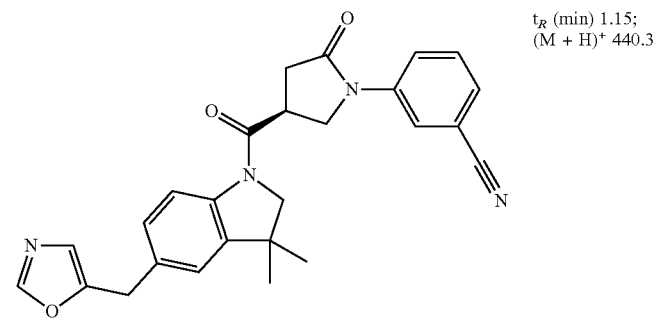 | $t_R$ (min) 1.15;<br>$(M + H)^+$ 440.3 |
| 22r1 | 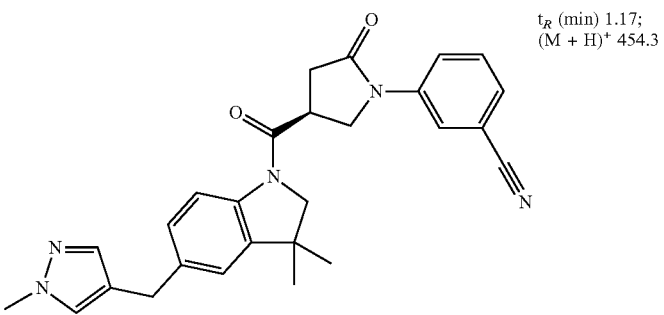 | $t_R$ (min) 1.17;<br>$(M + H)^+$ 454.3 |
| 22s1 | 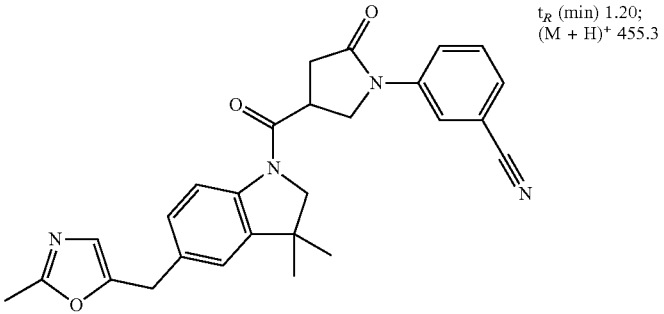 | $t_R$ (min) 1.20;<br>$(M + H)^+$ 455.3 |

-continued
| | | |
|---|---|---|
| 22t1 | 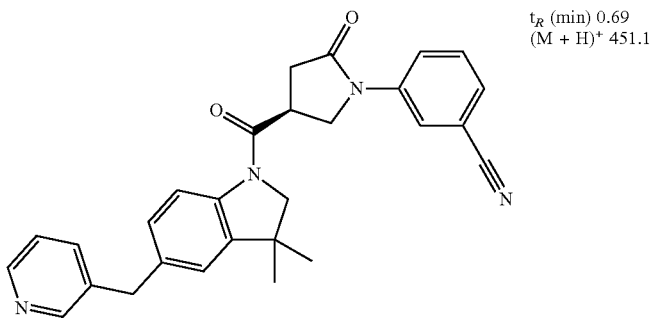 | $t_R$ (min) 0.69 (M + H)$^+$ 451.1 |
| 22u1 | 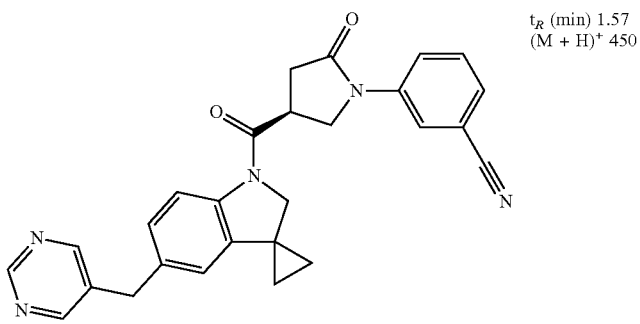 | $t_R$ (min) 1.57 (M + H)$^+$ 450 |
| 22v1 | 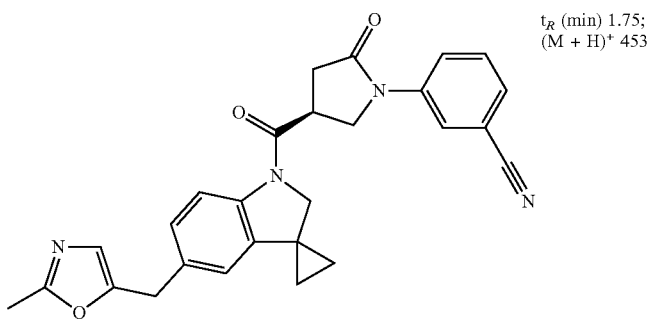 | $t_R$ (min) 1.75; (M + H)$^+$ 453 |
| 22w1 | 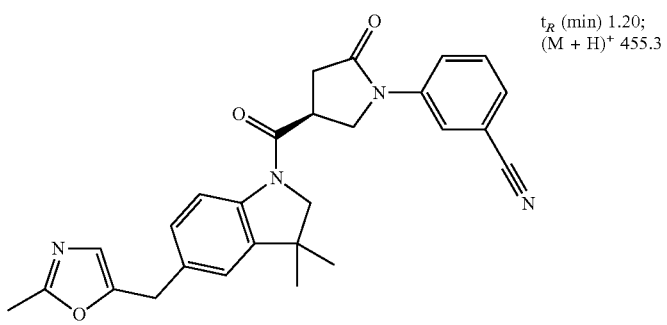 | $t_R$ (min) 1.20; (M + H)$^+$ 455.3 |
| 22x1 | 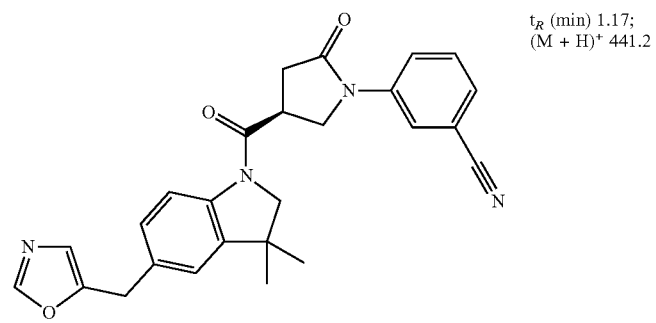 | $t_R$ (min) 1.17; (M + H)$^+$ 441.2 |

-continued
| | | |
|---|---|---|
| 22y1 | 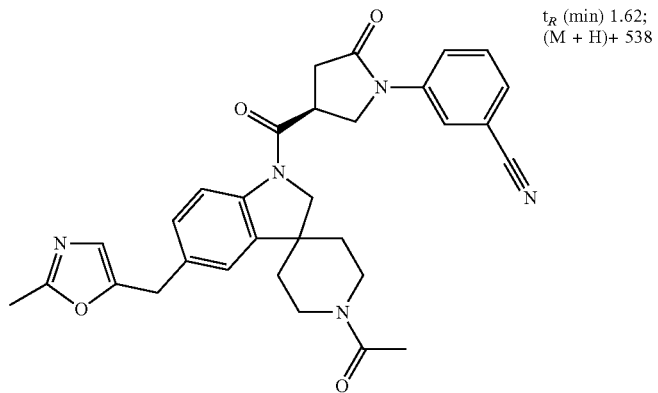 | t$_R$ (min) 1.62;<br>(M + H)+ 538 |
| 22z1 | 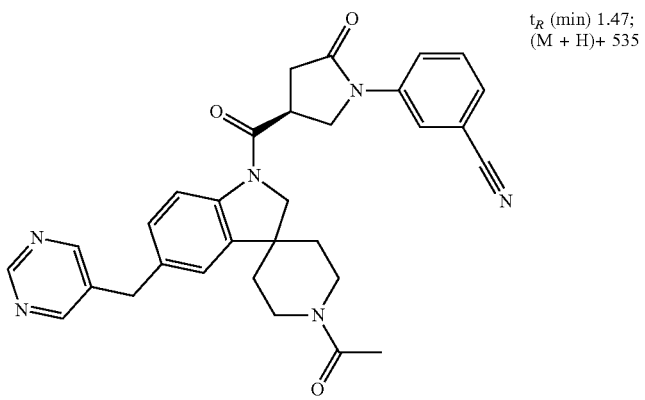 | t$_R$ (min) 1.47;<br>(M + H)+ 535 |
| 22aa1 | 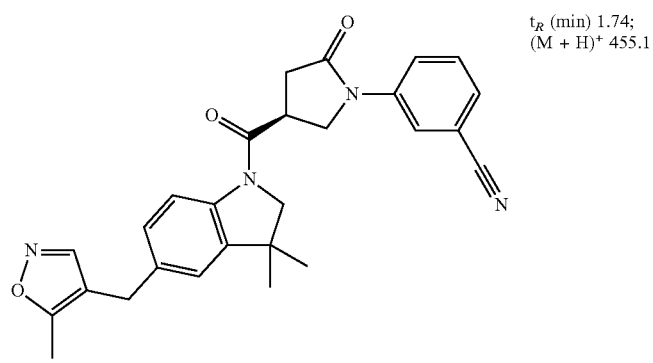 | t$_R$ (min) 1.74;<br>(M + H)$^+$ 455.1 |
| 22bb1 | 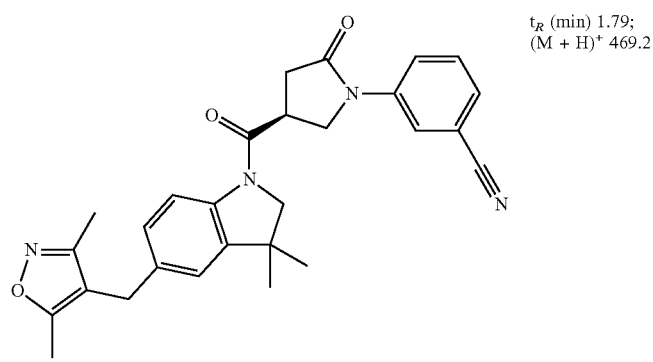 | t$_R$ (min) 1.79;<br>(M + H)$^+$ 469.2 |

22cc1

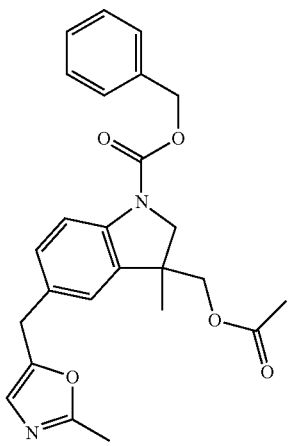 [SMILES: CC(=O)OCC1(C)CN(C(=O)OCc2ccccc2)c2ccc(Cc3cnc(C)o3)cc21]

22dd1

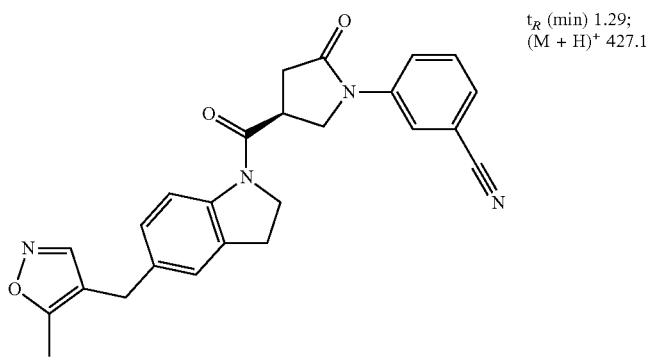

$t_R$ (min) 1.29;
$(M + H)^+$ 427.1

22ee1

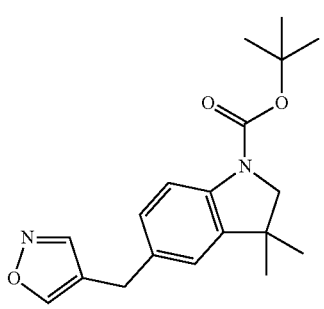 [SMILES: CC(C)(C)OC(=O)N1CC(C)(C)c2cc(Cc3cnoc3)ccc21]

Example 23

Preparation of Intermediate 23a2

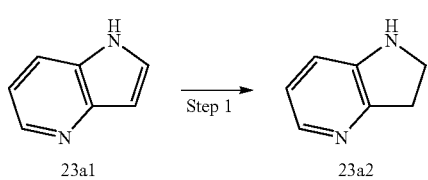 [SMILES: c1cnc2cc[nH]c2c1 ; c1cnc2c(c1)NCC2]

Step 1:

To a solution of 23a1 (Matrix, 8 g, 68 mmol) in anhydrous THF (68 mL), a 1M solution of $BH_3$ in THF (410 mL, 410 mmol) is added over the period of 15 min at RT. This mixture is stirred under reflux for 6 h. After cooling to RT, the reaction mixture is neutralized with addition of MeOH and concentrated under reduced pressure. The residue is dissolved in MeOH and refluxed overnight. The mixture is concentrated. The residue is dissolved in EtOAc, washed with water and brine, and dried over $Na_2SO_4$. After filtration and evaporation of the solvent, the crude material is purified by flash column chromatography (silica gel 230-400 mesh; 0-3% gradient of MeOH in EtOAc) to provide 23a2.

Example 24

Preparation of 24a1

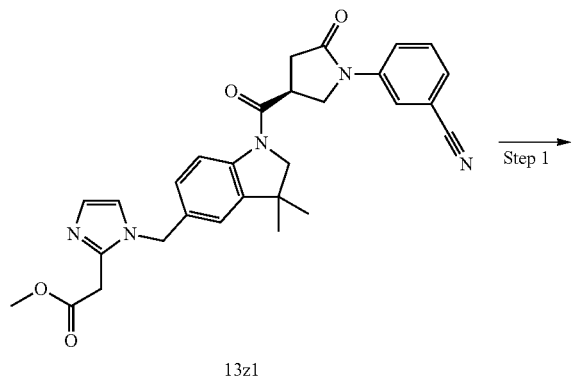

13z1

Step 1

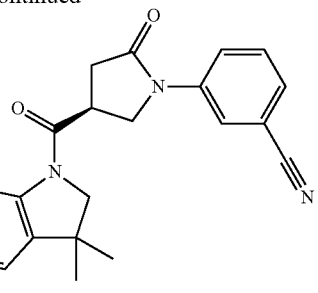

24a1

Step 1:

To 13z1 (51 mg, 0.10 mmol) in a mixture of MeOH and THF is added an aqueous solution of LiOH (2.5 M, 100 μL, 0.26 mmol). The reaction mixture is stirred at RT for 16 h, then DMSO and aqueous ammonium formate solution (5 mM) are added. The solution is filtered through an Acrodisc filter and purified by preparative-HPLC MeCN/$H_2O$ (containing 5 mM of ammonium formate). The pure fractions are combined, concentrated, diluted with a mixture of MeCN/$H_2O$, frozen and lyophilized to afford 24a1 ($t_R$=0.82 min, $(M+H)^+$ 498.3).

The following compounds are prepared analogously to the procedure described in Example 24 starting from the appropriate ester derivative.

24b1

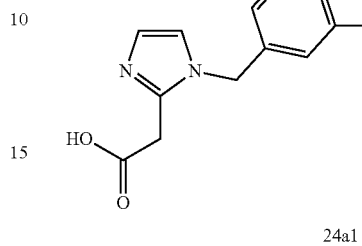

24c1

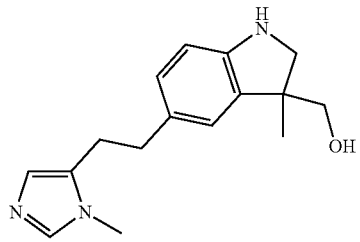 [SMILES: Cn1cncc1CCc1ccc2c(c1)C(C)(CO)CN2]

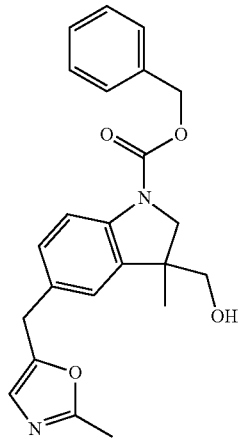 [SMILES: Cc1ncc(Cc2ccc3c(c2)C(C)(CO)CN3C(=O)OCc2ccccc2)o1]

| | | |
|---|---|---|
| 24d1 | 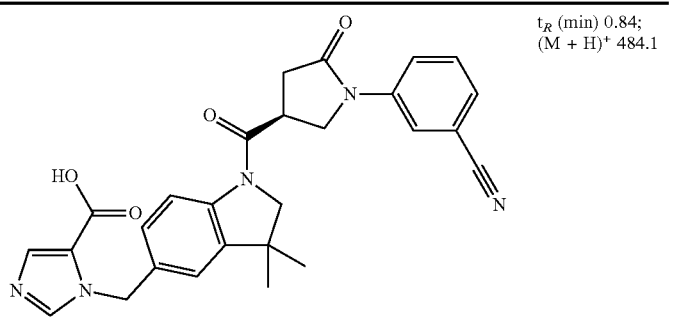 | $t_R$ (min) 0.84;<br>(M + H)+ 484.1 |
| 24e1 | 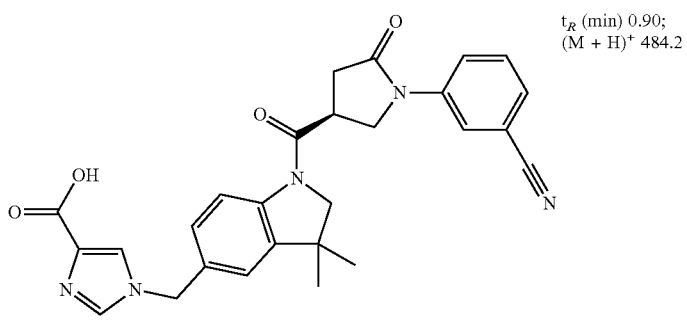 | $t_R$ (min) 0.90;<br>(M + H)+ 484.2 |
| 24f1 | 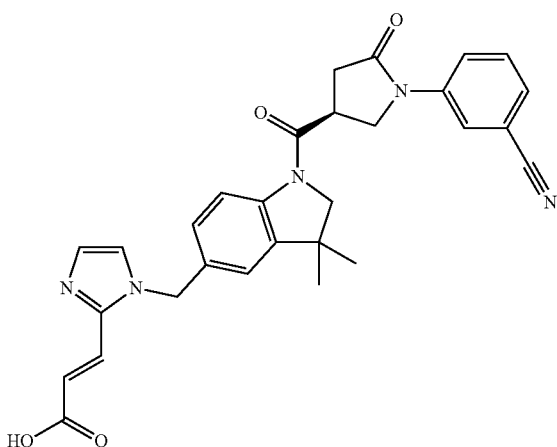 [SMILES: CC1(C)CN(C(=O)[C@H]2CC(=O)N(c3cccc(C#N)c3)C2)c2ccc(Cn3ccnc3/C=C/C(=O)O)cc21] | |
Example 25
Preparation of Intermediate 25a6
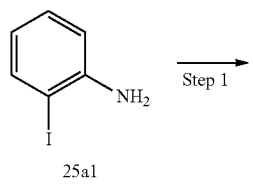
25a1
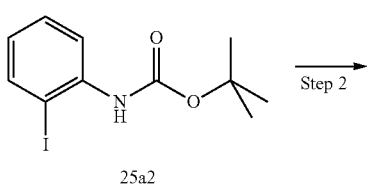
25a2
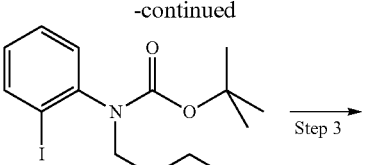
25a3
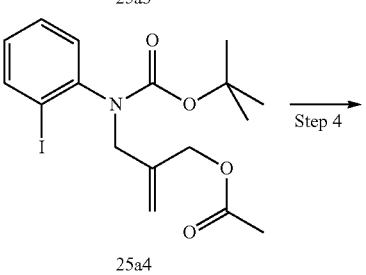
25a4

-continued

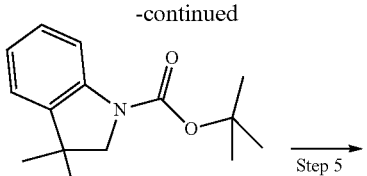

25a5

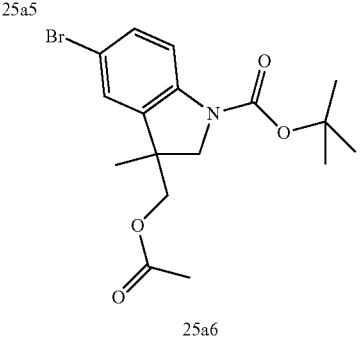

25a6

Step 1:
2-iodo-phenylamine 25a1 (Aldrich, 5 g, 23 mmol) dissolved in tetrahydrofuran (240 mL) is treated with boc anhydride (15 g; 68 mmol) and DMAP (280 mg, 2.3 mmol). The mixture is refluxed overnight. The reaction mixture is cooled to RT, diluted with EtOAc, washed with an aqueous solution of 10% citric acid, water (2×) and brine, dried over MgSO$_4$, filtered and concentrated.

The crude bis-boc product is taken into MeOH (240 mL), treated with potassium carbonate (9.5 g; 68 mmol) and refluxed for 2 h. The reaction mixture is cooled to RT and concentrated. The crude product is dissolved in EtOAc and an aqueous solution of 10% citric acid is added. The layers are separated and the organic layer is washed with water and brine, dried over MgSO$_4$, filtered and concentrated to afford 25a2 ($t_R$=1.78 min, (M−H)$^+$ 317).

Step 2:
25a2 (2 g, 6.3 mmol) is dissolved in DMF (40 mL) and cooled to 0° C. NaH (60% in mineral oil, 780 mg; 19 mmol) is added. The mixture is stirred for 15 min at 0° C. and then 15 min at RT. 3-chloro-2-(chloromethyl)-1-propene (Aldrich, 2.3 mL; 20 mmol) is added and the mixture is stirred at RT for 3 h. The reaction mixture is neutralized with water and EtOAc then diluted with EtOAc and water. The layers are separated and the organic layer is washed with water (4×) and brine, dried over MgSO$_4$, filtered and concentrated to afford 25a3 ($t_R$=2.13 min).

Step 3:
25a3 (2.6 g, 6.3 mmol) is dissolved in DMF (20 mL) and potassium acetate (800 mg, 8.2 mmol) is added. The mixture is stirred for 16 h at 65° C. The reaction mixture is neutralized with addition of water and extracted with EtOAc (3×). The combined organic layers are washed with water (4×) and brine, dried over MgSO$_4$, filtered and concentrated. Purification by flash chromatography eluting 10% EtOAc/Hex affords 25a4 ($t_R$=1.78 min, (M-OtBu)$^+$ 375).

Step 4:
25a4 (600 mg; 1.4 mmol) is dissolved in toluene (30 mL). Triphenyltinhydride (590 mg; 1.7 mmol) is added followed by ACCN (51 mg; 0.21 mmol) and the mixture is degassed by bubbling nitrogen for 15 min. The mixture is stirred at 80° C. for 1 h. Silica is added and the solvent is evaporated. Purification by flash chromatography eluting 3-5% EtOAc/Hex affords 25a5.

Step 5:
25a5 (280 mg, 0.9 mmol) is dissolved in acetonitrile (4 mL) and 1-bromo-pyrrolidine-2,5-dione (170 mg; 0.9 mmol) is added. The mixture is stirred at RT for 60 min. The reaction mixture is concentrated, diluted with EtOAc, washed with brine, dried over MgSO$_4$, filtered and concentrated to afford 25a6 ($t_R$=1.88 min).

Example 26

Preparation of Intermediate 26a1

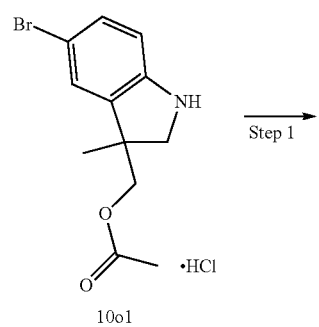

10o1

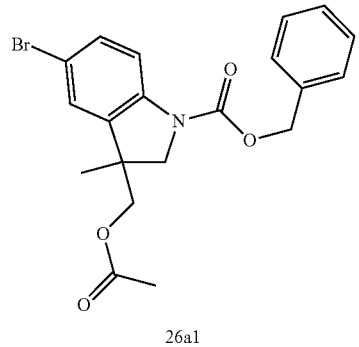

26a1

Step 1:
10o1 (109 mg, 0.38 mmol) is dissolved in acetonitrile (5.5 mL) and potassium carbonate (110 mg, 0.77 mmol) and benzyl chloroformate (60 µL, 0.42 mmol) are added. The mixture is stirred for 2 h, diluted with EtOAc, washed with water, 0.5N HCl and brine, dried over MgSO$_4$, filtered and concentrated. The crude product is purified by combi-flash RF (4 g column eluting 10% EtOAc/Hexanes) to afford 26a1 ($t_R$=1.88 min, (M+H)$^+$ 417.9; 419.9).

Example 27

Preparation of Intermediate 27a1

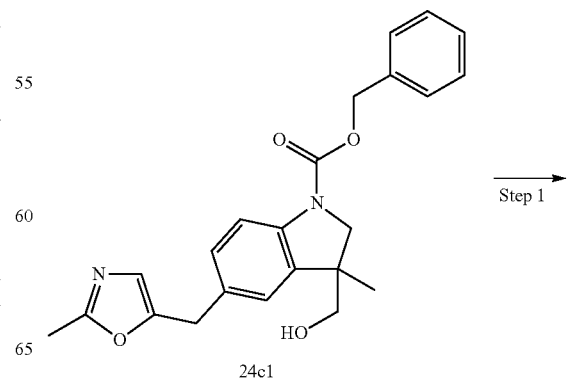

24c1

-continued

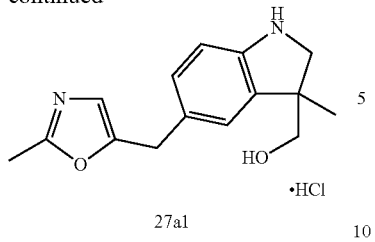

27a1 ·HCl

Step 1:
24c1 (26 mg, 0.07 mmol) is dissolved in THF (1 mL) and MeOH (1 mL) and purged under argon. Pd/C (10% w/w, catalytic) is added. The mixture is purged under argon and then placed under H$_2$ (1 atm) for 16 h. The reaction mixture is filtered through a pad of celite and washed with MeOH. The filtrate is concentrated to dryness. HCl in diethyl ether is added and the solid is collected to afford 27a1 ($t_R$=1.01 min).

Example 28

Preparation of Intermediate 28a2

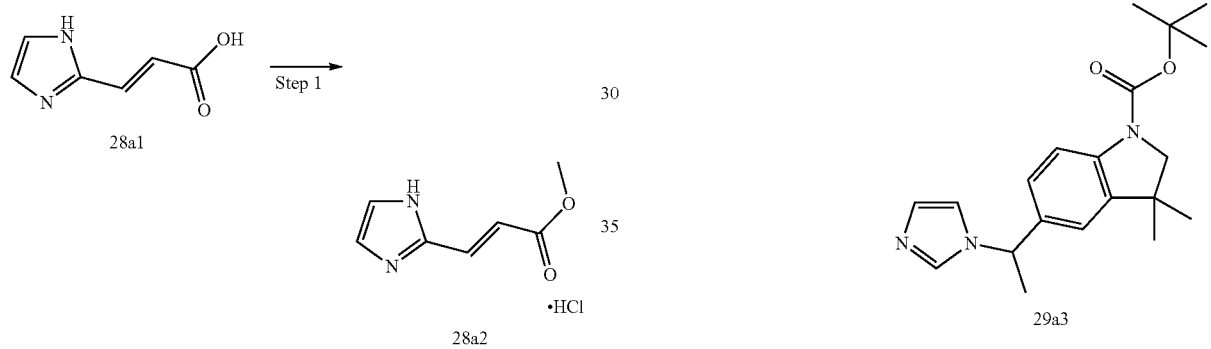

28a1

28a2 ·HCl

Step 1:
The acid 28a1 (Aldrich, 130 mg, 0.9 mmol) is weighed directly in an 8 mL vial, dissolved with MeOH (3 mL) and a 4M HCl solution in 1,4-dioxane (0.5 mL; 2 mmol) is added. The reaction mixture is allowed to stir overnight at 60° C. The solvent is removed under reduced pressure to afford 28a2.

Example 29

Preparation of Intermediate 29a1

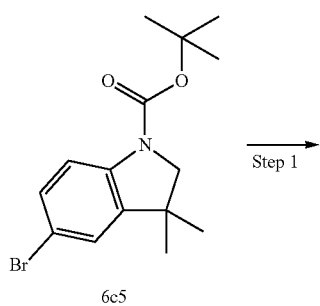

6c5

-continued

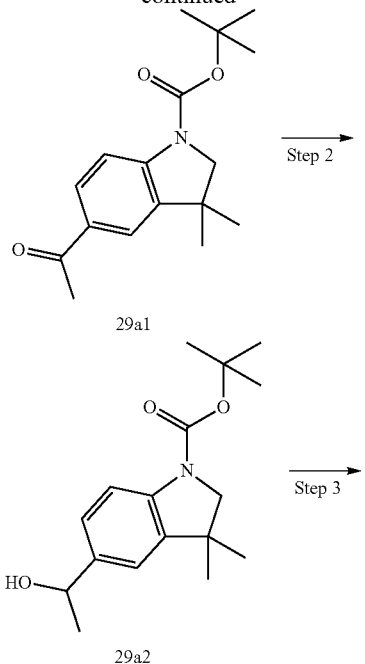

29a1

29a2

29a3

Step 1:
A pressure vessel equipped with a Teflon stir bar is charged with 6c5 (305 mg, 0.93 mmol), tributyl-(1-ethoxy-vinyl)-stannane (0.41 mL, 1.2 mmol), PdCl$_2$(PPh$_3$)$_2$ (98 mg; 0.14 mmol) and DMF (4.5 mL). The solution is degassed by bubbling argon for 5 min. The vessel is sealed and heated under microwave irradiation at 145° C. for 30 min. The reaction mixture is cooled to RT. A 1N HCl solution (2.8 mL, 2.8 mmol) is added and this mixture is stirred at RT for 1 h. EtOAc is added. The mixture is filtered over Celite and concentrated in vacuo. EtOAc and water are added, the layers separated and the aqueous layer is extracted with EtOAc (2×). The combined organic layers are washed with water (2×), brine, dried over MgSO$_4$, filtered and concentrated. The crude product is purified by combi-flash RF (12 g column eluting 0-20% EtOAc/Hexanes) to afford 29a1 ($t_R$=2.04 min, (M+H)$^+$ 290.3).

Step 2:
To 29a1 (60 mg, 0.21 mmol) in MeOH (2 mL) is added sodium borohydride (16 mg, 0.41 mmol) and the mixture is stirred overnight at RT. The reaction mixture is neutralized with a saturated aqueous solution of NH$_4$Cl. EtOAc is added and the aqueous layer is extracted with EtOAc (3×). The organic layers are washed with brine, dried with MgSO$_4$, filtered and concentrated. The crude product is purified by combiflash RF (4 g column using 0-30% EtOAc/Hex) to afford 29a2 (($t_R$=1.91 min, (M-OH)$^+$ 274.2).

Step 3:

To 29a2 (50 mg, 0.17 mmol) in THF (2 mL) is added di-imidazol-1-yl-methanone (56 mg, 0.34 mmol) and the mixture is stirred overnight at reflux. The reaction mixture is cooled to RT. EtOAc and water are added and the layers are separated. The aqueous layer is extracted with EtOAc (3×). The organic layers are washed with brine, dried with MgSO$_4$, filtered and concentrated. The crude product is purified by combiflash RF (4 g column using 0-8% MeOH/DCM) to provide 29a3 ($t_R$=1.66 min, (M+H)$^+$ 342.3).

Example 30

Preparation of Intermediate 30a1

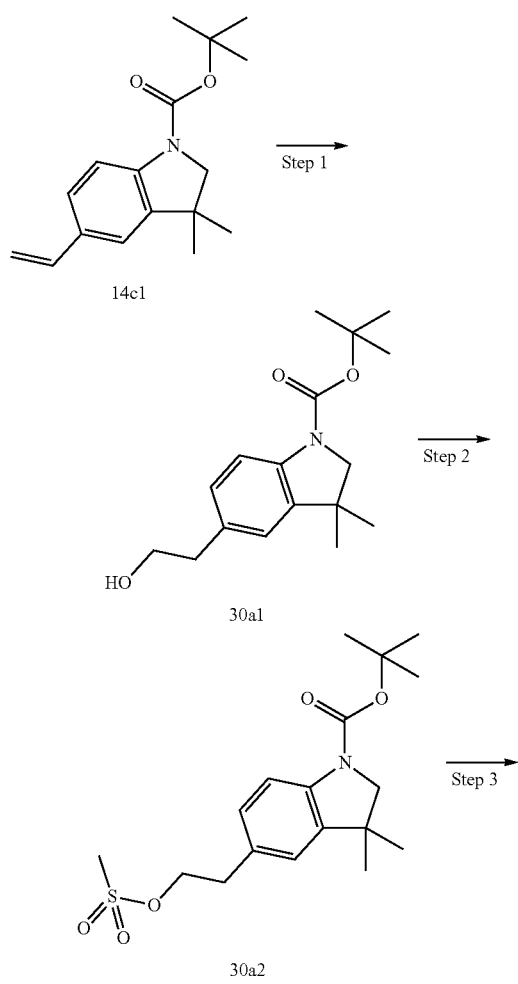

Step 1:

A solution of the alkene 14c1 (200 mg, 0.73 mmol) and 9-BBN (0.5M in THF, 7.3 mL, 3.7 mmol) in THF (7 mL) is stirred at 0° C. for 0.5 h and at RT for 3 h. The mixture is cooled to 0° C. and 1N NaOH solution (7.3 mL, 7.3 mmol) and hydrogen peroxide solution (30% in water, 3.3 mL, 29 mmol) are added. The mixture is allowed to reach RT and stirred for 2 h. The reaction mixture is neutralized with an aqueous solution of 10% Na$_2$S$_2$O$_3$ at 0° C. The mixture is stirred at RT for 10 min and concentrated. The aqueous residue is extracted with EtOAc (3×). The combined organic layers are washed with brine, dried with MgSO$_4$, filtered and concentrated. The crude product is purified by Combiflash RF (12 g column eluting 0-40% EtOAc/Hexanes) to afford 30a1 ($t_R$=1.95 min, (M+H)$^+$ 292.3).

Step 2:

A solution of the alcohol 30a1 (190 mg, 0.63 mmol) and triethylamine (0.11 mL, 0.82 mmol) in DCM (3 mL) is stirred at 0° C. and methanesulfonyl chloride (54 µL, 0.7 mmol) is added. The mixture is allowed to reach RT and stirred for 16 h. The reaction mixture is poured into a mixture of DCM and water and the layers are separated. The aqueous layer is extracted with DCM (3×). The combined organic layers are washed with brine, dried with MgSO$_4$, filtered and concentrated. The crude product is purified by Combiflash RF (12 g column eluting 0-40% EtOAc/Hexanes) to afford 30a2 ($t_R$=1.97 min, (M+H)$^+$ 370.2).

Step 3:

To a solution of 1H-pyrazole (Aldrich, 18 mg, 0.27 mmol) in DMF (1.5 mL) at 0° C., is added sodium hydride (60%, 11 mg, 0.27 mmol). This mixture is stirred at RT for 20 min. 30a2 (90 mg, 0.24 mmol) in DMF (1 mL) is added and the mixture is stirred for 1 h. The reaction mixture is poured into a mixture of EtOAc and water and layers are separated. The aqueous layer is extracted with EtOAc (3×). The combined organic layers are washed with water (2×), brine, dried with MgSO$_4$, filtered and concentrated. The crude product is purified by Combiflash RF (12 g column eluting 0-40% EtOAc/Hexanes) to afford 30a3 ($t_R$=2.06 min, (M+H)$^+$ 342.0).

The following intermediates are prepared analogously to the procedure described in Example 30 starting from the appropriate alkene and azole derivatives.

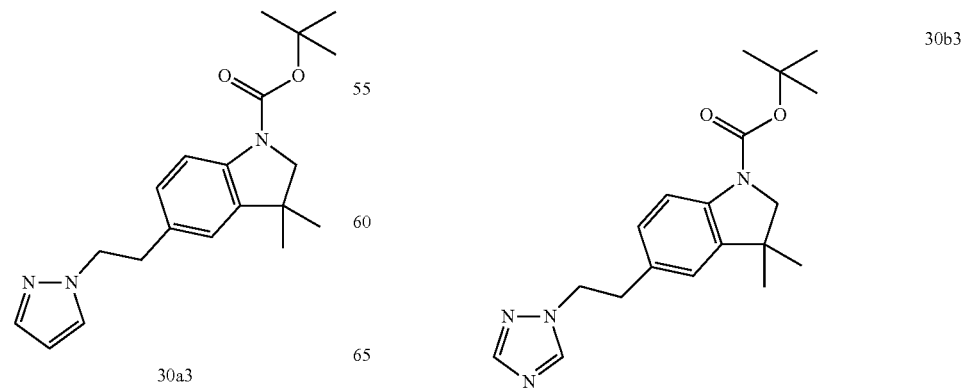

Example 31

Preparation of 31a1

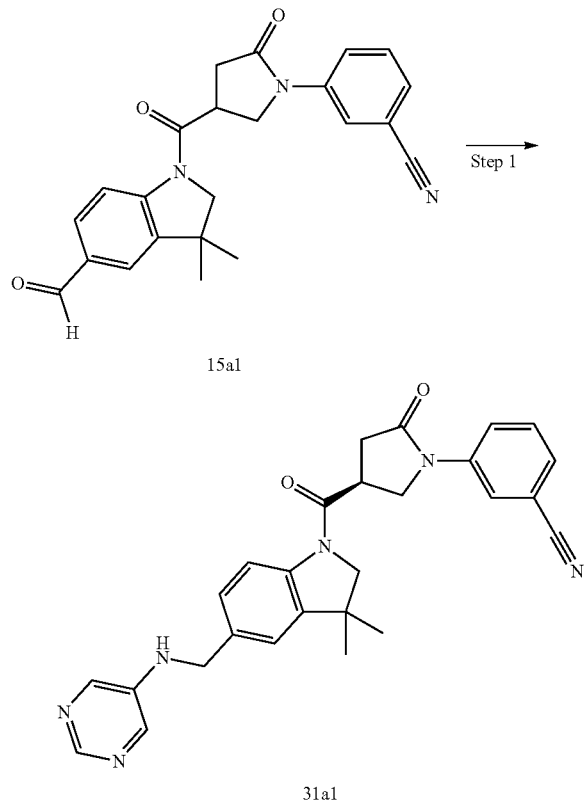

Step 1:

A 0.5-2.0 mL microwave vessel equipped with a Teflon stir bar is charged with 15a1 (20 mg; 0.05 mmol), pyrimidin-5-ylamine (25 mg; 0.26 mmol), a mixture of 2-MeTHF:AcOH 95:5 (0.80 mL) and SiliaBond Cyanoborohydride (100 mg; 0.1 mmol). The vessel is capped and heated under microwave irradiation at 120° C. for 10 min. The reaction mixture is filtered through an Acrodisc filter (DMSO rinsed) and purified by preparative HPLC (Sunfire column; MeCN/AmFor at 45° C.). The desired fractions are collected and concentrated. The enantiomers are separated by SFC (multiple stacked injections): SFC-MS: Waters Prep 100, Column: IB 10×250 mm at 40° C., Eluent A:$CO_2$, Eluent B:MeOH, Gradient:Isocratic 50:50 $CO_2$:MeOH at 50 mL/min, Back Pressure Regulator: 150 Bars, Run Time: 10 min.

The desired fractions are collected and concentrated in vacuo afford to afford 31a1 ($t_R$=1.01 min, (M+H)$^+$ 467.3).

EXAMPLE A

Expression Vector, Protein Expression and Purification

The codon optimized UL54 HCMV polymerase gene from strain AD169 for expression in insect cells is obtained from DNA 2.0 (Menlo Park, Calif.) and subcloned in 3' of the Glutathione-S-transferase (GST) gene in a pFastBac-derived vector. Bacmids and baculoviruses are generated and expression performed in Sf21 insect cells cultured in SF900 II SFM media. Infection using the baculoviruses is performed using an MOI of 5-10 and the cells are harvested 48 h post-infection and frozen.

Reagents and Materials (Equivalents are Acceptable):

| Product | Company | Catalog # | Storage |
|---|---|---|---|
| SF900 II SFM media | Invitrogen | 10902104 | 4° C. |
| Tris | Sigma | T1503 | RT |
| TCEP | Thermo Fisher Scientific | 77720 | 4° C. |
| EDTA | Ambion | AM9262 | RT |
| NaCl | Sigma | S6191 | RT |
| Glycerol | Thermo Fisher Scientific | BP229-4 | RT |
| PMSF | VWR | PB0425 | RT |
| Leupeptin | Cedarlane | N-1000.0025 | −20° C. |
| Antipain | MP Biomedicals | 152843 | −20° C. |
| Pepstatin A | MP Biomedicals | 195368 | −20° C. |
| Glutathione | Thermo Fisher Scientific | BP229-4 | RT |
| Glutathione Sepharose 4B | GE Healthcare | 17-0756-05 | 4° C. |
| HiTrap DEAE-Sepharose FF dolumn | GE Healthcare | 17-5055-01 | 4° C. |

All purification procedures are performed at 4° C. The cell pellet from 1 L of culture (1×10$^9$ cells) is resuspended in 25 mL of 50 mM Tris pH 7.5, 1 mM TCEP, 0.1 mM EDTA, 150 mM NaCl, 10% Glycerol, 1 mM PMSF, 2 μg/mL Leupeptin, 2 μg/mL Antipain, 2 μg/mL Pepstatin A. The solution is homogenized using a Dounce tissue grinder. Following homogenization, the volume is increased to 40 mL followed by centrifugation at 750×g for 5 min to remove nuclei. The supernatant is then transferred and 3 cc of 50% slurry of glutathione-sepharose 4B resin is added and the mixture is incubated on a rotator for 1 h. The slurry is centrifuged at 500 g for 5 min. The supernatant is discarded and the pellet is resuspended in 10× volume of wash buffer (50 mM Tris pH 7.5, 1 mM TCEP, 0.1 mM EDTA, 150 mM NaCl, 10% Glycerol) and incubated for 5 min. The slurry is centrifuged at 500 g for 5 min and the supernatant is discarded. The wash step is performed 5 times. The elution is performed by adding 1.5 volume of elution buffer (50 mM Tris pH 7.5, 1 mM TCEP, 0.1 mM EDTA, 150 mM NaCl, 10% Glycerol, 20 mM glutathione) and then incubating on a rotator for 15 min. The slurry is centrifuged at 500 g for 5 min and the supernatant is removed and kept. The elution step is performed four times. The supernatant are pooled and centrifuged at 500×g for 5 min to remove resin particles and are frozen at −80° C.

The frozen protein is thawed and the NaCl concentration reduced to 37.5 mM by the addition of 3 volumes of DEAE buffer A (50 mM Tris pH 7.5, 1 mM TCEP, 0.1 mM EDTA, 10% Glycerol). The protein is loaded on a HiTrap DEAE-Sepharose FF column and eluted using a gradient with DEAE buffer B (50 mM Tris pH 7.5, 1 mM TCEP, 0.1 mM EDTA, 10% Glycerol, 1 M NaCl). UL54 eluted at 140 mM NaCl. The DEAE fractions are pooled, frozen and stored at −80° C. The protein concentration is determined by OD$_{280}$ ($A_{280}$=1.03 mg/mL).

Example B

HCMV Polymerase LANCE TR-FRET Assay

This non-radiometric assay determines the enzymatic activity of purified recombinant HCMV polymerase from strain AD169 (UL54) using a Digoxigenin-labeled oligonucleotide priming a heteropolymeric template. The enzymatic activity is determined by incorporating Biotin-dUTP in the nascent complementary strand. The signal is generated by Fluorescence Resonance Energy Transfer from the donor (Anti-Digoxigenin-Europium Chelate binding with the primer) to the acceptor Streptavidin-AlloPhycoCyanin (SA-APC) binding to the biotin of the labeled nucleotides incorporated in proximity.

Reagents and Materials (Equivalents are Acceptable):

| Product | Company | Catalog # | Storage |
|---|---|---|---|
| 384-well white PP | SeaHorse | S30033W | RT |
| 1M Hepes | Invitrogen | 15630-080 | 4° C. |
| 10 mg/mL BSA | New England Biolabs | B9001S | −20° C. |
| 0.5M TCEP pH 7.0 | Thermo Fisher Scientific | 77720 | 4° C. |
| 0.5M EDTA pH 8.0 | Ambion | AM9262 | RT |
| DMSO | VWR (EMD Chemicals) | CAMX1457-6 | RT |
| KCl | Sigma | P9541 | RT |
| NaCl | Sigma | S6191 | RT |
| MgCl$_2$ | VWR (EMD Chemicals) | CAMX0045-1 | RT |
| Glycerol | Thermo Fisher Scientific | BP229-4 | RT |
| Tris | Sigma | T1503 | RT |
| 10% Tween-20 | Bio-Rad | 161-0781 | RT |
| Heteropolymeric template | Integrated DNA Technologies | Custom | −20° C. |
| Digoxigenin-labeled primer | Integrated DNA Technologies | Custom | −20° C. |
| 100 mM Deoxynucleotide Solution | New England Biolabs | N0446S | −20° C. |
| 1 mM Biotin-16-dUTP | Roche | 11093070910 | −20° C. |
| Streptavidin-APC | PerkinElmer | CR130-100 | 4° C. |
| Anti-Dig-Europium | PerkinElmer | Custom | 4° C. |
| GST-UL54 | Purified as described in Example A | | −80° C. |

Preparation of Compounds:

Serial dilutions of the DMSO stock compound solution are performed using DMSO in columns 2-11 and 14-23. DMSO alone is present in columns 1, 12, 13 and 24. Three μL of the DMSO serial dilutions is transferred and diluted using 21 μL of compound dilution buffer (10 mM Hepes pH 7.5, 25 mM KCl, 5 mM MgCl$_2$, 1 mM TCEP) to obtain 12.5% DMSO. 4 μL per well of the 12.5% DMSO serial dilution compound solution is added to the assay plate. The plate is centrifuged at 200×g for 30 sec.

LANCE TR-FRET Assay:

The assay conditions are the following: 10 mM HEPES pH 7.5, 25 mM KCl, 7.5 mM NaCl, 5 mM MgCl$_2$, 0.2 mg BSA/mL, 1 mM TCEP, 1.5% glycerol, 5% DMSO, 235 nM dATP, 350 nM dCTP, 350 nM dGTP, 235 nM dTTP, 12 nM biotin-16-dUTP, 23.5 nM Dig-primer/template, 2 nM GST-UL54. The assay volume is 10 μL. Each reagent is added as follow: 4 μL a+3 μL b+3 μL c; a: compound diluted in compound dilution buffer to obtain 12.5% DMSO; b: enzyme (GST-UL54) in 10 mM Hepes pH 7.5, 25 mM KCl, 5 mM MgCl$_2$, 25 mM NaCl, 5% Glycerol, 0.67 mg BSA/mL, 1 mM TCEP w/o DMSO (2 nM GST-UL54 is present in the assay); c: substrate in 10 mM HEPES pH 7.5, 25 mM KCl, 5 mM MgCl$_2$, 1 mM TCEP, 783 nM dATP, 1166 nM dCTP, 1166 nM dGTP, 783 nM dTTP, 40 nM biotin-16-dUTP, 78 nM Dig-primer (5'-/Dig/AGC TCG TTT AGT GAA CC-3' (SEQ ID NO: 1))/template (5'-GAG GTC AAA ACA GCG TGG ATG GCG TCT CCA GGC GAT CTG ACG GTT CAC TAA ACG AGC T-3' (SEQ ID NO: 2)) w/o DMSO. The primer and template are annealed in 10 mM Tris-HCl pH 7.5, 50 mM NaCl at a respective concentration of 50 μM. They are incubated at 95° C. for 5 min in a dry batch block. The block is removed from the dry bath and allowed to cool to RT. Aliquots are made and stored at −20° C.

To perform the assay, 3 μL of the enzyme solution is added to columns 2-12 and 14-24. The enzyme is substituted by the blank solution (b solution without enzyme) for columns 1 and 13 (blanks). The plate is centrifuged at 200×g for 30 sec. 3 μL of substrate solution is added to each well. The plate is centrifuged at 200×g for 30 sec. Plates are incubated at 37° C. for 30 min. 5 μL of conjugate solution is added (25 mM Hepes pH 7.5, 0.1 M NaCl, 0.25% Tween-20, 1 mg/mL BSA, 12 mM EDTA, 24 nM Sreptavidin-APC, 342 ng/mL Anti-Dig-Europium). The plates are incubated at RT for at least 120 min. The signal is read on the Envision plate reader (Perkin-Elmer) or equivalent.

All compounds of the invention are tested in the assay described in Example B and show IC$_{50}$ values in the range of 5 μM or less. Representative data is shown in the table below:

| Cmpd # | IC$_{50}$ (nM) Example B | Cmpd # | IC$_{50}$ (nM) Example B |
|---|---|---|---|
| 11a1 | 580 | 19b2 | 990 |
| 16c3 | 600 | 19c2 | 420 |
| 11e1 | 240 | 13o1 | 3200 |
| 11f1 | 95 | 22l1.2 | 380 |
| 11g1 | 200 | 22o1 | 2900 |
| 11h1 | 94 | 22s1 | 550 |
| 17b1 | 330 | 13r1 | 360 |
| 13b1 | 34 | 13t1 | 730 |
| 19a2 | 350 | 22u1 | 570 |
| 13d1 | 110 | 22v1 | 790 |
| 13a1 | 150 | 22w1 | 470 |
| 13f1 | 140 | 13v1 | 1600 |
| 13g1 | 2100 | 22z1 | 1300 |
| 11q1 | 49 | 22bb1 | 350 |
| 11r1 | 480 | 13w1 | 840 |
| 11s1 | 590 | 13x1 | 50 |
| 22a2 | 260 | 17n1 | 540 |
| 13l1 | 230 | 17o1 | 240 |
| 11t1 | 370 | 24a1 | 690 |
| 11v1 | 510 | 11oo1 | 1600 |
| 11bbb1 | 310 | 11qq1 | 750 |
| 11ccc1 | 87 | 24d1 | 550 |
| 11ddd1 | 38 | 22dd1 | 290 |
| 11aa1 | 100 | 31a1 | 86 |
| 11dd1 | 71 | 11rr1 | 350 |
| 22j1 | 480 | 11ss1 | 130 |
| 11ee1 | 63 | 11vv1 | 160 |
| 11hh1 | 150 | 11zz1 | 99 |

Each reference, including all patents, patent applications, and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

The invention claimed is:

1. A compound of Formula (I) or a racemate, enantiomer, diastereomer or tautomer thereof:

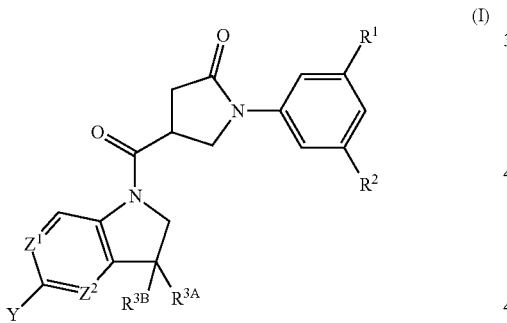

wherein
R$^1$ is H and R$^2$ is —Cl or —CN;
R$^{3A}$ and R$^{3B}$ are each independently selected from the group consisting of H and methyl wherein said methyl is optionally substituted with R$^{32}$;
or R$^{3A}$ and R$^{3B}$, together with the C to which they are attached, are linked to form a tetrahydropyranyl, N-acetylpiperidinyl or cyclopropyl;
R$^{32}$ is OH;
Z$^1$ is C(R$^4$);
R$^4$ is H, halo, —CH$_3$, or Y is —CH$_2$R$^5$, —CH$_2$CH$_2$R$^5$, —CH$_2$CH(CH$_3$)CH$_2$R$^5$ or —CH$_2$N(CH$_3$)CH$_2$R$_5$;
R$^5$ is phenyl, morpholinyl, or heteroaryl selected from imidazolyl, pyrimidinyl, pyridinyl, pyridazinyl, pyrazinyl, pyrazolyl, oxazolyl, isoxazolyl, [1,2,4]-triazolyl or [1,3,4]-triazolyl, wherein each said phenyl and heteroaryl are optionally mono- or di-substituted with R$^{52}$;
R$^{52}$ is each independently selected from the group consisting of (C$_{1-3}$)alkyl, —CN, —OH, —OCH$_3$, F, —NH$_2$, and —NH(CH$_3$));
Z$^2$ is C(R$^6$);
R$^6$ is H, halo or —CH$_3$;
or a salt thereof.

2. The compound according to claim 1, wherein R$^{3A}$ and R$^{3B}$ are each independently selected from the group consisting of H and —CH$_3$;
or a pharmaceutically acceptable salt thereof.

3. The compound according to claim 1, wherein Z$^1$ is CH;
or a pharmaceutically acceptable salt thereof.

4. The compound according to claim 1, wherein Y is —CH$_2$R$^5$ or —CH$_2$CH$_2$R$^5$;
or a pharmaceutically acceptable salt thereof.

5. The compound according to claim 1, wherein Z$^2$ is CH;
or a pharmaceutically acceptable salt thereof.

6. A method for the treatment of CMV disease or infection comprising administering a therapeutically effective amount of a compound according to claim 1 to a patient in need thereof.

7. A pharmaceutical composition comprising a compound according to claim 1, or a pharmaceutically acceptable salt thereof, and a pharmaceutically acceptable carrier.

* * * * *

SEQUENCE LISTING

```
<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5'-Dig

<400> SEQUENCE: 1
agctcgttta gtgaacc                                                  17

<210> SEQ ID NO 2
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaggtcaaaa cagcgtggat ggcgtctcca ggcgatctga cggttcacta aacgagct     58
```